US011963801B2

(12) United States Patent
Budiman et al.

(10) Patent No.: US 11,963,801 B2
(45) Date of Patent: Apr. 23, 2024

(54) SYSTEMS AND METHODS FOR USE OF INSULIN INFORMATION FOR MEAL INDICATION

(71) Applicant: ABBOTT DIABETES CARE INC., Alameda, CA (US)

(72) Inventors: Erwin S. Budiman, Fremont, CA (US); Kenneth J. Doniger, Menlo Park, CA (US); Timothy C. Dunn, San Francisco, CA (US); Nathan C. Crouther, San Francisco, CA (US); Glenn Berman, Alameda, CA (US); Howard A. Wolpert, Brookline, MA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1178 days.

(21) Appl. No.: 16/005,234

(22) Filed: Jun. 11, 2018

(65) Prior Publication Data

US 2019/0053765 A1 Feb. 21, 2019

Related U.S. Application Data

(63) Continuation of application No. 14/214,901, filed on Mar. 15, 2014, now Pat. No. 10,010,291.
(Continued)

(51) Int. Cl.
*A61B 5/00* (2006.01)
*A61B 5/145* (2006.01)
(Continued)

(52) U.S. Cl.
CPC ........ *A61B 5/7275* (2013.01); *A61B 5/14532* (2013.01); *A61B 5/4848* (2013.01);
(Continued)

(58) Field of Classification Search
CPC . A61B 5/7275; A61B 5/14532; A61B 5/4848; A61B 5/7282; A61B 5/742;
(Continued)

(56) References Cited

U.S. PATENT DOCUMENTS 4,695,954 A 9/1987 Rose et al.
4,731,726 A 3/1988 Allen, III
(Continued)

FOREIGN PATENT DOCUMENTS

GB 2 443 434 5/2008
JP 2001-245900 9/2001
(Continued)

OTHER PUBLICATIONS

EP, 14762430.8 Extended Search Report, dated Apr. 3, 2017.
(Continued)

*Primary Examiner* — Mohamed Barakat
*Assistant Examiner* — Rufus C Point
(74) *Attorney, Agent, or Firm* — Sterne, Kessler, Goldstein & Fox P.L.L.C.

(57) ABSTRACT

A system and method provides a glucose report for determining glycemic risk based on an ambulatory glucose profile of glucose data over a time period, a glucose control assessment based on median and variability of glucose, and indicators of high glucose variability. Time of day periods are shown at which glucose levels can be seen. A median glucose goal and a low glucose line provide coupled with glucose variability provide a view into effects that raising or lowering the median goal would have. Likelihood of low glucose, median glucose compared to goal, and variability of glucose below median provide probabilities based on glucose data. Patterns can be seen and provide guidance for treatment.

19 Claims, 65 Drawing Sheets

Related U.S. Application Data

(60) Provisional application No. 61/922,765, filed on Dec. 31, 2013, provisional application No. 61/799,139, filed on Mar. 15, 2013.

(51) Int. Cl.
  *G01N 33/66* (2006.01)
  *G16H 15/00* (2018.01)
  *G16H 20/10* (2018.01)
  *G16H 50/30* (2018.01)
  *G16Z 99/00* (2019.01)

(52) U.S. Cl.
  CPC ............ *A61B 5/7282* (2013.01); *A61B 5/742* (2013.01); *G01N 33/66* (2013.01); *G16H 20/10* (2018.01); *G16H 50/30* (2018.01); *G16Z 99/00* (2019.02); *A61B 5/4836* (2013.01); *A61B 5/746* (2013.01); *G16H 15/00* (2018.01)

(58) Field of Classification Search
  CPC ...... A61B 5/4836; A61B 5/746; G01N 33/66; G16H 20/10; G16H 50/30; G16H 15/00; G16Z 99/00
  See application file for complete search history.

(56) References Cited

U.S. PATENT DOCUMENTS

| | | |
|---|---|---|
| 4,779,199 A | 10/1988 | Yoneda et al. |
| 4,817,044 A | 3/1989 | Ogren |
| 5,019,974 A | 5/1991 | Beckers |
| 5,216,597 A | 6/1993 | Beckers et al. |
| 5,251,126 A | 10/1993 | Kahn et al. |
| 5,307,263 A | 4/1994 | Brown |
| 5,319,363 A | 6/1994 | Welch et al. |
| 5,341,291 A | 8/1994 | Roizen et al. |
| 5,376,070 A | 12/1994 | Purvis et al. |
| 5,500,854 A | 3/1996 | Uotila et al. |
| 5,558,638 A | 9/1996 | Evers et al. |
| 5,569,186 A | 10/1996 | Lord et al. |
| 5,590,648 A | 1/1997 | Mitchell et al. |
| 5,626,144 A | 5/1997 | Tacklind et al. |
| 5,665,065 A | 9/1997 | Colman et al. |
| 5,704,366 A | 1/1998 | Tacklind et al. |
| 5,713,856 A | 2/1998 | Eggers et al. |
| 5,772,586 A | 6/1998 | Heinonen et al. |
| 5,822,715 A | 10/1998 | Worthington et al. |
| 5,878,384 A | 3/1999 | Johnson et al. |
| 5,925,021 A | 7/1999 | Castellano et al. |
| 5,946,659 A | 8/1999 | Lancelot et al. |
| 5,960,403 A | 9/1999 | Brown |
| 5,974,389 A | 10/1999 | Clark et al. |
| 5,997,476 A | 12/1999 | Brown |
| 6,022,315 A | 2/2000 | Iliff |
| 6,024,699 A | 2/2000 | Surwit et al. |
| 6,049,764 A | 4/2000 | Stahl |
| 6,081,786 A | 6/2000 | Barry et al. |
| 6,134,504 A | 10/2000 | Douglas et al. |
| 6,144,922 A | 11/2000 | Douglas et al. |
| 6,175,752 B1 | 1/2001 | Say et al. |
| 6,188,988 B1 | 2/2001 | Barry et al. |
| 6,206,829 B1 | 3/2001 | Iliff |
| 6,225,901 B1 | 5/2001 | Kail, IV |
| 6,234,964 B1 | 5/2001 | Iliff |
| 6,270,455 B1 | 8/2001 | Brown |
| 6,277,071 B1 | 8/2001 | Hennessy et al. |
| 6,336,900 B1 | 1/2002 | Alleckson et al. |
| 6,338,713 B1 | 1/2002 | Chamoun et al. |
| 6,352,505 B1 | 3/2002 | Bortz |
| 6,368,273 B1 | 4/2002 | Brown |
| 6,379,301 B1 | 4/2002 | Worthington et al. |
| 6,390,986 B1 | 5/2002 | Curcie et al. |
| 6,406,426 B1 | 6/2002 | Reuss et al. |
| 6,418,346 B1 | 7/2002 | Nelson et al. |
| 6,422,061 B1 | 7/2002 | Sunshine et al. |
| 6,450,956 B1 | 9/2002 | Rappaport et al. |
| 6,524,240 B1 | 2/2003 | Thede |
| 6,540,672 B1 | 4/2003 | Simonsen et al. |
| 6,544,174 B2 | 4/2003 | West et al. |
| 6,544,212 B2 | 4/2003 | Galley et al. |
| 6,551,243 B2 | 4/2003 | Bocionek et al. |
| 6,558,351 B1 | 5/2003 | Steil et al. |
| 6,575,900 B1 | 6/2003 | Zweig et al. |
| 6,604,050 B2 | 8/2003 | Trippel et al. |
| 6,611,846 B1 | 8/2003 | Stoodley |
| 6,635,016 B2 | 10/2003 | Finkelshteins |
| 6,635,167 B1 | 10/2003 | Batman et al. |
| 6,645,142 B2 | 11/2003 | Braig et al. |
| 6,656,114 B1* | 12/2003 | Poulsen ................ G16H 20/17 128/920 |
| 6,692,436 B1 | 2/2004 | Bluth et al. |
| 6,781,522 B2 | 8/2004 | Sleva et al. |
| 6,799,149 B2 | 9/2004 | Hartlaub |
| 6,804,558 B2 | 10/2004 | Haller et al. |
| 6,872,200 B2 | 3/2005 | Mann et al. |
| 6,915,170 B2 | 7/2005 | Engleson et al. |
| 7,241,265 B2 | 7/2007 | Cummings et al. |
| 7,920,907 B2 | 4/2011 | McGarraugh et al. |
| 8,409,093 B2 | 4/2013 | Bugler |
| 8,758,245 B2 | 6/2014 | Ray et al. |
| 9,579,231 B2 | 2/2017 | Galvin |
| 2001/0039503 A1 | 11/2001 | Chan et al. |
| 2003/0114836 A1 | 6/2003 | Estes et al. |
| 2003/0208113 A1* | 11/2003 | Mault .................... G16H 40/63 600/316 |
| 2003/0211617 A1* | 11/2003 | Jones .................... G01N 33/66 436/95 |
| 2003/0216628 A1 | 11/2003 | Bortz et al. |
| 2004/0091424 A1 | 5/2004 | Asano et al. |
| 2005/0027182 A1 | 2/2005 | Siddiqui et al. |
| 2005/0038332 A1 | 2/2005 | Saidara et al. |
| 2005/0119540 A1 | 6/2005 | Potts et al. |
| 2005/0159656 A1 | 7/2005 | Hockersmith et al. |
| 2005/0187789 A1 | 8/2005 | Hattlestad et al. |
| 2005/0214892 A1 | 9/2005 | Kovatchev et al. |
| 2005/0267780 A1 | 12/2005 | Ray et al. |
| 2006/0010098 A1 | 1/2006 | Goodnow et al. |
| 2006/0106644 A1 | 5/2006 | Koo et al. |
| 2006/0173260 A1 | 8/2006 | Gaoni et al. |
| 2006/0189863 A1 | 8/2006 | Peyser et al. |
| 2006/0264895 A1 | 11/2006 | Flanders |
| 2006/0276771 A1 | 12/2006 | Galley et al. |
| 2007/0016449 A1 | 1/2007 | Cohen et al. |
| 2007/0033074 A1 | 2/2007 | Nitzan et al. |
| 2007/0106135 A1 | 5/2007 | Sloan et al. |
| 2007/0149874 A1 | 6/2007 | Say et al. |
| 2007/0179352 A1 | 8/2007 | Randlov et al. |
| 2007/0179370 A1 | 8/2007 | Say et al. |
| 2007/0208244 A1 | 9/2007 | Brauker et al. |
| 2008/0071580 A1 | 3/2008 | Marcus et al. |
| 2008/0119710 A1 | 5/2008 | Reggiardo et al. |
| 2008/0154513 A1 | 6/2008 | Kovatchev et al. |
| 2008/0234943 A1 | 9/2008 | Rat et al. |
| 2008/0234992 A1 | 9/2008 | Ray et al. |
| 2008/0235053 A1 | 9/2008 | Ray et al. |
| 2008/0255438 A1 | 10/2008 | Saidara et al. |
| 2008/0262469 A1 | 10/2008 | Brister et al. |
| 2009/0055149 A1 | 2/2009 | Hayter et al. |
| 2009/0105573 A1 | 4/2009 | Malecha |
| 2009/0171589 A1 | 7/2009 | Kovatchev |
| 2009/0192380 A1 | 7/2009 | Shariati et al. |
| 2009/0216102 A1 | 8/2009 | Say et al. |
| 2009/0221890 A1 | 9/2009 | Saffer et al. |
| 2009/0240127 A1 | 9/2009 | Ray |
| 2010/0152554 A1 | 6/2010 | Steine et al. |
| 2010/0161236 A1 | 6/2010 | Cohen et al. |
| 2010/0191472 A1 | 7/2010 | Doniger et al. |
| 2010/0198314 A1 | 8/2010 | Wei |
| 2010/0332445 A1 | 12/2010 | Ray et al. |
| 2011/0077494 A1 | 3/2011 | Doniger et al. |
| 2011/0130746 A1 | 6/2011 | Budiman |
| 2011/0264378 A1 | 10/2011 | Breton et al. |

(56) References Cited

U.S. PATENT DOCUMENTS

| | | | |
|---|---|---|---|
| 2012/0143021 A1* | 6/2012 | Nagar | A61B 5/4839 606/191 |
| 2012/0277619 A1* | 11/2012 | Starkebaum | A61B 5/6871 607/40 |
| 2013/0035575 A1 | 2/2013 | Mayou et al. | |
| 2013/0321425 A1* | 12/2013 | Greene | G16H 15/00 345/440 |
| 2013/0338630 A1* | 12/2013 | Agrawal | G16H 40/63 604/504 |
| 2014/0030748 A1 | 1/2014 | Schaible | |
| 2014/0088392 A1 | 3/2014 | Bernstein et al. | |
| 2014/0088393 A1 | 3/2014 | Bernstein et al. | |
| 2014/0275748 A1* | 9/2014 | Dunki-Jacobs | A61B 5/0537 604/66 |
| 2014/0350369 A1* | 11/2014 | Budiman | A61B 5/742 702/19 |
| 2015/0190098 A1* | 7/2015 | Patek | A61B 5/7278 600/365 |

FOREIGN PATENT DOCUMENTS

| | | |
|---|---|---|
| JP | 2003-500744 | 1/2003 |
| JP | 2004-024699 | 1/2004 |
| WO | WO 99/56613 A1 | 11/1999 |
| WO | WO 00/04512 A2 | 1/2000 |
| WO | WO 02/05702 A2 | 1/2002 |
| WO | WO 2004/009161 A1 | 1/2004 |
| WO | WO 2005/081170 A2 | 9/2005 |
| WO | WO 2006/079867 A1 | 8/2006 |
| WO | WO 2008/030347 A2 | 3/2008 |
| WO | WO 2009/146119 A2 | 12/2009 |
| WO | WO 2011/041007 A1 | 4/2011 |
| WO | WO 2011/060923 A2 | 5/2011 |

OTHER PUBLICATIONS

WO, PCT/US2014/030075 ISR and Written Opinion, dated Aug. 6, 2014.

Bergenstal, R., et al., "Recommendations for Standardizing Glucose Reporting and Analysis to Optimize Clinical Decision Making in Diabetes: The Ambulatory Glucose Profile (AGP)", Diabetes Technology & Therapeutics, 2011, vol. 15, No. 3, pp. 198-211.

Breton, M., et al., "A Model of Self-Treatment Behavior, Glucose Variability, and Hypoglycemia-Associated Autonomic Failure in Type 1 Diabetes", Journal of Diabetes Science and Technology, 2007, vol. 1, No. 3, pp. 331-337.

Brownlee, M., et al., "Glycemic Variability: A Hemoglobin A1c-Independent Risk Factor for Diabetic Complications", JAMA, 2006, vol. 295, No. 14, pp. 1707-1708.

Fritzsche, G., et al., "The Use of a Computer Program to Calculate the Mean Amplitude of Glycemic Excursions", Diabetes Technology & Therapeutics, 2011, vol. 13, No. 3, pp. 319-325.

Harvey, R.A., et al., "Clinically Relevant Hypoglycemia Prediction Metrics for Event Mitigation", Diabetes Technology & Therapeutics, 2012, vol. 14, No. 8, pp. 719-727.

Hughes, C.A., et al., " Hypoglycemia Prevention via Pump Attenuation and Red-Yellow-Green "Traffic" Lights Using Continuous Glucose Monitoring and Insulin Pump Data", Journal of Diabetes Science and Technology, 2010, vol. 4, No. 5, pp. 1146-1155.

Kilpatrick, E. S., "The Effect of Glucose Variability on the Risk of Microvascular Complications in Type 1 Diabetes", Diabetes Care, 2006, vol. 29, No. 7, pp. 1486-1490.

Kovatchev, B. P., et al., "Quantifying Temporal Glucose Variability in Diabetes via Continuous Glucose Monitoring: Mathematical Methods and Clinical Application", Diabetes Technology & Therapeutics, 2005, vol. 7, No. 6, pp. 849-862.

Mazze, R. S., "Ambulatory Glucose Profile: Representation of Verified Self-Monitored Blood Glucose Data", Diabetes Care, 1987, vol. 10, No. 1, pp. 111-117.

Mazze, R. S., "Characterizing Glucose Exposure for Individuals with Normal Glucose Tolerance Using Continuous Glucose Monitoring and Ambulatory Glucose Profile Analysis", Diabetes Technology & Therapeutics, 2008, vol. 10, No. 3, pp. 149-159.

Rodbard, D., "Optimizing Display, Analysis, Interpretation and Utility of Self-Monitoring of Blood Glucose (SMBG) Data for Management of Patients with Diabetes", Journal of Diabetes Science and Technology, 2007, vol. 1, No. 1, pp. 62-71.

Wilson, D. M., "The Accuracy of the FreeStyle Navigator Continuous Glucose Monitoring System in Children With Type 1 Diabetes ", Diabetes Care, 2007, vol. 30, No. 1, pp. 59-64.

Cunningham, David D. and Stenken, Julia A., Editors, "In Vivo Glucose Sensing," Chemical Analysis, vol. 174, John Wiley & Sons, Inc., Hoboken, NJ 2010; 466 pages.

PMA Approvals FDA—webpage available at: https://www.fda.gov; 3 pages.

PMA database search for Freestyle Navigator Continuous Glucose Monitor—https://www.fda.gov; 6 pages.

Getting Started with CareLink Personal Software Continuous Glucose Monitoring; Medtronic, 2009, 28 pages.

Sparacino, Giovanni et al., "Glucose Concentration can be Predicted Ahead in Time From Continuous Glucose Monitoring Sensor Time-Series," IEEE Transactions on Biomedical Engineering, Vo. 54, No. 5, May 2007; 7 pages.

Sandham, William et al., "Blood Glucose Prediction for Diabetes Therapy Using a Recurrent Artificial Neural Network," 9th European Signal Processing Conference (EUSIPCO 1998), 1998, pp. 1-4.

FreeStyle Navigator Continuous Glucose Monitoring System, User's Guide, Abbott Diabetes Care Inc., May 2008; 195 pages.

Exhibit CP-3, Expert Report of Dr. Cesar C. Palerm, Sep. 20, 2022: "In Vivo Glucose Sensing, Chemical Analysis, A Series of Monographs on Analytical Chemistry and Its Applications," vol. 174, Wiley (2010) Chp. 5, pp. 143-147.

Exhibit CP-4, Expert Report of Dr. Cesar C. Palerm, Sep. 20, 2022, "Animas® Vibe™, the First Integrated Offering from Animas Corporation and Dexcom, Inc, Receives European CE Mark Approval", Products & Operating Company, 2011, 4 pages.

Exhibit CP-6, Second Expert Report of Dr. Cesar C. Palerm, Oct. 21, 2022, Bailey, T.S. et al., "Reduction in Hemoglobin A1c with Real-Time Continuous Glucose Monitoring: Results from a 12-Week Observational Study" Diabetes Technology & Therapeutics, 2007, 9(3):203-210.

Exhibit CP-7, Second Expert Report of Dr. Cesar C. Palerm, Oct. 21, 2022, Garg, S. et al., "Improvement in Glycemic Excursions with a Transcutaneous, Real-Time Continuous Glucose Sensor", Diabetes Care, 2006, 29(12):44-50.

Exhibit CP-8, Second Expert Report of Dr. Cesar C. Palerm, Oct. 21, 2022, Garg, S et al., Relationship of Fasting and Hourly Blood Glucose Levels to HbA1c Values, Diabetes Care, 2006, 6(12):2644-2649.

Exhibit CP-10, Second Expert Report of Dr. Cesar C. Palerm, Oct. 21, 2022, "Standards of Medical Care in Diabetes-2009" Position Statement, American Diabetes Association, 2009, Diabetes Care, 32(1):S13-S61.

Exhibit No. 2, to the Expert Report of Professor Nick Oliver, Sep. 20, 2022, "Note for Guidance on Clinical Investigation of Medicinal Products in the Treatment of Diabetes Mellitus, " The European Agency for the Evaluation of Medicinal Products, 2002, 12 pages.

Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.

Exhibit No. 4, to the Expert Report of Professor Nick Oliver, Sep. 20, 2022, Amiel, S. A., et al., "Hypoglycaemia in Type 2 diabetes", Diabetic Medicine, 2008, 25:245-254.

Exhibit No. 5, to the Expert Report of Professor Nick Oliver, Sep. 20, 2022, Swinnen, S.G.H.A. et al., "Changing the glucose cut-off values that define Hypoglycaemia has a major effect on reported frequencies of hypoglycaemia", Diabetologia, 2009, 52:38-41.

Exhibit No. 6, to the Expert Report of Professor Nick Oliver, Sep. 20, 2022, Frier, B.M. "Defining hypoglycaemia: what level has clinical relevance?", Diabetologia, 2009, 52:31-34.

(56) References Cited

OTHER PUBLICATIONS

Exhibit No. 7, to the Expert Report of Professor Nick Oliver, Sep. 20, 2022, Cryer, P.E. "Preventing Hypoglycaemia: what is the appropriate glucose alert value?" Diabetologia, 2009, 53:35-37.
Exhibit No. 8, to the Expert Report of Professor Nick Oliver, Sep. 20, 2022, Choudhary P. et al., "Hypoglycaemia in the treatment of diabetes mellitus" Oxford Textbook of Endocrinology and Diabetes, 2011 pp. 1849-1860.
Exhibit No. 9, to the Expert Report of Professor Nick Oliver, Sep. 20, 2022, "Guideline on clinical investigation of medicinal products in the treatment or prevention of diabetes mellitus" European Medicines Agency, May 14, 2012, 28 pages.
Exhibit No. 10, to the Expert Report of Professor Nick Oliver, Sep. 20, 2022, "Type 1 Diabetes Research Roadmap, Identifying the strengths and weaknesses, gaps and opportunities of UK type 1 diabetes research; clearing a path to the cure", Type 1 diabetes research roadmap, JDRF, 2013, 21 pages.
Exhibit No. 11, to the Expert Report of Professor Nick Oliver, Sep. 20, 2022, "The Effect of Intensive Treatment of Diabetes on the Development and Progression of Long-Tern Complications in Insulin-Dependent Diabetes Mellitus" The New England Journal of Medicine, 1993, 329(14):977-986.
Exhibit No. 12, to the Expert Report of Professor Nick Oliver, Sep. 20, 2022, National Service Framework for Diabetes: Standards, Dept. of Health, 2002, 48 pages.
Exhibit No. 13, to the Expert Report of Professor Nick Oliver, Sep. 20, 2022, Amiel, S. et al., "Training in flexible, intensive insulin management to enable dietary freedom in people with type 1 diabetes: dose adjustment for normal eating (DAFNE) randomized controlled trial" BMJ, 2002, 325; 6 pages.
Exhibit No. 14, to the Expert Report of Professor Nick Oliver, Sep. 20, 2022, "Type 1 diabetes: diagnosis and management of type 1 diabetes in children, young people and adults" National Institute for Clinical Excellence, Clinical Guideline 15, Jul. 2004, 113 pages.
Exhibit No. 15, to the Expert Report of Professor Nick Oliver, Sep. 20, 2022, Pickup, John C. "Glucose monitoring", Oxford Textbook of Endocrinology and Diabetes, 2011, pp. 1861-1869.
Exhibit No. 16, to the Expert Report of Professor Nick Oliver, Sep. 20, 2022, Pickup, J.C. et al., "Glycaemic control in type 1 diabetes during real time continuous glucose monitoring compared with self monitoring of blood glucose: meta-analysis of randomised controlled trials using individual patient data" BMJ, 2011; 14 pages.
Exhibit No. 17, to the Expert Report of Professor Nick Oliver, Sep. 20, 2022, "Diabetes (type 1), PSP Top 10", James, Lind Alliance, Priority Setting Partnerships, 2011, 4 pages.
Exhibit No. 20, to the Expert Report of Professor Nick Oliver, Sep. 20, 2022, "Continuous Glucose Sensors: Continuing Questions about Clinical Accuracy" Journal of Diabetes Science and Technology, 2007; 1(5):669-675.
Exhibit No. 21, to the Expert Report of Professor Nick Oliver, Sep. 20, 2022, DeVries, J.H. "Glucose Sensing Issues for the Artificial Pancreas" Journal of Diabetes Science and Technology, 2008, 2(4):732-734.
Exhibit No. 23, to the Expert Report of Professor Nick Oliver, Sep. 20, 2022, Internet Archive, WayBack Machine, Medtronic MiniMed, 2004, 20 pages.
Exhibit No. 24, to the Expert Report of Professor Nick Oliver, Sep. 20, 2022, "Glucowatch G2, Automatic Glucose Biographer and Autosensors," 2002, 70 pages.
Exhibit No. 25, to the Expert Report of Professor Nick Oliver, Sep. 20, 2022, "Guardian® REAL-Time Continuous Glucose Monitoring System, User Guide," Medtronic MiniMed, 2006, 181 pages.
Exhibit No. 26, to the Expert Report of Professor Nick Oliver, Sep. 20, 2022, "CGMS® iProTM Continuous Glucose Recorder, User Guide," Medtronic MiniMed, 2007, 36 pages.
Exhibit No. 27, to the Expert Report of Professor Nick Oliver, Sep. 20, 2022, "FreeStyle Navigator Continuous Glucose Monitoring System, User Guide," Abbott, 2008, 2010, 135 pages.
Exhibit No. 28, to the Expert Report of Professor Nick Oliver, Sep. 20, 2022, FreeStyle Navigator II Continuous Glucose Monitoring System, User's Manual, Abbott, 2011-2013, 21 pages.
Exhibit No. 29, to the Expert Report of Professor Nick Oliver, Sep. 20, 2022, "Dexcom G4 Continuous Glucose Monitoring System, User's Guide," Dexcom, 2013, 156 pages.
Exhibit No. 30, to the Expert Report of Professor Nick Oliver, Sep. 20, 2022, Revised specification for publication No. US2007208244A1, 2007, 170 pages.
Exhibit No. 31, to the Expert Report of Professor Nick Oliver, Sep. 20, 2022, Revised Specification for EP625, 2008, 30 pages.
Exhibit No. 32, to the Expert Report of Professor Nick Oliver, September 20, 2022, Puhr, S. et al., "Real-World Hypoglycemia Avoidance with a Predictive Low Glucose Alert Does Not Depend on Frequent Screen Views", Journal of Diabetes Sciences and Technology, 2004, 14(1): 83-86.
Exhibit No. 37, to the Second Expert Report of Professor Nick Oliver, Oct. 21, 2022, Oliver, N.S., et al., "Glucose sensors: a review of current and emerging technology", Diabetic Medicine, 2009, 26:197-210.
"Dexcom's 7-Day Continuous Glucose Monitoring System," Jun. 1, 2007, https://newatlas.com/; 1 page.
U.S. Pat. No. 8,282,549 B2, Brauker et al., published Oct. 9, 2012; 73 pages; Anlage TW 2, Taylor Wessing, Statement of Defence in *Abbott* v. *Dexcom*, Opposition to EP 3782539.
STS-7 Continuous Glucose Monitoring System User's Guide, 74 pages; 2007; Anlage TW 11 D5a, Taylor Wessing, Statement of Defence in *Abbott* v. *Dexcom*, Opposition to EP 3782539.
Summary of Safety and Effectiveness Data for STS-7 Continuous Glucose Monitoring System, Notice of Approval dated May 31, 2007; 14 pages; Anlage TW 11 D5b, Taylor Wessing, Statement of Defence in *Abbott* v. *Dexcom*, Opposition to EP 3782539.
Letter from Department of Health and Human Services to DexCom Inc. regarding STS-7 Continuous Glucose Monitoring System, dated May 31, 2007; 95 pages; Anlage TW 25, Taylor Wessing, Statement of Defence in *Abbott* v. *Dexcom*, Opposition to EP 3782539.

\* cited by examiner

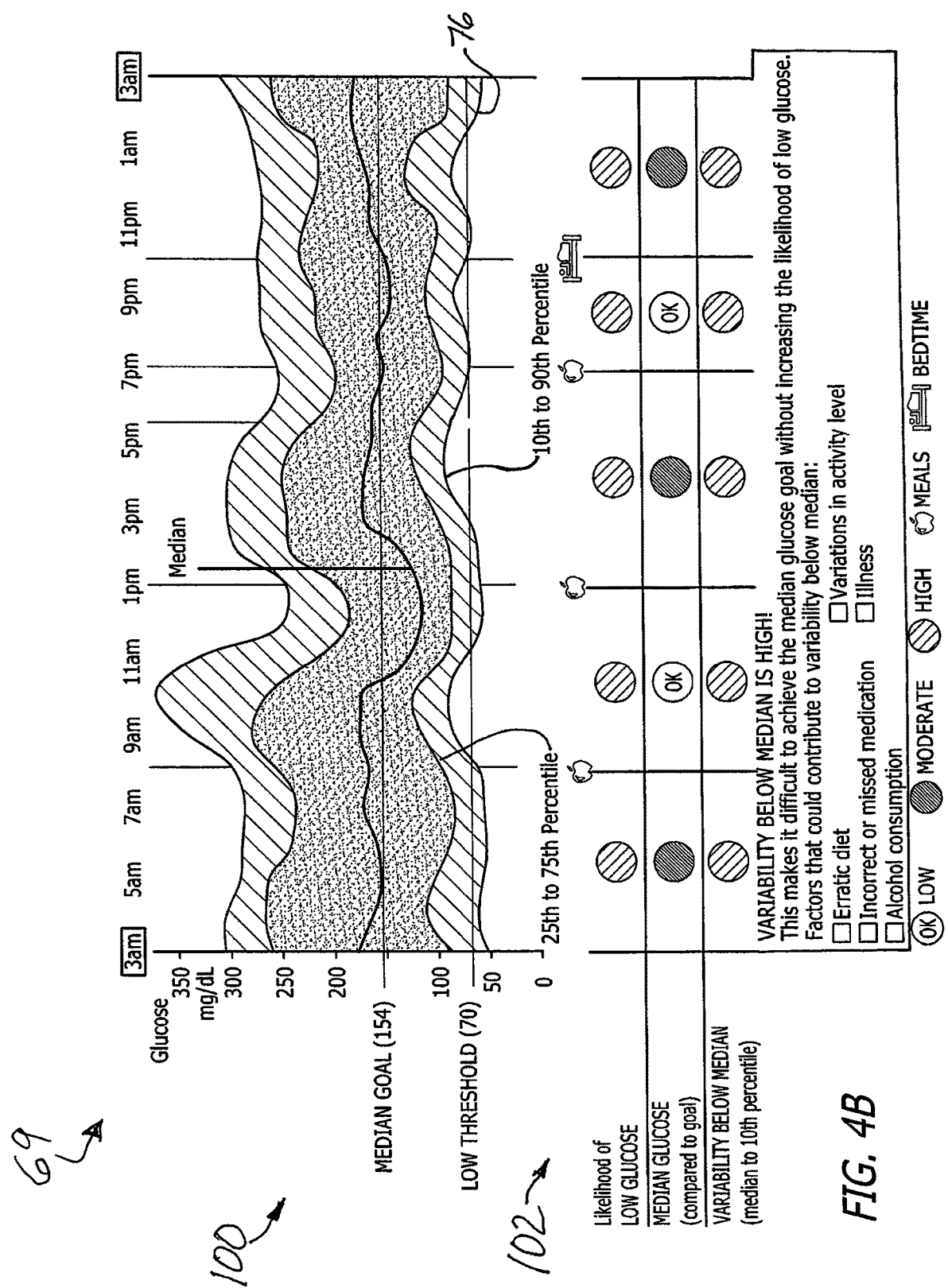

| Glucose Control Assessment | | Possible Action |
|---|---|---|
| Likelihood of LOW GLUCOSE | OK  OK | If not at A1C target, consider lowering Median Goal |
| MEDIAN GLUCOSE (compared to goal) | OK  OK | |
| VARIABILITY BELOW MEDIAN (median to 10th percentile) | OK  ◐ | |
| Likelihood of LOW GLUCOSE | ◐  ◐ | Decrease insulin coverage to reduce hypoglycemia risk |
| MEDIAN GLUCOSE (compared to goal) | OK  OK | |
| VARIABILITY BELOW MEDIAN (median to 10th percentile) | OK  OK | |
| Likelihood of LOW GLUCOSE | ◐  ◐  ◐ | 1. Address self-care behaviors to lower glucose variability to reduce hypoglycemia risk 2. If patient is unlikely to be able to reduce variability, decrease insulin coverage to reduce hypoglycemia risk |
| MEDIAN GLUCOSE (compared to goal) | OK  OK  OK | |
| VARIABILITY BELOW MEDIAN (median to 10th percentile) | ◐  ◐  ◐ | |
| Likelihood of LOW GLUCOSE | ◐  ◐  ◐ | |
| MEDIAN GLUCOSE (compared to goal) | ◐  ◐  ◐ | |
| VARIABILITY BELOW MEDIAN (median to 10th percentile) | ◐  ◐  ◐ | |
| Likelihood of LOW GLUCOSE | OK | Increase insulin coverage to reduce hyperglycemia |
| MEDIAN GLUCOSE (compared to goal) | ◐ | |
| VARIABILITY BELOW MEDIAN (median to 10th percentile) | OK | |
| Likelihood of LOW GLUCOSE | OK  OK | 1. Increase insulin coverage to reduce hyperglycemia 2. Address self-care behaviors to lower glucose variability to reduce potential for hypoglycemia risk |
| MEDIAN GLUCOSE (compared to goal) | ◐  ◐ | |
| VARIABILITY BELOW MEDIAN (median to 10th percentile) | ◐  ◐ | |

FIG. 7

| Median Range | AUC70 Period | N | GCM | 10PCT Upper Limits (mg/dL) | | | | |
|---|---|---|---|---|---|---|---|---|
| | | | | 80 | 85 | 90 | 100 | 105 | 110 |
| All | In-Sample | 2735 (19.6%) | 15 (0.5%) | 319 (11.7%) | 203 (7.4%) | 128 (4.7%) | 53 (1.9%) | 33 (1.2%) | 24 (0.9%) |
| | Out-of-Sample | 2655 (19.1%) | 143 (5.4%) | 1008 (38%) | 741 (27.9%) | 548 (20.6%) | 300 (11.3%) | 217 (8.2%) | 159 (6%) |
| 155 and greater | In-Sample | 594 (10.5%) | 10 (1.7%) | 200 (33.7%) | 145 (24.4%) | 106 (17.8%) | 53 (8.9%) | 33 (5.6%) | 24 (4%) |
| | Out-of-Sample | 782 (13.8%) | 102 (13%) | 558 (71.4%) | 488 (62.4%) | 412 (52.7%) | 271 (34.7%) | 203 (26%) | 153 (19.6%) |
| 154 and less | In-Sample | 2141 (26%) | 5 (0.2%) | 119 (5.6%) | 58 (2.7%) | 22 (1%) | 0 (0%) | 0 (0%) | 0 (0%) |
| | Out-of-Sample | 1873 (22.7%) | 41 (2.2%) | 450 (24%) | 253 (13.5%) | 136 (7.3%) | 29 (1.5%) | 14 (0.7%) | 6 (0.3%) |

*FIG. 8*

| Median Range | AUC70 Period | N | GCM | 10PCT Lower Limits (mg/dL) | | | | |
|---|---|---|---|---|---|---|---|---|
| | | | | 70 | 75 | 80 | 90 | 95 | 100 |
| All | In-Sample | 2735 (19.6%) | 2416 (88.3%) | 1800 (65.8%) | 2177 (79.6%) | 2416 (88.3%) | 2607 (95.3%) | 2660 (97.3%) | 2682 (98.1%) |
| | Out-of-Sample | 2655 (19.1%) | 1583 (59.6%) | 997 (37.6%) | 1350 (50.8%) | 1647 (62%) | 2107 (79.4%) | 2259 (85.1%) | 2355 (88.7%) |
| 155 and greater | In-Sample | 594 (10.5%) | 474 (79.8%) | 225 (37.9%) | 315 (53%) | 394 (66.3%) | 488 (82.2%) | 524 (88.2%) | 541 (91.1%) |
| | Out-of-Sample | 782 (13.8%) | 318 (40.7%) | 111 (14.2%) | 165 (21.1%) | 224 (28.6%) | 370 (47.3%) | 451 (57.7%) | 511 (65.3%) |
| 154 and less | In-Sample | 2141 (26%) | 1942 (90.7%) | 1575 (73.6%) | 1862 (87%) | 2022 (94.4%) | 2119 (99%) | 2136 (99.8%) | 2141 (100%) |
| | Out-of-Sample | 1873 (22.7%) | 1265 (67.5%) | 886 (47.6%) | 1185 (63.3%) | 1423 (76%) | 1737 (92.7%) | 1808 (96.5%) | 1844 (98.5%) |

*FIG. 9*

| Red | High |  |
| Yellow | Moderate |  |
| Green | Low |  |
FIG. 10

FIG. 24

| | INPUT | INPUT | OUTPUTS | OUTPUTS | OUTPUTS |
|---|---|---|---|---|---|
| Stage | Treatments | Control Grid Zone | Recommendation Text | Guide Link | Q Link |
| Metformin | Metformin | Hypo Risk Zone | NA | NA | (TBD) |
| | | Buffer Zone | Decrease variability<br>Go to next treatment stage | MNT<br>2Drug Start | (TBD) |
| | | "Safe to Titrate" Zone | Increase Met dose<br>At max Met dose | Met Adj<br>2Drug Start | (TBD) |
| | | Target Zone | You're on target! | | |
| Two-Drug Therapy | Metformin + SU | Hypo Risk Zone | Decrease SU dose<br>Decrease Variability | SU Adj<br>MNT | (TBD) |
| | | Buffer Zone | Decrease Variability<br>Out of target for 3 mos? | MNT<br>3Drug Start | (TBD) |
| | | "Safe to Titrate" Zone | Increase SU dose<br>At max SU dose | SU Adj<br>3Drug Start | (TBD) |
| | | Target Zone | You're on target! | | |
| | Metformin + DPP-4 | Hypo Risk Zone | Decrease DPP-4 dose<br>Decrease Variability | DPP-4 Adj<br>MNT | (TBD) |
| | | Buffer Zone | Decrease Variability<br>Out of target for 3 mos? | MNT<br>3Drug Start | (TBD) |
| | | "Safe to Titrate" Zone | Increase DPP-4 dose<br>At max DPP-4 dose | DPP-4 Adj<br>3Drug Start | (TBD) |
| | | Target Zone | You're on target! | | |
| | etc... | | | | |
| Three-Drug Therapy | Met + SU + Basal Ins | Hypo Risk Zone | Decrease Basal dose<br>Decrease Variability | Basal Adj<br>MNT(*) | (TBD) |
| | | Buffer Zone | Decrease Variability<br>Out of target for 3 mos? | MNT(*)<br>T2 MDI Start | (TBD) |
| | | "Safe to Titrate" Zone | Increase Basal dose | SU Adj | (TBD) |
| | | Target Zone | "You're on target!" | | |
| | etc... | | | | |

FIG. 55B

Review Analysis

Patient Identifier: JDRF_023

[Home] [Review Printouts]

| Glucose Analysis | Guidance | Tracking |

Last Visit: (first visit) Instructions Notes

⊕ Summary
⊕ Self-care Guidance to Reduce Glucose Variability
⊖ Medication Adjustment

Overnight
Above Target
Mod Variability

Glucose levels are high overnight. Also, glucose variability is high. Consider the following action:
○ 1. Increase LA dose while reducing variability. Note that this may also lower glucose (more) after meals.

Breakfast to Lunch
Above Target
High Variability

Glucose levels are high after breakfast. However, high BG variability is contributing to hypoglycemia risk. Consider the following actions:
○ 1. Reduce variability, no RA breakfast dose adjustment (More)
○ 2. Or decrease RA breakfast dose, if variability cannot be reduced. (More)

Lunch to Dinner
Within Target
Mod Variability

Glucose levels are low after lunch. High glucose variability is contributing to hypoglycemia risk. Consider the following actions:
○ 1. Reduce variability, (More)
○ 2. Or decrease RA lunch dose, if variability cannot be reduced. (More)

Dinner to Bedtime
Within Target
Mod Hypo Risk

Glucose levels are low after dinner, contributing to hypoglycemia risk. Consider the following action:
○ 1. Decrease RA dinner dose. (More)

New Instructions

Previous Instructions

SYSTEMS AND METHODS FOR USE OF INSULIN INFORMATION FOR MEAL INDICATION

CROSS-REFERENCES TO RELATED APPLICATIONS

This application is a continuation of U.S. patent application Ser. No. 14/214,901, filed Mar. 15, 2014, which claims the benefit of U.S. Provisional Application No. 61/922,765, filed Dec. 31, 2013, and of U.S. Provisional Application No. 61/799,139, filed Mar. 15, 2013, all of which are incorporated herein by reference in their entireties.

BACKGROUND

Achieving euglycemia can be hampered by episodes of hypoglycemia and glucose variability which can now be tracked by continuous glucose monitoring ("CGM"). CGM devices have been shown to be clinically accurate in recording hypoglycemia, and can be used to assess diurnal patterns of glycemia. However, a challenge inherent to analysis of this influx of data is to represent it in a clinically meaningful manner that enables efficient clinical action. There is a need for glucose reports that can provide standardized, efficient output to effectively guide therapeutic decision making. Key benefits of glucose reports include a consistent view of glucose trends and patterns over the day, and showing the detail that A1C cannot. The identification of patterns of hypoglycemia and glucose variability can aid by guiding how aggressively the treatment can be safely adjusted.

Although present glucose reports have provided a way to analyze the influx of data from CGM, decision-making based on those reports and analyses can still be a challenge. Computerized algorithms have been developed as a way to simplify and guide the decision-making process. In hospital settings, computerized algorithms have been shown to improve patient outcomes by maintaining tight glucose control without increasing hypoglycemic events. In a clinical setting, computerized algorithms have also aided clinicians in correctly identifying glycemic patterns, making therapeutic decisions to address patterns, and teaching staff and patients.

Hence those skilled in the art have identified a need for presenting large amounts of CGM data in a useful manner. A need has also been recognized for analyzing CGM data so that possible effects in treatment changes can be analyzed. Further, a need has been recognized for a report that provides an overview of the glucose history of a patient and how effective the present treatment has been. Yet another need is for a glucose-based report that presents an overview of the patient's glucose history on an hourly basis annotated by certain periods of the day so that decisions may be made about possible treatment modification. The invention fulfills these needs and others.

Abbreviations—As used herein, the following abbreviations stand for the indicated terms:

A1C=glycated hemoglobin
AGP=ambulatory glucose profile
AU70=area under 70 mg/dL (3.9 mmol/L)
CG=control grid
CGM=continuous glucose monitor
FOM=figure of merit
GCA=glucose control assessment
Gm=median glucose
Gv=glucose variability
ITS=insulin titration sensitivity
JDRF=a trademark of Juvenile Diabetes Research Foundation; i.e., JDRF International
LGA=low glucose allowance
LLG=likelihood of low glucose
MTT=margin to treat
SMBG=self-monitored blood glucose
TMS=therapy management system
TRP=treatment recommendation point

SUMMARY OF THE INVENTION

Briefly and in general terms, the present invention is directed to a system and method to provide a glucose report based on large amounts of glucose data, the report showing patterns and analyses of those patterns of the glucose history of a patient as a tool for treatment considerations. In accordance with system aspects, there is provided a system for determining glycemic risk based on analysis of glucose data, the system comprising a non-volatile memory in which is stored a glucose data processing program configured to program a processor to analyze received glucose data and from the analysis, produce a display, an input at which glucose data is received. a display on which glucose data and analytics thereof may be visually presented, a processor connected with the nonvolatile memory, the input, and the display, the processor being configured to access the memory to load and run in the processor the program to analyze glucose data, wherein the processor is programmed to analyze the received glucose data to determine an estimate of a hypoglycemia measure, further analyze the received glucose data to determine a measure of a central tendency of glucose data median and a measure of the spread of glucose data from the central tendency, control the display to visually present differences of glucose in comparison to a central tendency of glucose data, and control the display to visually present a glucose control measure that includes an assessment of the glucose data in the categories of likelihood of low glucose, median glucose, and variability of glucose below the median with visual indicators conveying high, moderate, and low about each category.

In accordance with more detailed aspects, the processor is programmed to determine a glucose median as the central tendency. The processor is programmed to determine the variability of glucose data about the central tendency. The processor is programmed to control the display to visually present percentiles of glucose data in comparison to a median glucose level.

In accordance with method aspects, there is provided a method for determining glycemic risk based on analysis of glucose data, the method comprising storing in a non-volatile memory a glucose data processing program configured to program a processor to analyze received glucose data and from the analysis, produce a display, receiving glucose data, accessing the non-volatile memory and running the glucose data processing program, analyzing the received glucose data to determine an estimate of a hypoglycemia measure, analyzing the received glucose data to determine a central tendency of the data, analyzing the received glucose data to determine a spread of the data from the central tendency, control a display to visually present differences of the glucose in comparison to the central tendency of the glucose data, and controlling a display to visually present a glucose control measure that includes an assessment of the glucose data in the categories of likelihood of low glucose, median glucose, and variability of glucose below the median with visual indicators conveying high, moderate, and low about each category.

In more detailed method aspects, the step of analyzing received glucose data to determine a central tendency comprises determining the median of the data. The step of analyzing received glucose data to determine a spread of the glucose data comprises determining variability of glucose data from the central tendency. The step of visually presenting differences comprises visually presenting percentiles of glucose in comparison to the central tendency.

In yet other aspects, the steps of visually presenting central tendency and spread and differences comprise determining a median of the glucose data, determining variability of the glucose data from the median, and visually presenting differences of the glucose data from the median in percentiles of glucose in comparison to the median.

The features and advantages of the invention will be more readily understood from the following detailed description that should be read in conjunction with the accompanying drawings.

BRIEF DESCRIPTION OF THE DRAWINGS

FIGS. 4A through 4D present further AGP plots and assessments.

FIG. 7 shows an application of the data management in accordance with aspects of the invention to achieve glucose control;

FIG. 8 presents safety performance of LLG and $P_{10}$ methods: Rate of incorrect "Green" indicators when AU70 exceeds the criteria;

FIG. 9 presents sensitivity performance of LLG and $P_{10}$ methods: Rate of correct "Red" indicators when AU70 exceeds the criterion.

FIG. 10 presents a correlation among colors, meanings, and drawings symbols.

FIG. 24 presents recommendations tailored to current treatment;

FIGS. 49A, 40B, 49C, 49D, 49E, and 49F are plots of glycemia risk;

FIGS. 55A and 55B show an embodiment of guidance output; and

DETAILED DESCRIPTION OF EMBODIMENTS

Figure 1:
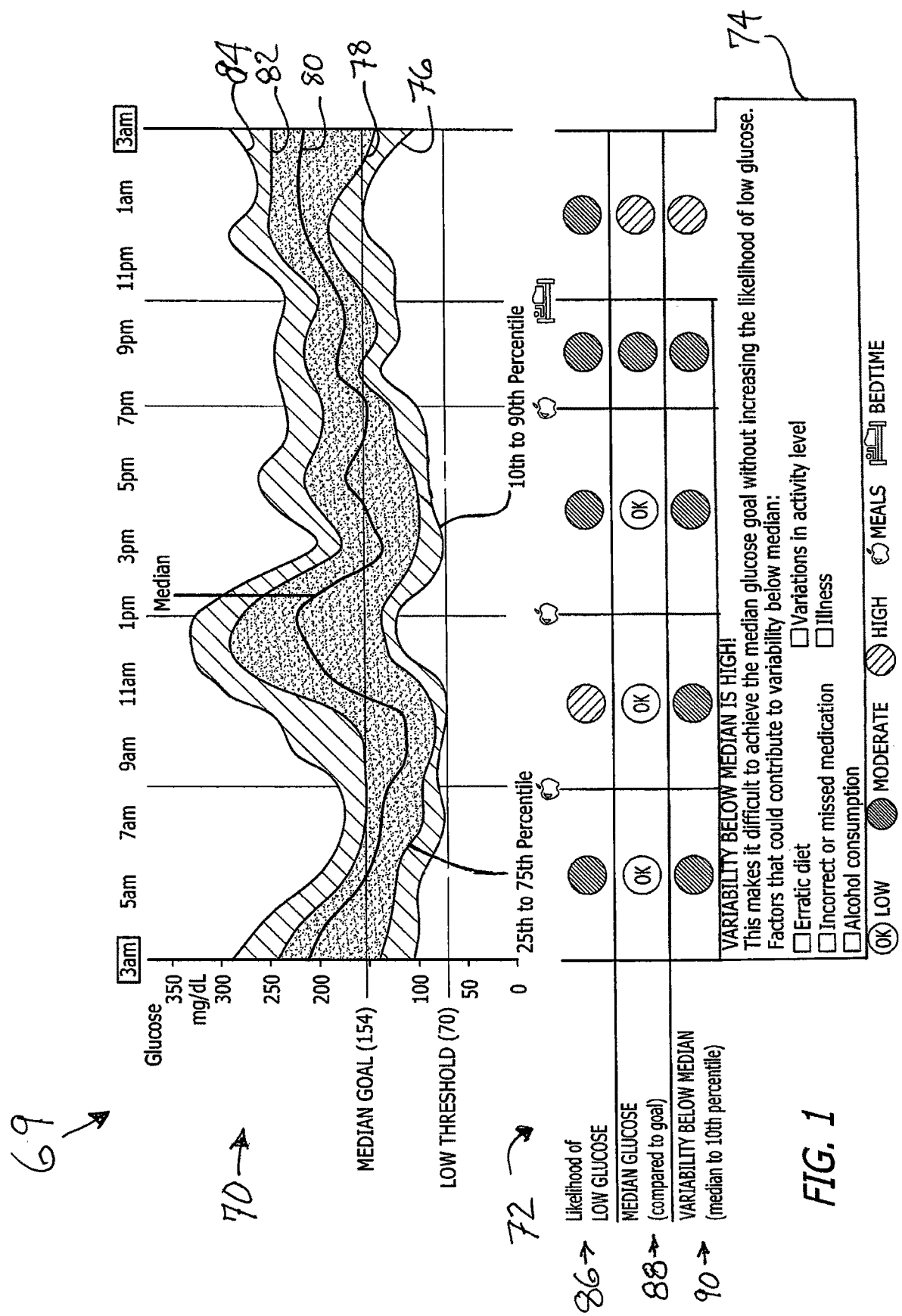
FIG. 1 shows an Ambulatory Glucose ("AGP") plot and Glucose Control Assessment and indicators.
Figure 2A:
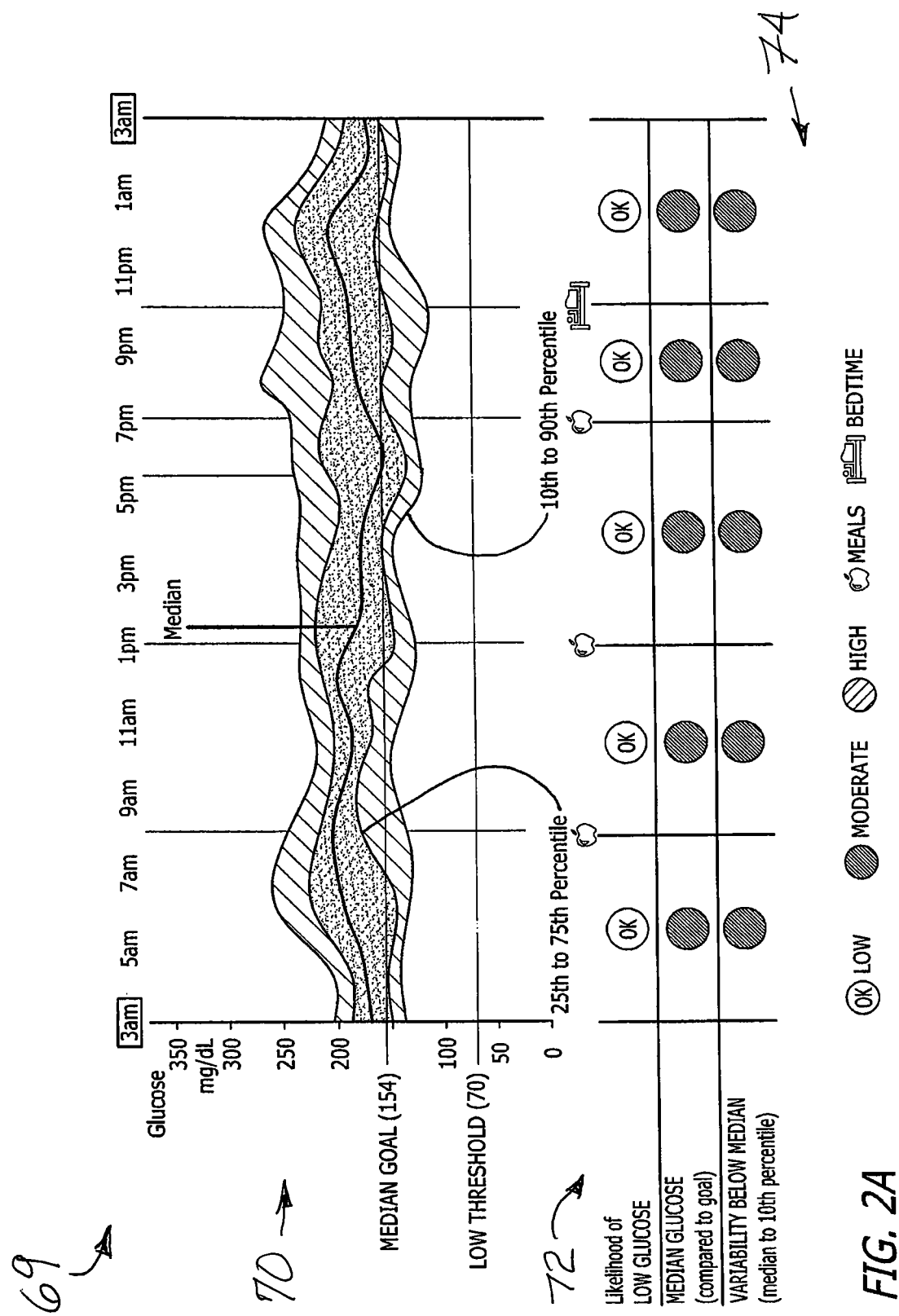
FIG. 2A-2D show additional AGP plots and glucose control assessments with indicators for patient examples from JDRF-CGM trial with laboratory A1C=7.6% to 7.7% measured at time of sensor wear.
Figure 2B:
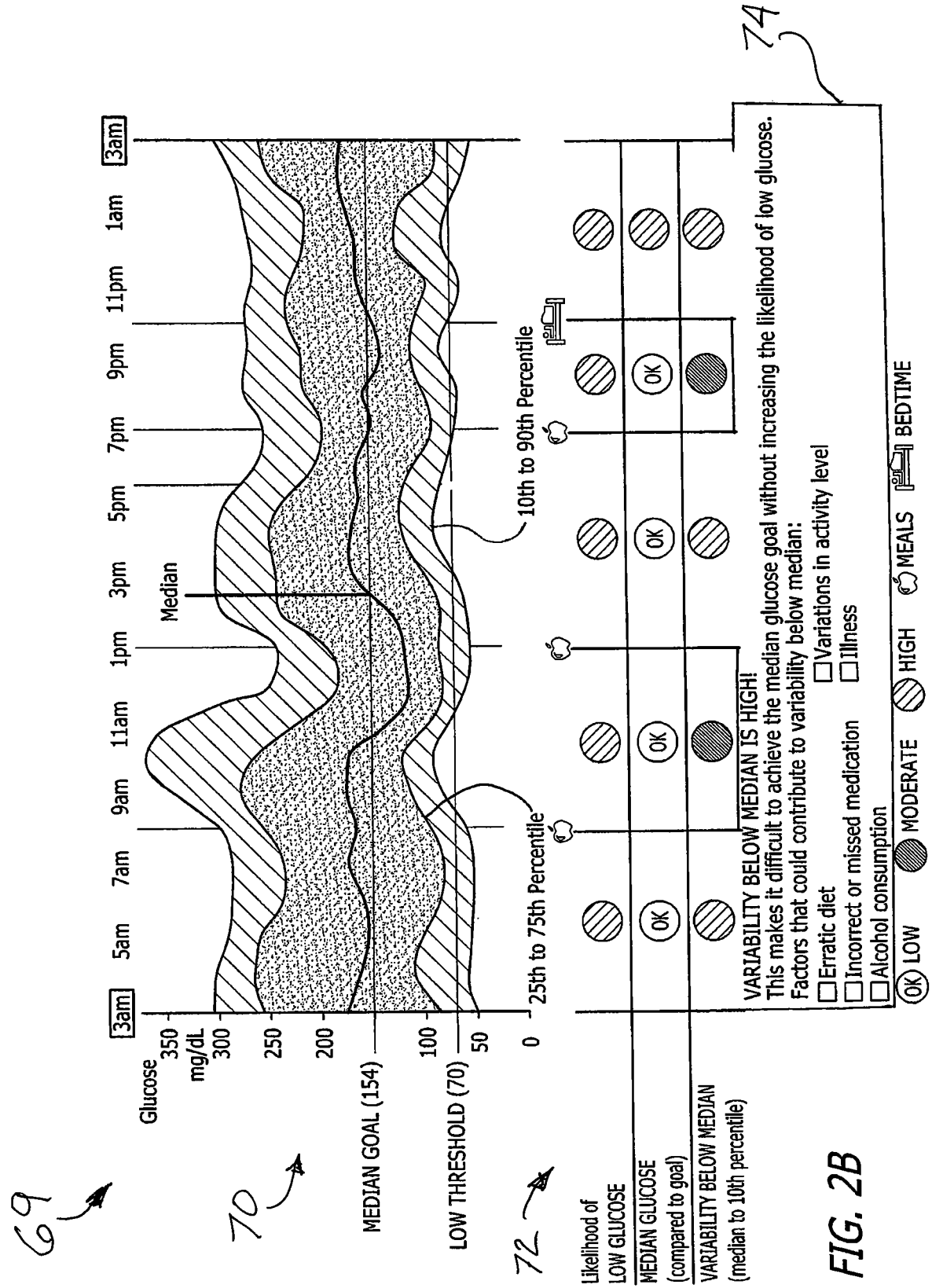
Figure 2C:
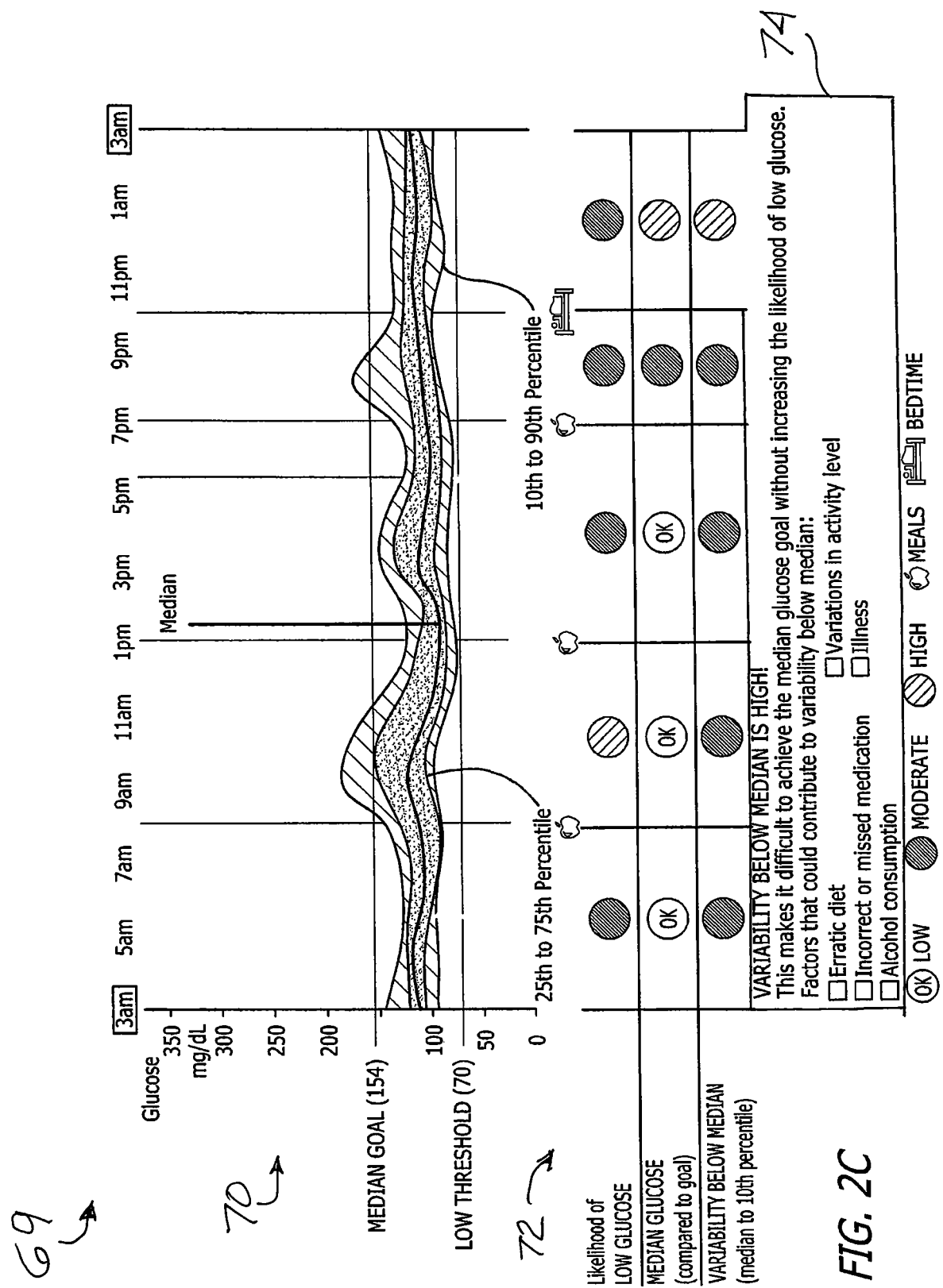
Figure 2D:
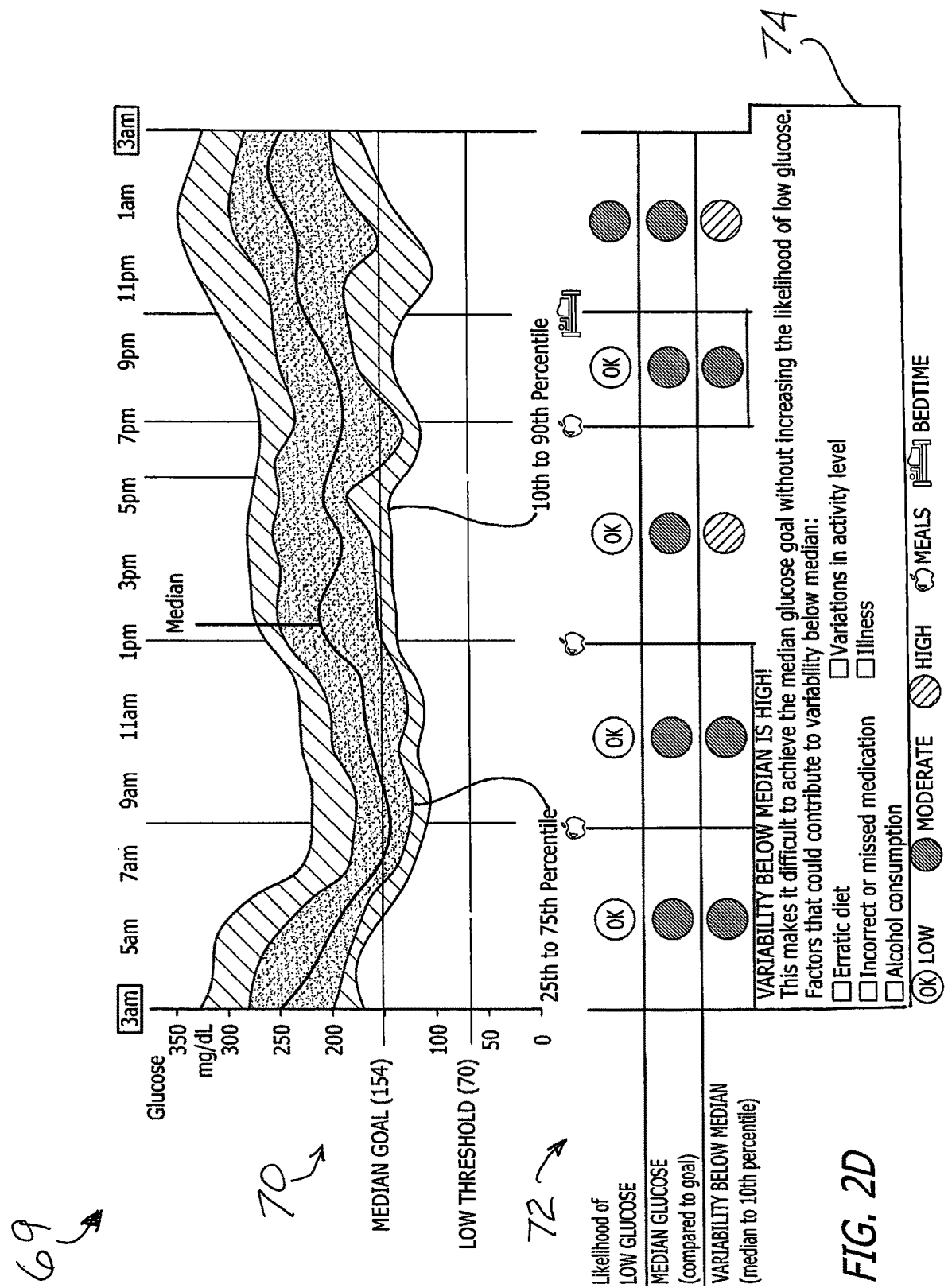
Figure 4A:
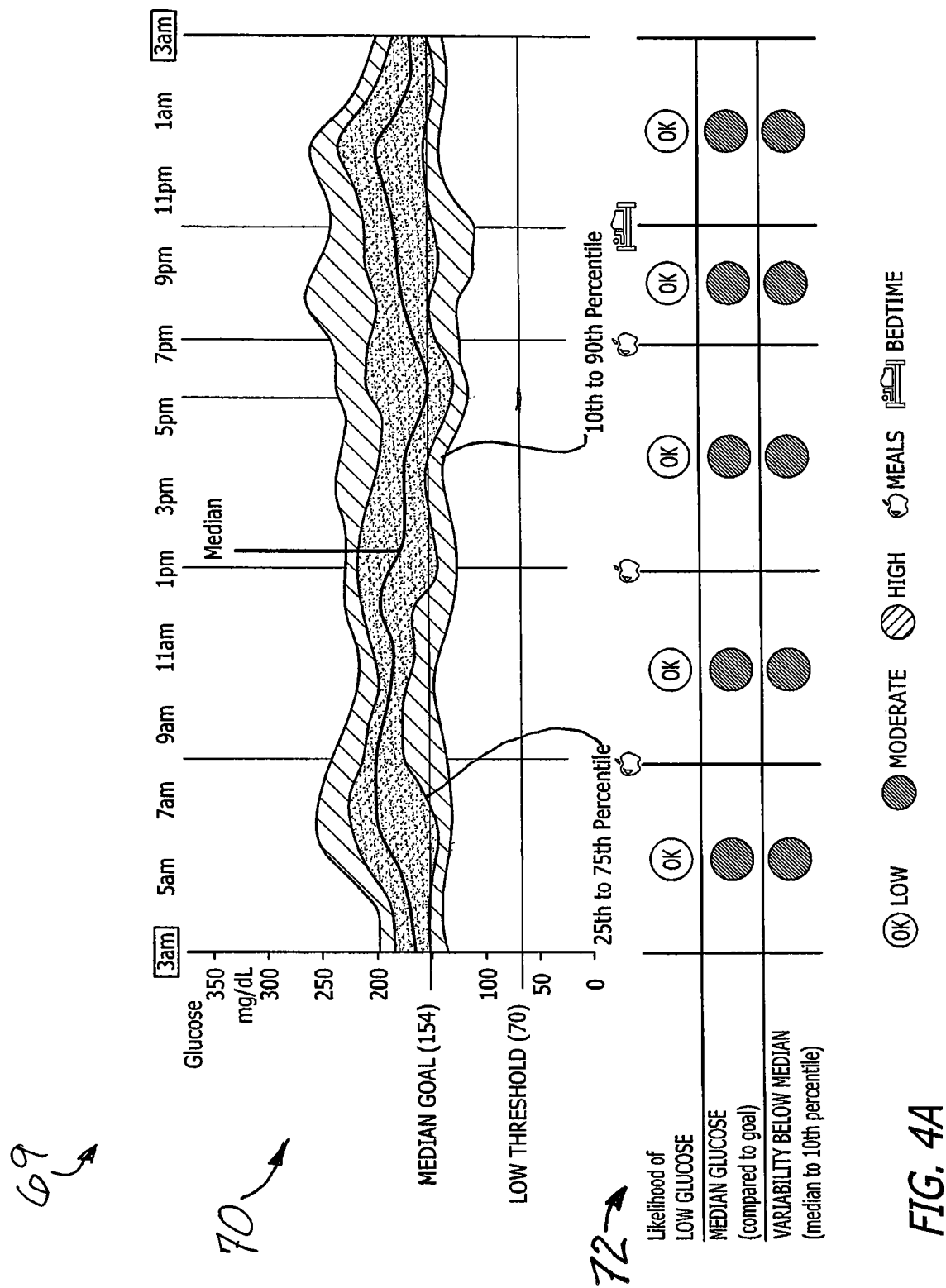
Figure 4C:
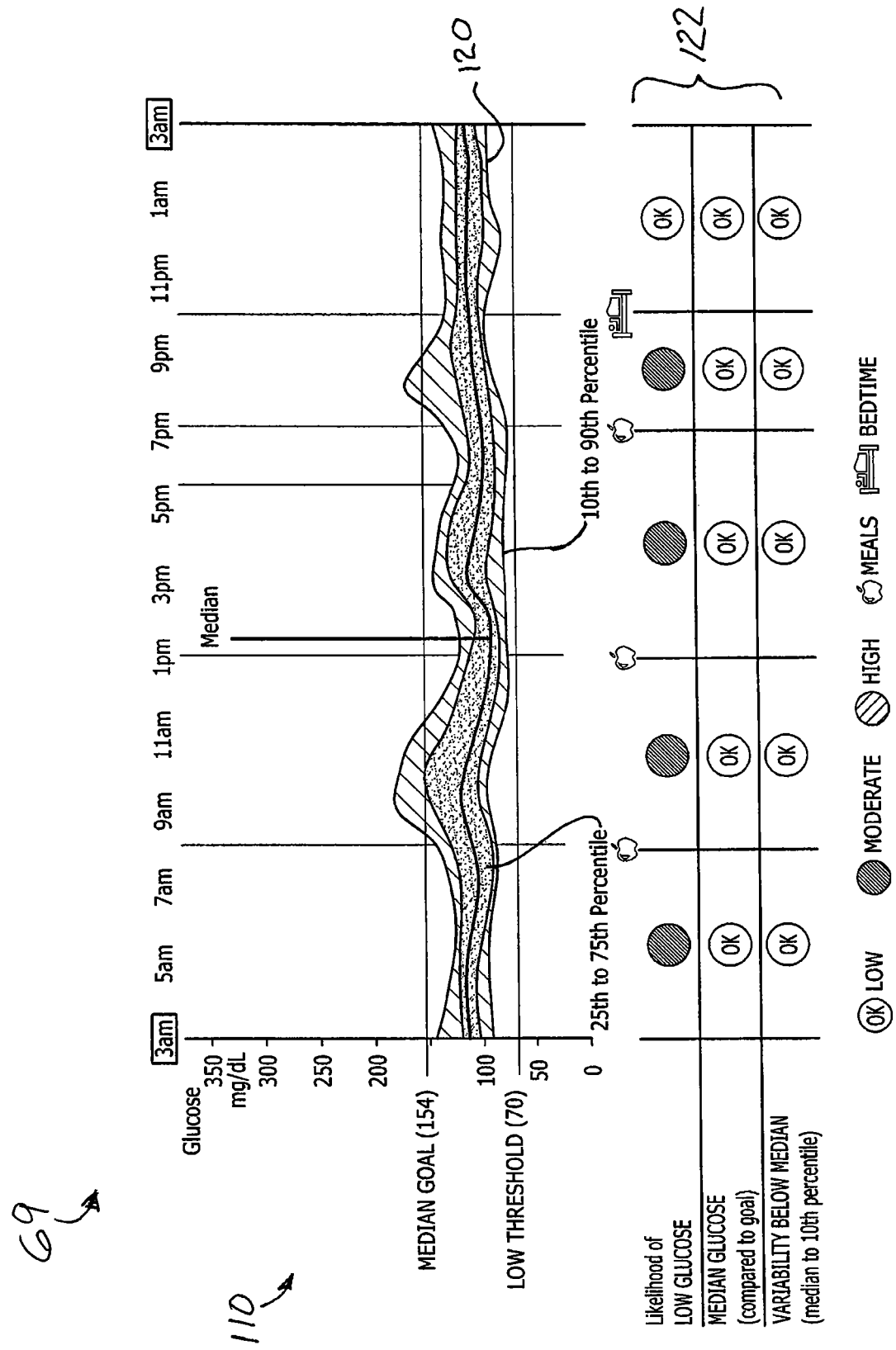
Figure 4D:
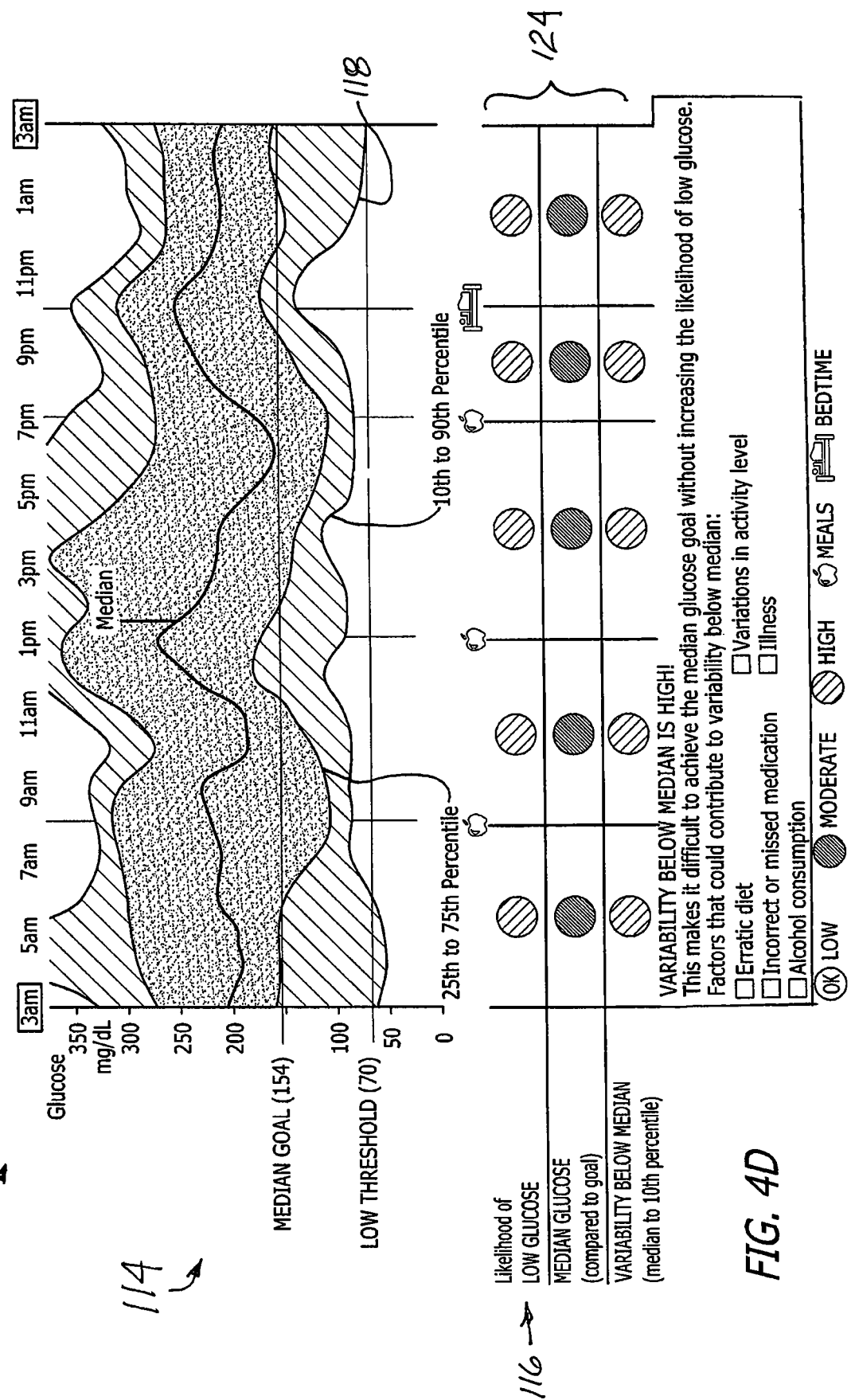

Referring now in more detail to the exemplary drawings for purposes of illustrating embodiments of the invention, wherein like reference numerals designate corresponding or like elements among the several views, there is shown in FIG. 1 a glucose-based report, referred to herein as the Insights report 69, having the three components of an Ambulatory Glucose Profile ("AGP") plot 70, a Glucose Control Assessment ("GCA") 72, and indicators for high glucose variability 74. The indicators may be in color, preferably green, yellow, and red, where green indicates a "low" level, yellow indicates a "moderate" level, and red indicates a "high" level of variability. In the black and white figures of FIGS. 1, 2A-2D, and 4A-4D, the levels are shown by circles with slashes or the letters "OK." Translation of the circles to color is presented in FIG. 10 for one embodiment. In the case of the indicators for Variability Below Median 74, the indicators are linked to the "variability below median" cells when the cells indicate a "HIGH" level. A box appears around the indicators and the HIGH level cells as shown in FIGS. 1 and 2B as examples. When none of the cells of the "variability below median" row indicate "HIGH," the indicator box does not appear, as seen in FIGS. 2A, 4A, and 4C. In place of a box, a common color may be used. That is, the same fill color may be used for the cells of the Variability Below Median row indicating HIGH as the fill color for the indicators box (see FIG. 1). Other approaches may also be used.

In particular, a mathematically-based system and method has been used that exploits the relationship between glucose median, glucose variability, and hypoglycemic risk to prepare a report, and can be implemented in computer software. From this relationship, the glucose pattern report referred to as the "Insights" report 69 is produced. Examining the AGP 70, the GCA 72, and the indicators 74 provides a good reference for the decision-making process in treatment.

The Insights report 69 is made up of the three primary components mentioned above; i.e., the Ambulatory Glucose Profile ("AGP") plot 70, the Glucose Control Assessment ("GCA") 72, and the indicators for high glucose variability 74, and is divided into time-of-day periods in FIG. 1, and can be adjusted according to a person's typical routine. The variety of Insights reports for similar people with the same A1C is shown in FIGS. 2A-2D thus demonstrating the large increase in data and analysis presented about each of those people by the Insights report. The AGP graph 70 displays the hourly $10^{th}$ (76), $25^{th}$ (78), 50th (median) (80), $75^{th}$ (82), and 90th (84) percentiles of glucose readings, presented over the "typical" day based on all days within the selected timeframe. It will be noted that the AGP plot includes two horizontal lines. These are a "median goal" line of 154 in this embodiment, and a low glucose line of 70.

The first GCA 72 measure, "Likelihood of Low Glucose" ("LLG") 86, is the probability that low glucose values have exceeded an allowable, user-defined threshold. The second measure, "Median Glucose (Compared to Goal)" 88, is an indication of when the median glucose has exceeded the individual's Median Goal setting. The third measure, "Variability below Median (Median to $10^{th}$ Percentile)" (90), is a measure of the spread of glucose data below the median. It is calculated as the difference between the 50th and 10th percentile glucose readings for the time period. It is important to note that when variability below the median is high, it is difficult to achieve the median goal without increasing the Likelihood of Low Glucose (86). Therefore, factors causing the elevated glucose variability must be addressed before insulin doses are increased, otherwise there would be an increased risk for low glucose. The Insights report 69 also outlines factors that could contribute to HIGH variability below the median including "Erratic diet," "Incorrect or missed medication," "Alcohol consumption," "Variations in activity level," or "Illness," and that need to be reviewed and addressed by the health care professional in his/her counseling of the patient. The GCA indicators are low, moderate, or high based on the criteria 92 shown in FIG. 3.

The Median Goal parameter (FIG. 3) sets the glucose level for which Median Glucose is reported as Low, Moderate, or High. The median glucose provides a useful measure because of its strong correlation with A1C. The overall glycemic management goal is to reduce median glucose levels below the goal while minimizing the LLG, as this should result in A1C and hypoglycemia exposure goals being met.

The Low Glucose Allowance parameter (FIG. 3) sets the threshold for which LLG is reported as Low, Moderate, or High. The setting options are Small, Medium, or Large. Increasing this parameter allows more glucose readings below 70 mg/dL (3.9 mmol/L) before causing the LLG to go from Low to Moderate or High. The allowance was based on both the frequency and value of low readings. The Insights report 69 is designed to allow the clinician to adjust the allowance setting according to the clinical scenario. For example, the allowance may be decreased for someone who is elderly or has hypoglycemia unawareness. Alternatively, the allowance may be increased for a pregnant woman trying to maintain tight glucose control.

In addition, the times of Daily Events (FIG. 1, area of AGP 70) defines the periods during the day used to analyze the GCA 72. The user can set the typical times for Breakfast, Lunch, Dinner, (apple icon) and Bedtime (person in bed icon). These times correspond to daily events that are clinically relevant to diabetes patients whose insulin therapy is related to eating and sleeping events. The result is three daytime periods and two overnight periods, with default time boundaries of 3 am, 8 am, 12 pm, 6 pm and 10 pm. Therefore, a total of fifteen indicators are displayed in the GCA 72 to support review of the AGP 70.

The supporting role that the GCA 72 provides is shown for four patients, using data publicly-available from the JDRF Continuous Glucose Monitoring Clinical Trial (JDRF-CGM trial) dataset in FIGS. 4A-4D. The first patient, who is shown in FIG. 4A, had minimal likelihood of low glucose across the day, as the median and $10^{th}$ percentile line were substantially elevated relative to the median goal (Median Goal (154)) and the hypoglycemic boundary (Low Threshold (70), respectively. In this case, the GCA conformed to the visual interpretation of the AGP 70, indicating that glucose levels could be lowered safely with little risk of inducing hypoglycemia.

The second AGP 100 shown in FIG. 4B shows substantial hypoglycemia across the day, as the 10th percentile 76 was nearly always below 70 mg/dL. The GCA 102 also supported rapid AGP interpretation that hypoglycemia was a clinical priority to be urgently addressed as shown by the indicator of "High" across the entire day.

The third AGP 110 (FIG. 4C) illustrates excellent control by achieving low exposure to both hyper- and hypoglycemia. Given the small margin of error into the hypoglycemia range, however, there needs to be continual vigilance and awareness of the presence of hypoglycemia. The fourth AGP 114 (FIG. 4D) illustrates how the LLG 116 indicated "Red" (wide cross-hatched circles), despite having similar hourly 10th percentile 118 values to FIG. 4C. This patient would need additional caution due to the presence of the elevated variability below the median and the potential to induce further hypoglycemia, especially if the elevated median values were to be addressed by more insulin coverage. In FIG. 4C the $10^{th}$ percentile 120 values of 80 to 90 mg/dL were acceptable, whereas, in FIG. 4D they indicated an added risk because of the higher median values and the increased risk for hypoglycemia associated with therapeutic intervention(s) to reduce the median closer to goal. The GCA indicators 122 and 124 encapsulate this clinical logic by linking the dimensions of hypoglycemia, median glucose levels, and glucose variability below the median.

Figure 4E:
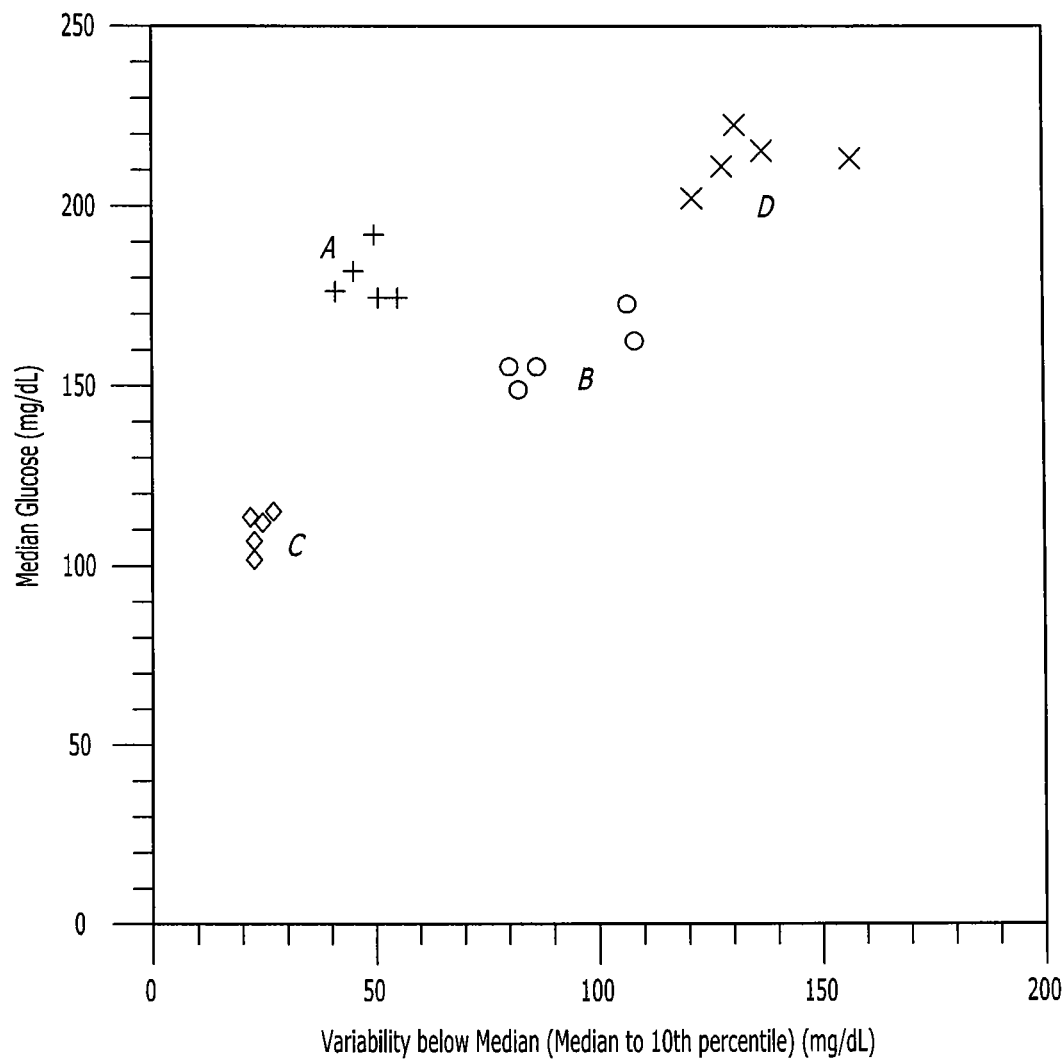
FIG. 4E is a representation of the summary statistics for central tendency and variability of the glucose distributions for each time period for each patient.

The grouping of the five median-variability value pairs for these patient examples are shown in FIG. 4E. It can be intuited that patient A (FIG. 4A) would have the least likelihood of low glucose, as the median is high and the variability is low. In this region of the plot, none of the $10^{th}$ percentile values would be lower than 100 mg/dL. Conversely, as median values decrease (patient C) (FIG. 4C), variability increases (patient D) (FIG. 4D), or both occur (patient B) (FIG. 4B), there would be an increased likelihood of low glucose for these patients relative to patient A. This linkage between median, variability, and low glucose is utilized by the method to create the LLG indicator. In the next section, the relationships in FIG. 4E will be discussed in terms of the Control Grid, a construct that underlies the GCA.

To define the decision support method, there are two important aspects that need to be considered for proper glycemic management: (1) reducing overall glucose levels; and (2) reducing glucose variability in order to minimize inducing hypoglycemia as glucose levels are lowered. The key to this framework is to consider that for a period of time each patient has a population of glucose readings that can be described as a stationary statistical distribution. The Gamma distribution is an appropriate and convenient model; like glucose values, this distribution does not allow zero or negative values and is skewed toward high glucose values.

For each period of the day, the distribution of glucose values can be characterized by a pair of metrics representing central tendency and variability. The median ($50^{th}$ percentile, or $P_{50}$) was chosen as the metric for central tendency, and the difference between the median and $10^{th}$ percentile ($P_{10}$) as the metric for variability, also defined as the lower interdecile range, $P_{10}$ to $P_{50}$, and named "Variability below Median" on the Insights report 69.

Percentile metrics were favored over other common statistics such as mean and standard deviation because of commonality with AGP's 70 use of percentiles, as the GCA 72 is intended to compliment the AGP on the Insights report 69. In addition, percentiles are more robust to outliers that often occur in glucose data. The $P_{10}$ to $P_{50}$ metric was chosen for representing variability instead of other symmetric measures, such as the interquartile ($P_{25}$ to $P_{75}$) or interdecile ($P_{10}$ to $P_{90}$) ranges because it was a better predictor of hypoglycemia risk.

Using this framework, the mathematical relationship between glucose median, glucose variability and LLG can be described. This relationship led to rules that translated glucose data into GCA indicators to provide standardized guidance for treatment decisions.

For the purposes of this method, a hypoglycemia metric was selected that is dependent on both time and magnitude of glucose readings below 70 mg/dL, referred to as AU70 (area under 70 mg/dL). Taking all readings below 70 mg/dL, the AU70 metric is defined as the sum of all differences (70 mg/dL−reading) divided by their total number. The value of the AU70 metric used in generating the Insights report is referred to as the Low Glucose Allowance ("LGA") setting. As described previously, the report has three possible settings defined for LGA (Low, Moderate, or High); each of these configures the algorithm for three different degrees of risk for low glucose.

As mentioned, the key concept underlying the decision support methodology is the relationship between median, variability, and hypoglycemia risk. This is illustrated on the median-variability plots shown in FIGS. 5A to 5C, where the glucose median is on the y-axis and the glucose variability ($P_{10}$ to $P_{50}$) on the x-axis. A point was plotted for each patient for a period of the day (in this example 3 am to 8 am) for two weeks of Navigator® continuous glucose sensor (Abbott Diabetes Care, Alameda, CA) continuous glucose measurements. The point is an open circle (red) if the AU70 metric exceeded the LGA; otherwise, the point is a solid circle (blue). The figures show a good separation between the two populations of points, even as the LGA is varied.

Figures 5A, 5B, 5C:
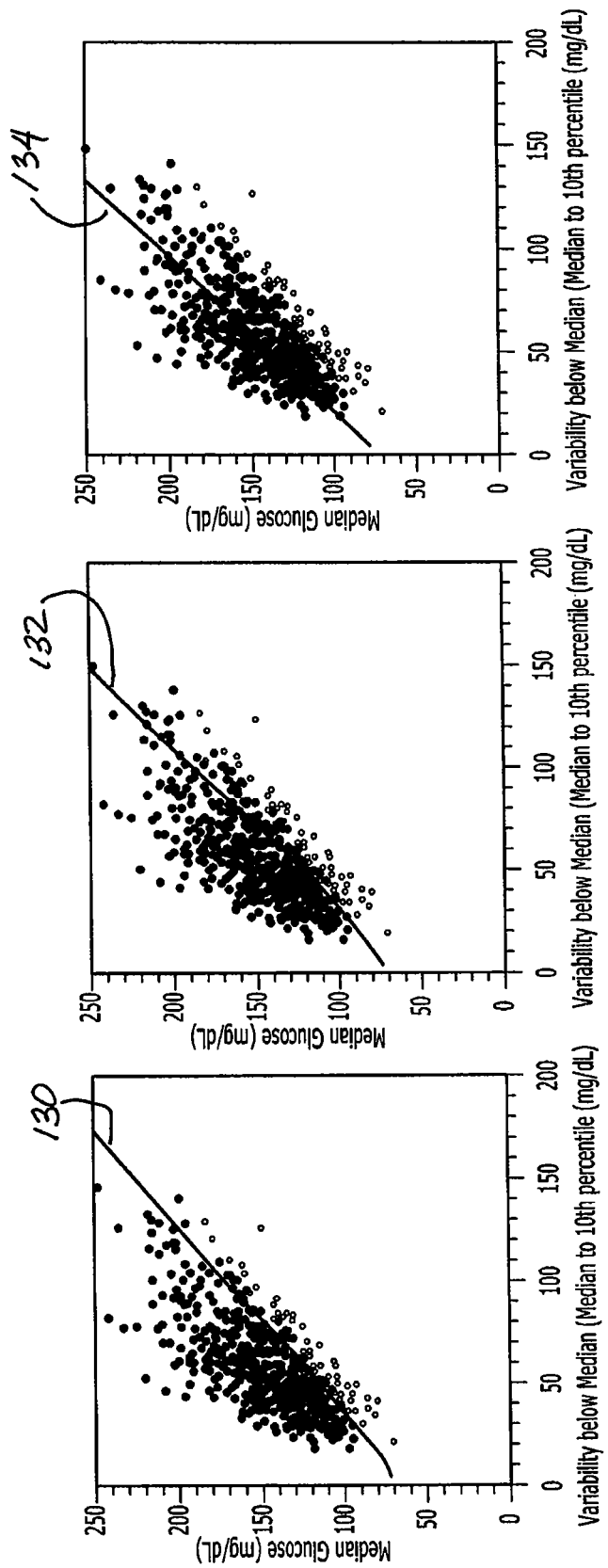
FIGS. 5A-5C show the likelihood of low glucose ("LLG") performance at Low Glucose Allowance (LGA) settings of large (A), medium (B) and small (C)

The Gamma distribution model of the glucose data can be used, along with the AU70 definition of hypoglycemia, to theoretically derive a boundary between these two populations. This boundary, referred to here as the "High Risk Curve" (130 in FIG. 5A, 132 in FIG. 5B, and 134 in FIG. 5C), is made up of points on the median-variability plot that correspond to the same AU70 value, and can be found using the equation for the Gamma distribution varied over all possible median and variability values to find those pairs where the area of the distribution below 70 mg/dL is equal to the AU70 setting. Three High Risk Curves, one for each LGA setting (FIG. 5A has a large "low glucose allowance" (LGA), FIG. 5B has a medium LGA, and FIG. 5C has a small LGA), have been determined for use with the Insights report 69. FIGS. 5A to 5C show how well these curves separated the two point populations. The LGA settings were determined from a large population of median-variability points, and selected such that approximately 10%, 30%, and 50% of the LLG indicators would be below the High Risk Curve for the Large, Medium, and Small settings, respectively.

Figure 6:
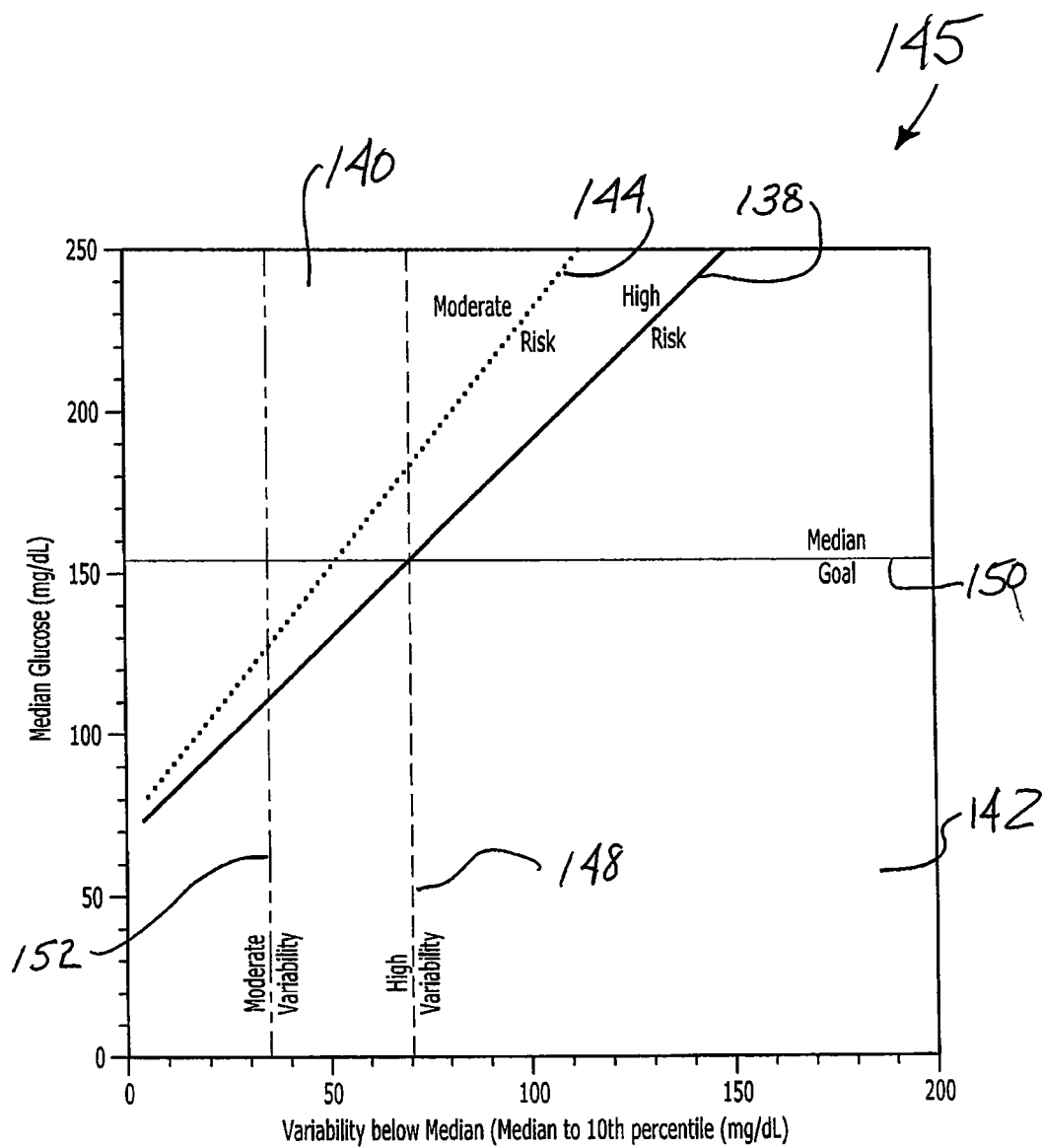
FIG. 6 provides a Control Grid with High Risk Curve for the Medium Low Glucose Allowance setting, Moderate Risk Curve for daytime with 14 days of CGM, Median Goal=154 mg/dL.

The High Risk Curve 138 of FIG. 6 can be used to divide the median-variability plot into two zones: a low hypoglycemia risk zone 140 above the curve, and a high hypoglycemia risk zone 142 below the curve (FIG. 6). This concept of zones can be extended to convert the median-variability plot into a so-called Control Grid ("CG") 145. Using a patient's set of CGM data, a Control Grid and point on it can be calculated for each of the five time-of-day periods (FIG. 6).

The High Risk Curve divides the "high" (red) and "moderate" (yellow) LLG zones, and a Moderate Risk Curve divides the "moderate" and "low" (green) LLG zones. The Moderate Risk Curve accounts for uncertainty in the LLG indicator as a result of uncertainty in the values. The uncertainty of the median and variability ($P_{10}$ to $P_{50}$) are affected by the number of data samples available and the time-varying nature of these values. The Moderate Risk Curve 144 was determined empirically for each time-of-day period and LGA setting, such that patients with points in the low risk zone during one two-week period have less than 10% chance, with 95% certainty, of landing in the high risk zone during the subsequent two-week period. The Moderate Risk Curve is implemented as a 60-element look-up table along the dimensions of LGA (3 levels), daytime or nighttime (2 levels), and amount of glucose measurements (10 levels). For example, the Moderate Risk Curves for 14 days of CGM for a 5-hour period of the day have AU70 values of 0.03, 0.17, and 0.53 for daytime periods for the small, medium and large LGA settings respectively, and 0.02, 0.09, and 0.39 for nighttime periods.

Figure 3:
FIG. 3. Criteria for determining low, moderate, and high indicators in the Glucose control Assessment (GCA)

The criteria for the Median Glucose indicator described in FIG. 3 can be represented visually as a horizontal line at the Median Goal setting. This boundary divides "Green" from "Yellow" indicators, with "Yellow" indicators becoming "Red" if the median value for that time period is both 20% and 40 mg/dL above the 24-hour median glucose value.

The boundary for the Variability below Median indicator described in FIG. 3 can also be represented as vertical lines in FIG. 6. The High Variability line 148 is located at the intersection of the Median Goal 150 and the High Risk Curve 138. This defines high variability to be such that the median glucose cannot be reduced below the median goal without indicating high LLG. The Moderate Variability line 152 is fixed at 35 mg/dL (1.9 mmol/L); this value was determined by review of CGM studies in people without diabetes.

The Control Grid 145 identifies different zones according to glycemic conditions of clinical relevance that indicate the direction of therapy modification. The significance for therapy decision support is that the zones provided on the control grid can be the basis for mapping glucose data for a period of the patient's day into therapy suggestions. Specifically, a point on the Control Grid directly maps to a column on the GCA 160 (FIG. 7).

The table of FIG. 7 illustrates how the GCA indicators 162 can be applied to achieve glucose control. See FIG. 10 for the correlation between colors, meanings, and symbols used in the drawings. For example, in the first row depicting two "OK" green signals 164, there is a very low risk of having hypoglycemic episodes, thus no changes are needed as the patient has met the glucose goals of managing both hypo- and hyperglycemic exposure. A possible action that could be taken is to consider lowering the glucose goal if the patient is not at the A1C target. The fourth row 166 of FIG. 7 illustrates scenarios with either moderate, densely shaded circle (yellow), or high, sparsely shaded circle (red), risk for LLG. For these patients it would be important to address self-care behaviors to reduce glucose variability and the risk for hypoglycemia. If necessary, insulin doses may need to be adjusted to reduce hypoglycemic risk.

The preceding concepts were applied retrospectively to JDRF-CGM clinical trial data to establish hypoglycemia assessment and forecasting performance. CGM values for all participants were divided into 4-week segments starting at the first available sensor reading. Each four-week period was split into 2 two-week periods (1 and 2), and each period was split into 5 time-of-day intervals (3 am-8 am, 8 am-12 pm, 12 pm-6 pm, 6 pm-10 pm, 10 pm-3 am). The value of AU70 was calculated for all periods and intervals. These values were taken to be true, and were compared with the results from the LLG method and a method based on the $P_{10}$ value of a time-of-day interval, using data from period 1 only. Note that the $P_{10}$ method can be estimated directly from the AGP.

For purposes of analysis, any value of AU70 above 0.83 was deemed excessive, and any value below 0.83 was acceptable. The comparison of either method with the AU70 of period 1 was called "in-sample," while the comparison with the AU70 of period 2 was called "out-of-sample." The $P_{10}$ forecast was "Green" if the 10th percentile was above an upper limit, "Red" if below a lower limit. A variety of lower and upper limit values were evaluated. The combinations of in- and out-of-sample comparisons were tabulated to compare the performance of the LLG and $P_{10}$ methods.

There were 13,932 evaluable comparisons between low glucose risk forecasts in Period 1 and actual measured low glucose exposure in Period 2.

The most important safety performance criterion is minimizing the rate of missed detections of excessive hypoglycemic risk. This corresponds to "Green" indicators when there is excessive AU70 (FIG. 8), as this is a false indicator that it would be safe to increase insulin to lower glucose when it would likely induce additional hypoglycemia. The LLG method had an in-sample rate of 0.5% and out-of-sample rate of 5.4% for incorrect "Green" indicators across all evaluated periods. These were better than the P10 method for upper limits up to 110 mg/dL. When evaluated only for the periods with median values 155 mg/dL and higher, the performance of the LLG is even better when compared against the P10 method. This performance when the median glucose is elevated above target is an important performance measure, as it is the situation that would predominately indicate an increase in insulin coverage for that period, thus carries substantial risk of inducing additional hypoglycemia.

In terms of correct detection of excessive AU70, the LLG method has an in-sample rate of 88.3% and an out-of-sample rate of 59.6%. These were as high or higher than the P10 method up to about 80 mg/dL. When evaluated for median ranges above and below 154 mg/dL, the P10 lower limit that matched the performance of the LLG method was different. For the median range above target, the LLG was superior or equivalent up to 90 mg/dL, while for the lower median range, the LLG was superior or equivalent up to 75 mg/dL. See FIG. 9. This illustrates a challenge of using the P10 method, as limits must be varied according to the median range to match the LLG performance. The LLG method did not have this challenge as it was founded on the inter-relationship of the three important dimensions of median glucose, variability, and hypoglycemia.

The trade-offs associated with the dimensions of superior performance of the LLG method included having higher rates of false alarms (incorrect "Red" indicators) and lower rates of true negatives (correct "Green" indicators). The incorrect "Red" indicators for the LLG method was 16.4% in-sample and 23.7% out-of-sample, which was approximately equivalent to the P10 method with a lower limit of 80 mg/dL for all median levels. However, the LLG method was superior for lower median values (<154), where an incorrect Red may lead to a reduction in insulin coverage. The LLG method had incorrect "Red" indicators of 20.9% in-sample and 30.7% out-of-sample, which was better than 30.5% in-sample and 38.8% out-of-sample for the P10 method with a lower limit of 80 mg/dL.

Taking all of these dimensions of performance together, the LLG method stood apart from the P10-based methods in that no single pair of limits could match the performance of the LLG, in particular when correctly assessing risks of hypoglycemia when the median glucose level was above target.

Diabetes clinicians traditionally have had to make treatment decisions based on infrequent glucose readings that may not adequately reflect a patient's glycemic profile. Continuous glucose monitoring provides an abundance of information about daily glucose patterns. However, the time required to review this vast amount of data can strain clinician efficiency. The Insights report 69 was designed to support diabetes clinicians in quickly understanding the patient's overall glycemic condition and facilitating safe and effective therapy modifications. From the standpoint of insulin-based treatments, this method provides standardized guidance for medication adjustment (increase, decrease or maintain), and highlights the necessity to address self-care behaviors in order to reduce glucose variability that is elevated to the point that it limits managing both hyperglycemia and hypoglycemia.

The key to this framework was to consider that for a period of time each patient had a population of glucose readings that could be described as a statistical distribution. A fundamental insight of this model was the defining of the boundaries between Low, Moderate, and High LLG based on the gamma distribution. A benefit of this reporting model is that the decision support algorithm was designed to allow the clinician to adjust the Low Glucose Allowance setting depending on the aggressiveness of treatment, allowing for more or less conservative report indicators.

Computerized treatment algorithms using CGM data have been developed in an effort to use the abundant information in a clinically meaningful manner. In a two-month study of 22 insulin-dependent subjects using daily capture of SMBG and a predictive glucose model, A reduction in rates of hypoglycemia by nine-fold and insulin therapy by −9 U/day was reported. Computerized glucose programs have also been used for educational purposes to allow patients to gain insight into the effect of insulin dosage adjustments, diet changes, and exercise on glucose levels. The algorithm "Librae," a computerized diabetes simulator in diary format developed as an educational tool for patients, correlated well with the CGM data, however there were also some clinically unacceptable errors at extremes of blood glucose levels. The programmatic model described herein differs from other models in the robustness of the glycemic forecast comparisons that were used reduce missed detections of excessive hypoglycemia. Two key advances of the LLG method are its sensitivity in detecting incorrect green and correct red forecasts for improved predictive capabilities when compared with the methods relying solely on the lines of the AGP. The predictive aspect of the proposed algorithm provides clinicians with targeted areas to focus on, such as high risk for hypoglycemia and variability, which in turns aids in determining how aggressive corresponding treatment should be. The proposed model also displays potential reasons for glycemic variability that can be addressed with the patient, and used for patient education about lifestyle behaviors.

There were some challenges associated with designing the programmatic model presented here. For instance, each of the three High Risk Curves was associated with a single constant value of the hypoglycemia metric, selected to be AU70. Because there is no established guidance on how much hypoglycemia area is "excessive" or "problematic", the AU70 settings had to be empirically derived. In a patient exam using the Insights report 69, the clinician would be able to further probe the hypoglycemic experience and assess the need for intervention. Understanding the alignment between these AU70 settings and clinical diabetes management needs further investigation, particularly for different patient profiles of diabetes type, age, duration of diabetes, and presence of comorbidities. There are likely instances where more or less hypoglycemia are acceptable based on the needs of the patient. For example, an elderly patient who lives alone may need to be more vigilant about the possibility of a severe hypoglycemic episode compared with a younger individual who can recognize hypoglycemic symptoms, is trained to treat hypoglycemia, and is using CGM with low glucose alarms. This established the clinical need to have multiple settings (large, medium, and small) of LGA based on the characteristics of the patient, but further work is needed to understand how to clinically apply and validate the available settings.

The vulnerability to low glucose can be higher overnight while sleeping because of impaired hypoglycemia symptoms. This motivated the decision to have empirically derived the Moderate Risk Curve for each time period. This derivation met expectations of resulting in more conservative settings overnight compared to daytime. Fear of hypoglycemia has been reported by pediatric and adult populations, as well as by caregivers, and is associated with increased frequency of severe hypoglycemia. Moreover, fear of hypoglycemia may contribute to poor glycemic control, weight gain, and emotional distress. The use of the programmatic report described here, which highlights time periods of increased risk for hypoglycemia, may be a valuable tool for overcoming fear of hypoglycemia. Further research in the clinical population is needed to investigate this potential benefit.

The Insights report 69 provides a model for assessment of high risk times of the day that require therapeutic intervention, and provides more detail than A1C alone. As shown in FIGS. 2A-2D, patients may present with the same A1C value, yet have very different daily glucose patterns. The Insights report offers pattern recognition capability that highlights areas of variability. A key feature of this report is the suggestions for topics to discuss with the patient, which could aid in trouble-shooting potential reasons for increased glucose variability that may be associated with elevated hypoglycemia risk.

It has been noted that 27 non-insulin using patients who received behavioral intervention consisting of review of CGM data and "role model" data about exercise benefits showed greater improvements in A1C, moderate activity, systolic blood pressure, and body mass index when compared with the control group who received generic education and advice. These results, although in a small population of non-insulin patients, show the benefits of glucose reports in patient education and treatment.

The analyses presented here have several limitations. For the LLG versus $P_{10}$ safety and performance analysis, the time-periods of the day used in the analysis were at fixed times of the day, not individualized to actual daily activities of patients, and may therefore bias the results. The analysis does not account for the interplay between time periods when managing glucose levels. Furthermore, this was a retrospective analysis and was not incorporated into a glucose-control intervention. The performance may vary under the conditions of using the hypoglycemia forecasts to support clinical treatment decisions. Finally, there was no accounting for the repeated assessments on the same study participants over the longitudinal course of the study.

Methods for Identifying Diabetes Self-Care Behaviors of Therapeutic Importance

Frequent glucose monitoring, for example supplied by sensor-based interstitial measurement, has expanded the possibility of summarizing and reducing the measurements into metrics of interest for diabetes management. To date, there has been an abundance of data reduction methods proposed (averages, medians, percentiles, variability metrics, risk metrics, etc.); however these methods have failed to enlighten a majority of care providers and patients. Many patients and care providers feel overwhelmed and burdened by an excess of data that provides no additional insight or knowledge.

The current invention leverages clinically-informed algorithms to search the data to reveal insights about the glucose control and self-care behaviors performed by the patient. These insights can then direct the care provider and patient to therapeutic and educational methods to improve diabetes self-care behaviors, improve glycemic control and reduce risks of short- and long-term complications associated with diabetes.

The invention will be described with sensor-derived glucose measurements (multiple measurements per hour), but has the potential to also be applied to frequent (four or more per day) strip-based glucose measurements.

The current invention uses clinically-informed algorithms to search glucose data acquired for an individual patient to reveal diabetes self-care behaviors. There are five main components to the operation of the invention: 1) defining "episodes" of interest, either daily activities or glucose-derived, 2) selecting a "kernel" episode for the search routine, 3) constructing "episode chains" of a sequence of episodes (including the kernel episode) and logical rules for the inclusion or exclusion of episodes in close proximity to the kernel, 4) associating one or more episode chains with a diabetes self-care behavior, and 5) displaying the findings of the search algorithms.

Episodes

This invention proposes using episodes related to daily activities (meals, taking medications, exercise) as well as four main classes of glucose-based episodes: High, Low, Rise, Fall. Each of these glucose episodes are defined by thresholds. For each class of glucose episode, several instances (or "flavors") may be defined for use in the search algorithms. For example, two types of "High" glucose episodes may be constructed: "Extreme High" may have entrance/exit thresholds of 240/220 mg/dL and minimum duration of 15 minutes, while a "Moderate High" may have entrance/exit thresholds of 180/160 mg/dL and minimum duration of two hours. In this way, a clinically-informed hierarchy of severity of high glucose may be formed, such as a clinical statement to a patient of: "Try to never go above 240 mg/dL ("Extreme High"), and try to avoid going above 180 for more than two hours ("Moderate High")." In the example shown in Table 1, two activity-based episodes (Meal and Exercise) and five glucose episodes have been defined: "Low (L)", "High (H)", "meal-related Rise (m-R)", "low glucose treatment Rise (1t-R)" and "Fall (F)". In the absence of daily activity records, it is envisioned the search algorithms could be executed on glucose episodes alone.

Kernel Episode Selection

The "episode kernel" is the episode which initiates the search algorithm for each episode chain, and there is only one kernel per chain.

Episode Chain Construction and Search Logic

Using the kernel as the starting point, other episodes before and/or after are defined to identify specifically the self-care behaviors of clinical interest. A duration of time relative to other episodes in the chain would be defined for each "Relative Time Slot". For example, two hours may be used as the period of time between the beginning or end of the episode in each slot and the end or start time of the previous or subsequent timeslot (respectively). In the example below, all durations of "Time Slot" was set to two hours, but it is envisioned that the time slot duration setting may be different for some time slots, or even unique for each link in each episode chain. Furthermore, the logic may enforce the absence of one or more episodes in a position of the chain. The presence of an excluded episode would reject the candidate chain from being selected as a match to the self-care behavior.

Further logic is envisioned which would need to resolve "overlapping chains". In these cases, when chains are identified that are coincident in time, there may be logic which either allows them to both remain identified for further analysis (allowing the clinician to review and sort out the overlapping), or there may be a hierarchy of importance or precedence of one chain over another (helping the clinician by removing conflicting self-care behavior activities identified at the same time).

Association of Episode Chains and Self-Care Behavior

One or more episode chains are associated with a clinically-meaningful self-care behavior. These behaviors would be selected because of the risk they pose to the patient and/or the possible interventions (medications, education, etc.) which may be offered to reduce the future occurrence of the episode chain(s).

Display of Search Output

The number of episode chains and self-care behaviors found by the search algorithms could be displayed as a "scorecard", indicating which self-care behaviors were most prevalent. In addition, comparison to historical findings for that patient may be shown. Alternatively, a comparison of self-care behaviors needing improvement for a particular patient could be compared to a population of similar patients. These displays would enable efficient sorting of potentially effective interventions to reduce the number of self-care behaviors problems experienced by the patient. It is envisioned that the display of the results would also provide access to further details and guidance for expert- or evidence-based techniques for addressing these self-care behaviors in a positive way.

In order to provide further insight into the timing and potential patterns of the self-care behaviors experienced by the patient, the episode chain or chains associated with each behavior may be shown in a time-of-day plot, with each episode indicated within the chain. For example, a 24-hour plot may be used, or a 48-hour plot may be used to ensure that episodes that occur after midnight on the day of the kernel episode are shown to be after the kernel, as opposed to "wrapping" to the morning period. The start time of the kernel episode would be indicated to provide reference to the other episodes in the chain. As an alternative display method, the chains could be displayed along a time axis that is referenced to the start time of each kernel episode of each chain type or self-care behavior. This format has the potential to be instructive to the clinician and patient about the recurring cause-and-effect relationships of the episodes of interest.

TABLE 1

Episode and Logic Nomenclature Definitions

Episode Type Definitions:

| | |
|---|---|
| Meal | A patient-recorded meal event |
| Exer | A patient-recorded exercise event |
| L | Low glucose episode |
| H | High glucose episode |
| m-R | meal-related glucose Rise (starts above 75 mg/dL) |
| lt-R | low glucose treatment Rise (starts below 75 mg/dL) |
| F | glucose Fall to below 100 mg/dl |

Logic Definitions:

| | |
|---|---|
| not | Prefix meaning that episode type is not in the relative-time window |
| bolded | This episode is the "kernel" of the search routine, which starts the search algorithm |
| \| | "or" for more than one episode type in the chain position |
| & | "and" for more than one episode type in the chain position |
| Time Slot | amount of time before/after an episode to look for other episodes of interest in the chain |

TABLE 2

Logic definition for identifying self-care behaviors

| Inappropriate Diabetes Self-care Behavior | Episode Chain Relative Time slot | | | | |
|---|---|---|---|---|---|
| | 1 | 2 | 3 | 4 | 5 |
| Meal-to-Insulin Amount Mismatch, too little insulin | notF | m-R | H | — | — |
| | Meal | m-R ! lt-R | NotF | — | — |
| | Meal | H | — | — | — |
| | H | Meal | H | — | — |
| | H | m-R | NotH | — | — |
| Meal-to-Insulin Timing Mismatch, insulin too late | notF | m-R | NotH | — | — |
| | Meal | m-R !lt-R | F | — | — |
| | H | F | not m-R & not lt-R | — | — |
| High overtreatment, without rebound High | H | L | notH | — | — |
| | H | F | notH | — | — |
| | H | Meal | F | NotH& Not m-R | — |
| | H | lt-R | notH | — | — |
| High overtreatment, with rebound High | H | L | H | — | — |
| | H | lt-R | H | — | — |
| | H | F | m-R!/t-R | — | — |
| | H | Meal | F | H | — |
| | H | Meal | F | m-R | — |
| | H | L | lt-R | — | — |
| HiQh undertreatment | H | not L & not lt-R | H | — | — |
| Exercise-induced glucose drop | Exer | F | — | — | — |
| | Exer | L | — | — | — |
| Isolated High, too little insulin | not L & not Jt-R & not H & not Meal | H | not L & not lt-R & not H & not Meal | — | — |
| Rescue Carb | L | Meal | — | — | — |
| Low overtreatment, without rebound Low | notH | lt-R | notL | — | — |
| | F | m-R | notL | — | — |
| | L | lt-R | notL | — | — |
| | notH | L | H | notL | — |
| Low overtreatment, with rebound Low | notH | lt-R | L | — | — |
| | F | m-R | L | — | — |
| | L | lt-R | L | — | — |
| | L | H | L | — | — |
| Low undertreatment | L | not H & not lt-R | L | — | — |
| Isolated Low, too much insulin | not L & not lt-R ¬H | L | not L & not lt-R & not H & not Meal | — | — |

Detailed example of application of invention:
Subject DNB0509, 8Dec06-14Dec06

TABLE 3

Time Slot: 2 hours (universal applied to all time-slots between episode chain links)

| Kernel Start Time | Description (bolded indicates kernel episode) |
|---|---|
| 9Dec06, 5:49 AM: | m-R, H: Meal-to-Insulin Amount Mismatch, too little insulin |
| 9Dec06, 4:59 PM: | m-R, not H: Meal-to-Insulin Timing Mismatch, insulin too late |
| 9Dec06, 10:20 PM: | H: Isolated High, too little insulin |
| 10Dec06: 1:59 PM: | L, Meal: Rescue Carb |
| 10Dec06, 2:11 PM: | not H, lt-R, not L: Low overtreatment without rebound Low |
| 10Dee06, 10:20 PM: | Meal, H: Meal-to-Insulin Amount Mismatch, too little insulin |
| 12Dec06, 8:23 AM: | H, Meal, F, not H & not m-R: High overtreatment, without rebound High |

TABLE 3-continued

Time Slot: 2 hours (universal applied to all time-slots between episode chain links)

| Kernel Start Time | Description (bolded indicates kernel episode) |
|---|---|
| 13Dec06, 3:55 AM: | not H, lt-R, not L: Low overtreatment without rebound Low |
| 13Dec06, 6:56 AM: | m-R, H: Meal-to-Insulin Amount Mismatch, too little insulin |
| 13Dec06, 9:32 AM: | H, Meal, F, H: High overtreatment, with rebound High |
| 13Dec06, 1:26 PM: | not H, lt-R, not L: Low overtreatment without rebound Low |
| 13Dec06, 2:56 PM: | m-R, H: Meal-to-Insulin Amount Mismatch, too little insulin |
| 13Dec06, 6:36 PM: | F, m-R, not L: Low overtreatment without rebound Low |
| 13Dec06, 8:06 PM: | m-R, not H: Meal-to-Insulin Timing Mismatch, insulin too late |
| 14Dec06, 9:37 AM: | H, Meal, F, m-R: High overtreatment, with rebound High |
| 14Dec06, 2:17 PM: | F, m-R, not L: Low overtreatment without rebound Low |
| 14Dec06, 2:19 PM: | Meal, m-R, F: Meal-to-Insulin Timing Mismatch, insulin too late |

TABLE 4

Summary Table, "Self-Care Behavior scorecard"

| Identified Self-Care Behavior | Count |
|---|---|
| Low overtreatment without rebound Low | 5 |
| Meal-to-Insulin Amount Mismatch, too little insulin | 4 |
| Meal-to-Insulin Timing Mismatch insulin too late | 3 |
| High overtreatment with rebound High | 2 |
| High overtreatment without rebound High | 1 |
| Isolated High, too little insulin | 1 |
| Rescue Carb | 1 |
| Grand Total | 17 |

Figure 11:
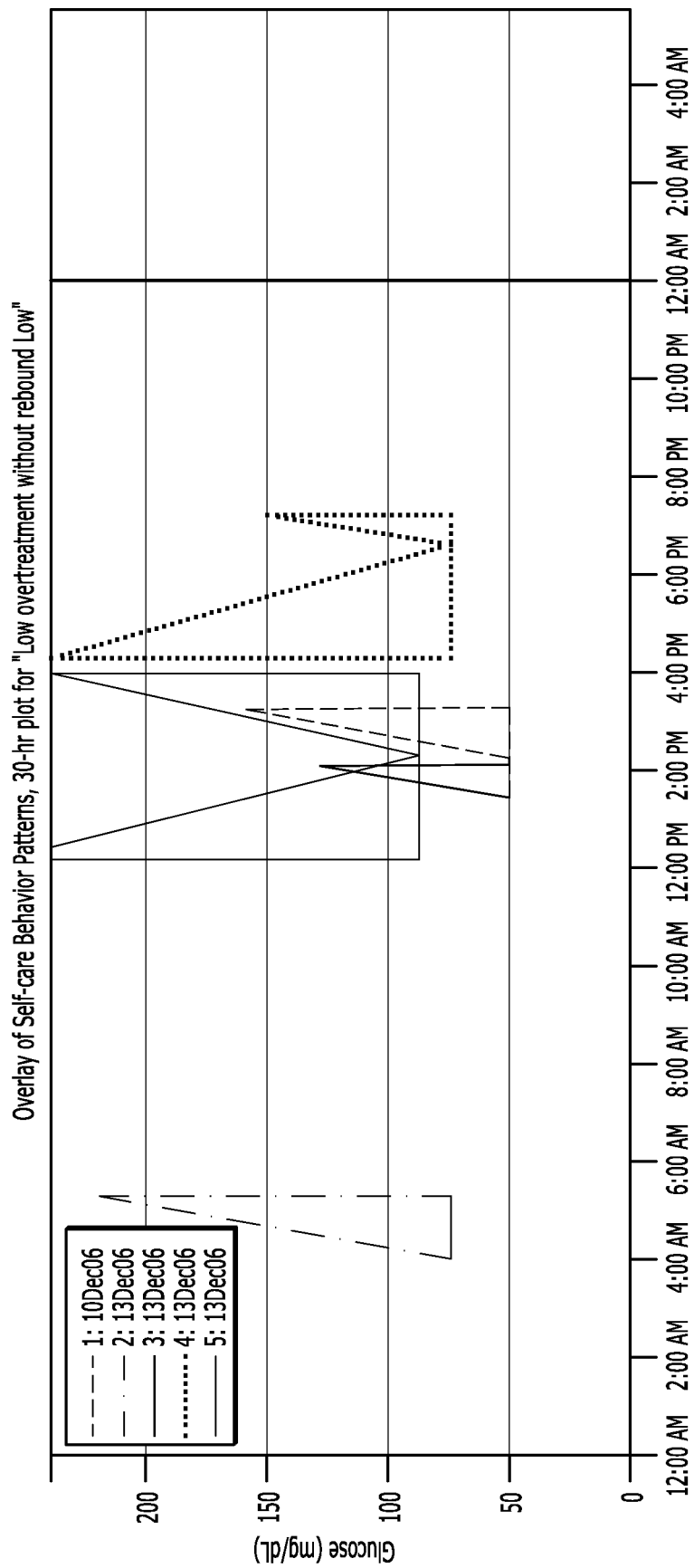
FIG. 11 shows an Overlay of Self-care Behavior Patterns, 30-hour plot for "Low overtreatment without rebound Low;"
Figure 12:
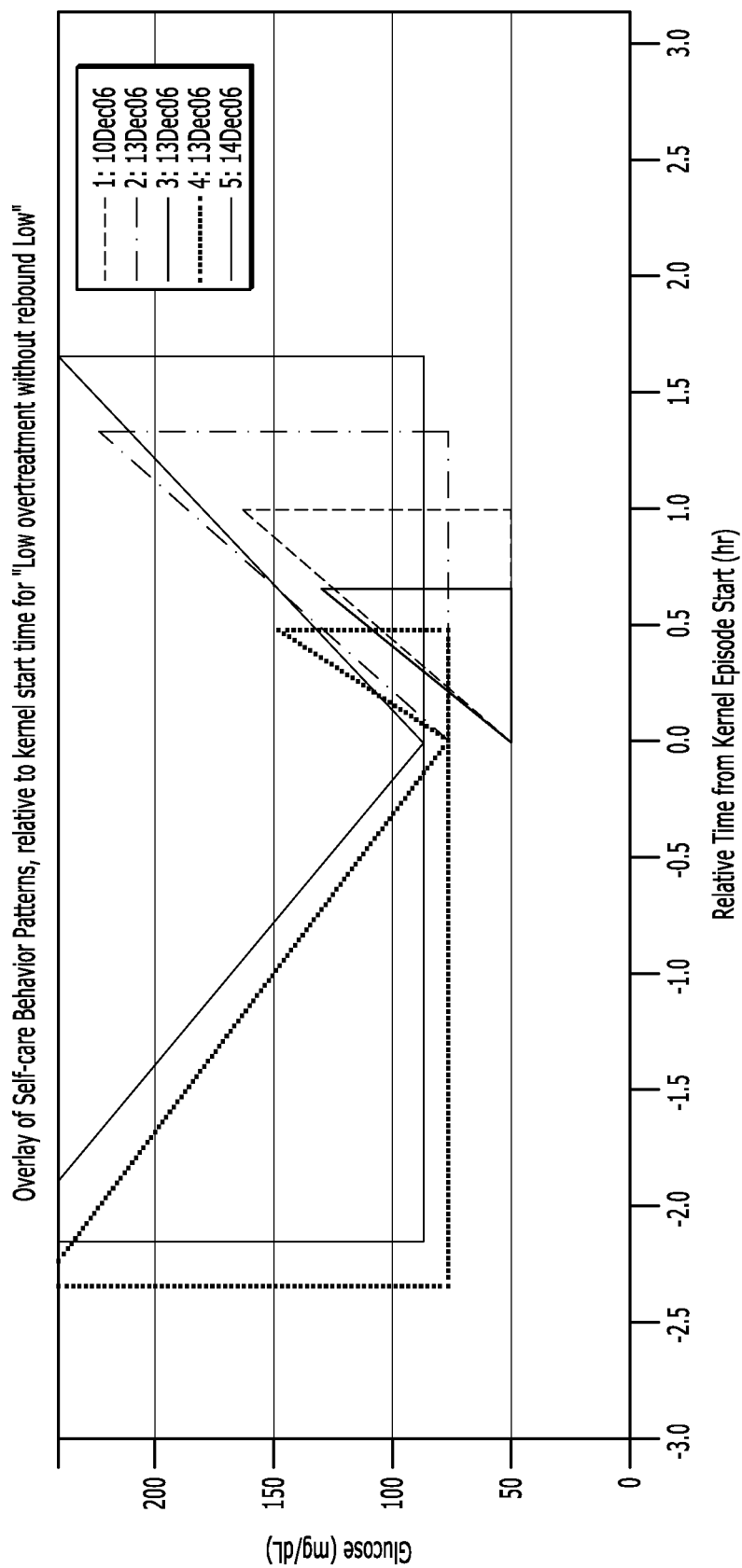
FIG. 12 also shows an Overlay of Self-care Behavior Patterns, relative to kernel start time for "Los overtreatment without rebound Low;"
Figure 13:
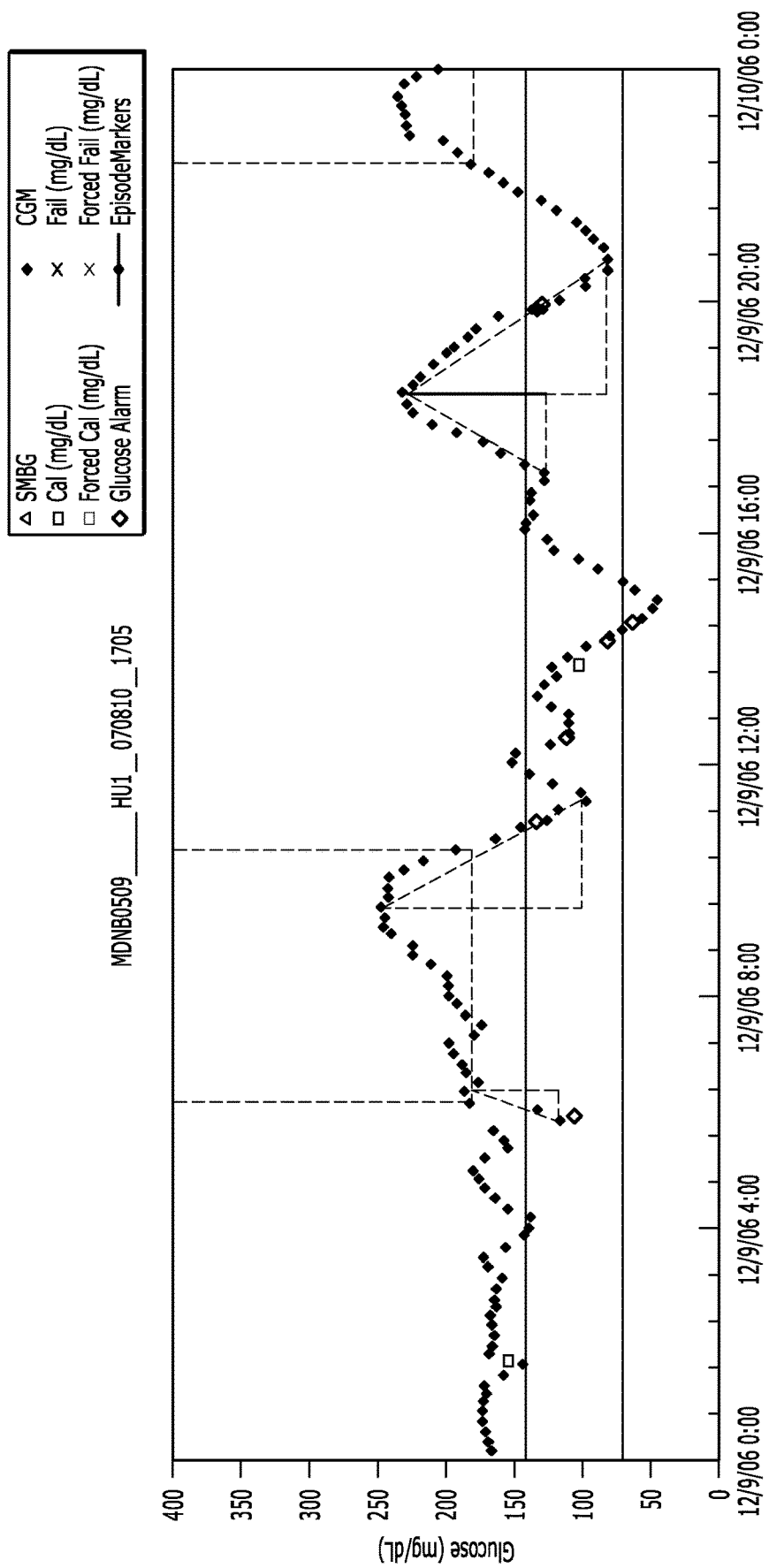
FIG. 13 shows a daily glucose profile example in which CGM data is shown.
Figure 14:
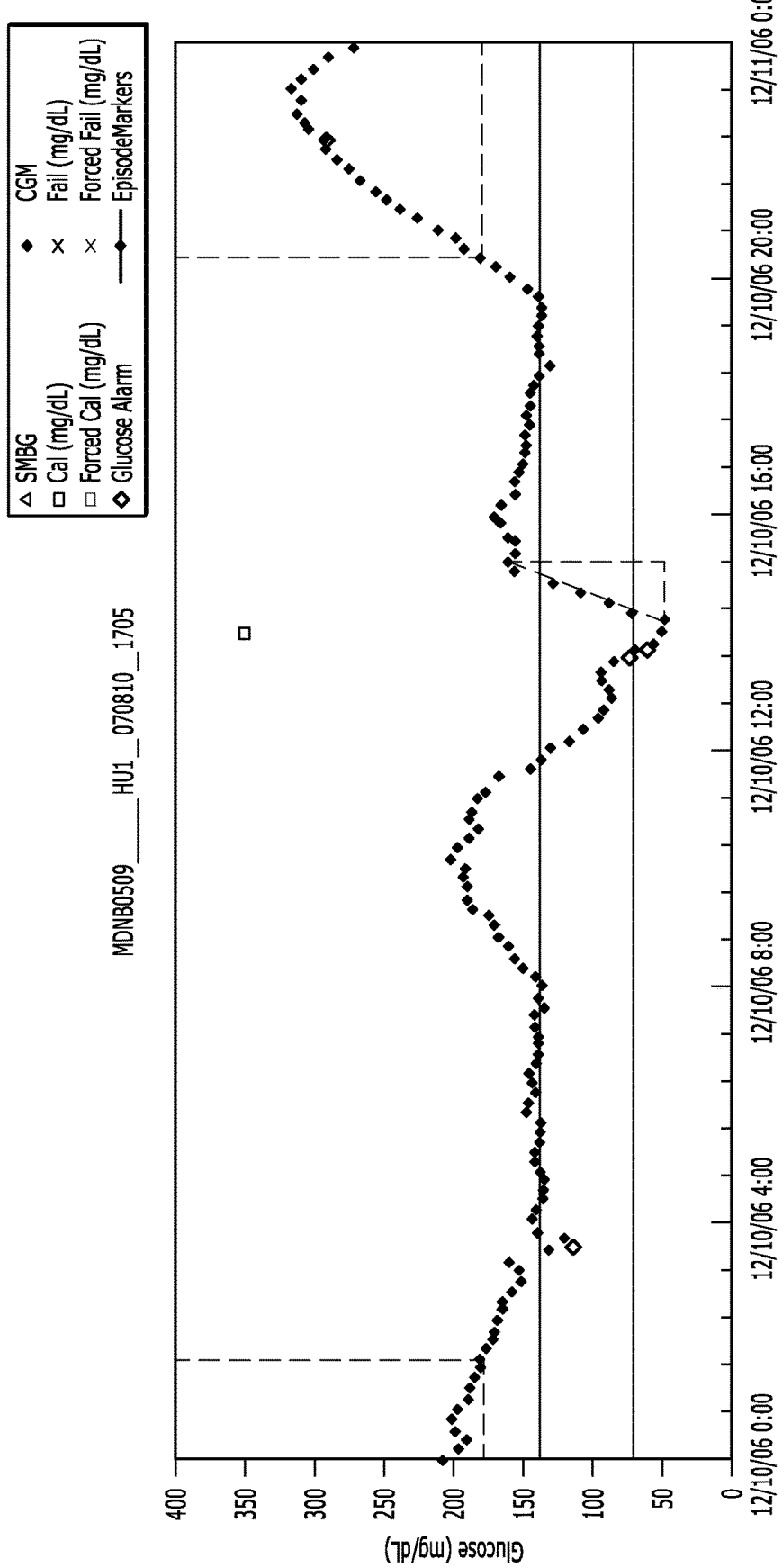
FIG. 14 shows a daily glucose profile example having CGM data with patterns overlayed.
Figure 15:
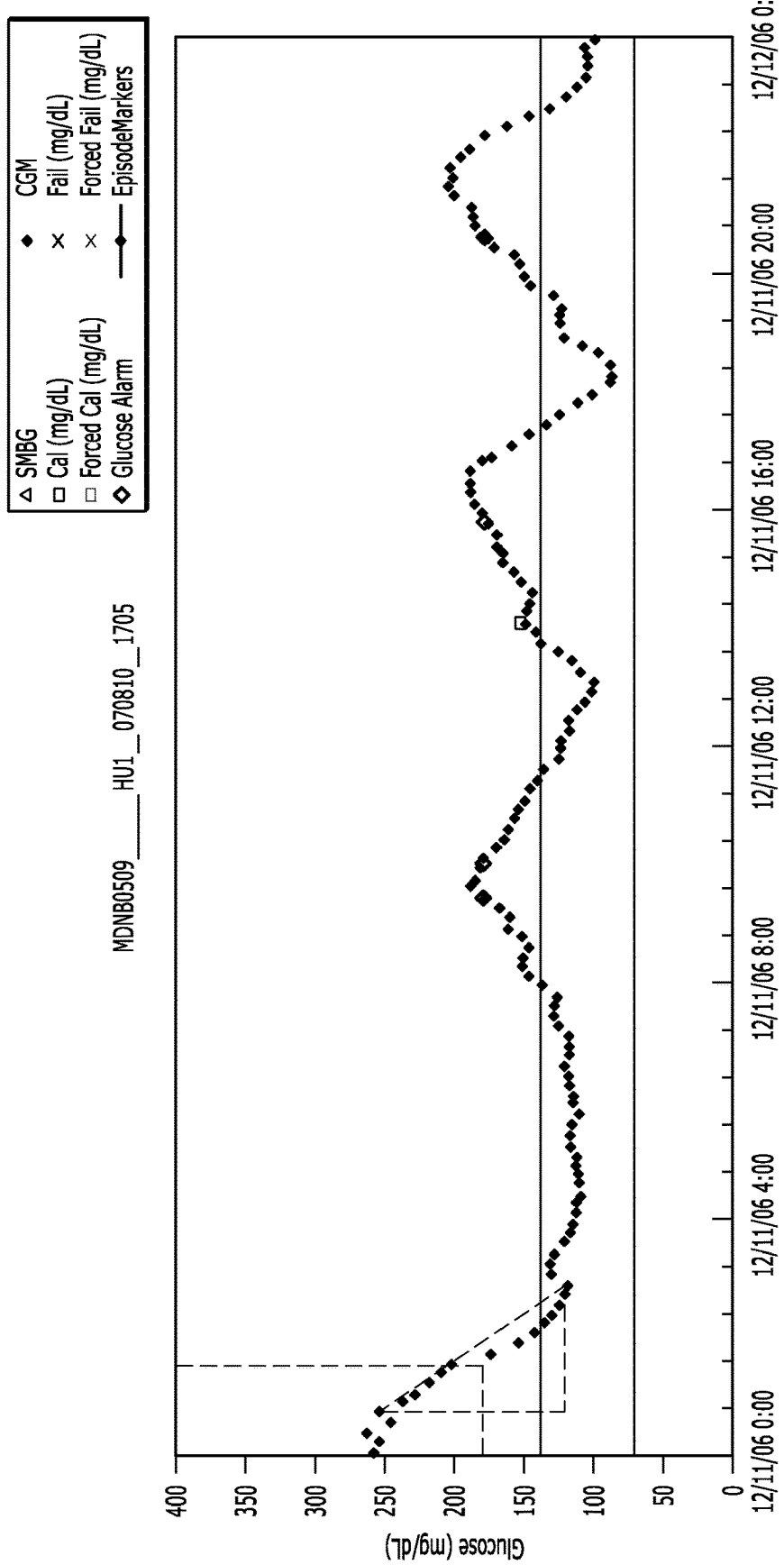
FIG. 15 shows a another daily glucose profile example having CGM data with patterns overlayed.
Figure 16:
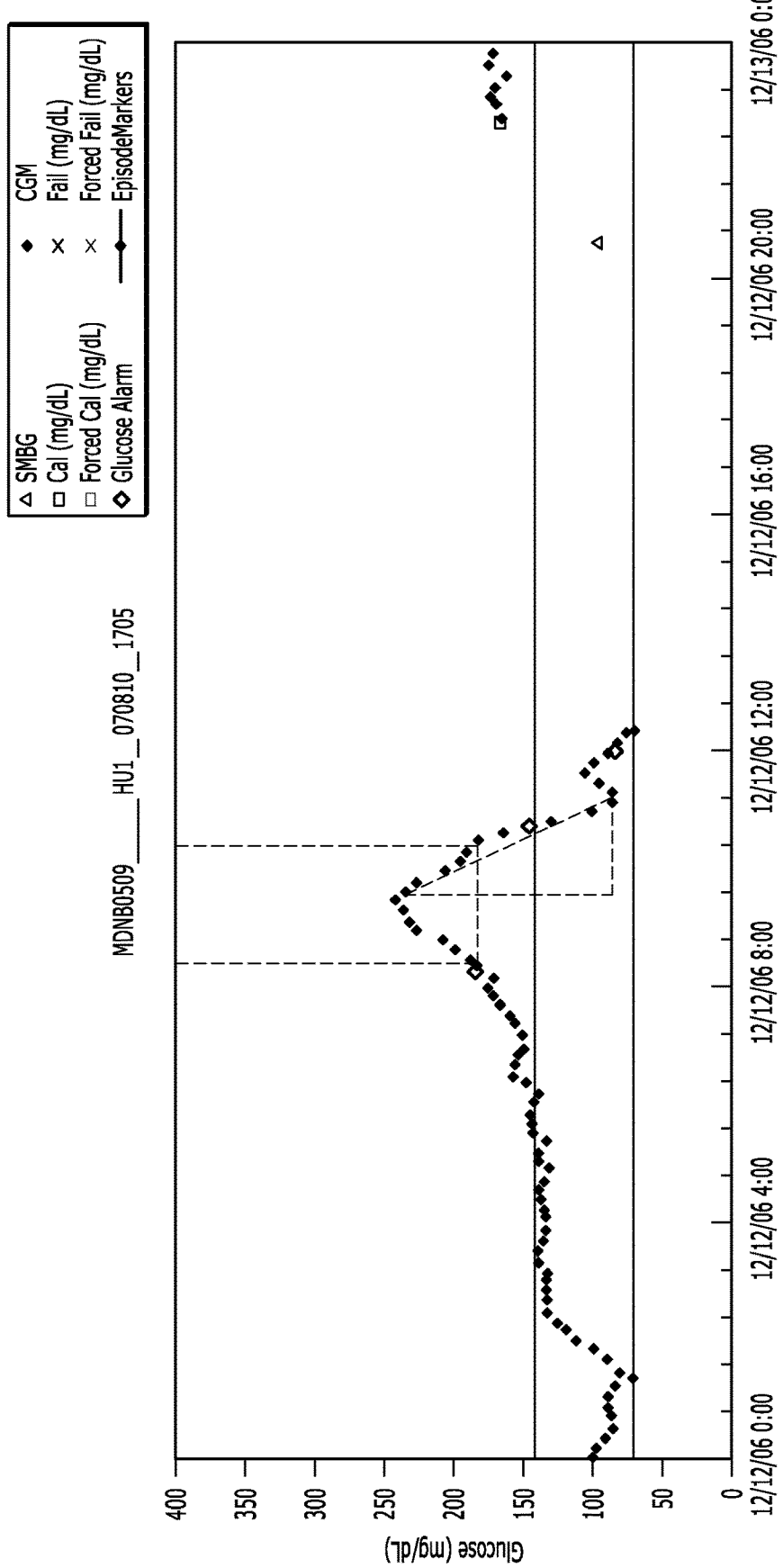
FIG. 16 shows a another daily glucose profile example having CGM data with patterns overlayed.
Figure 17:
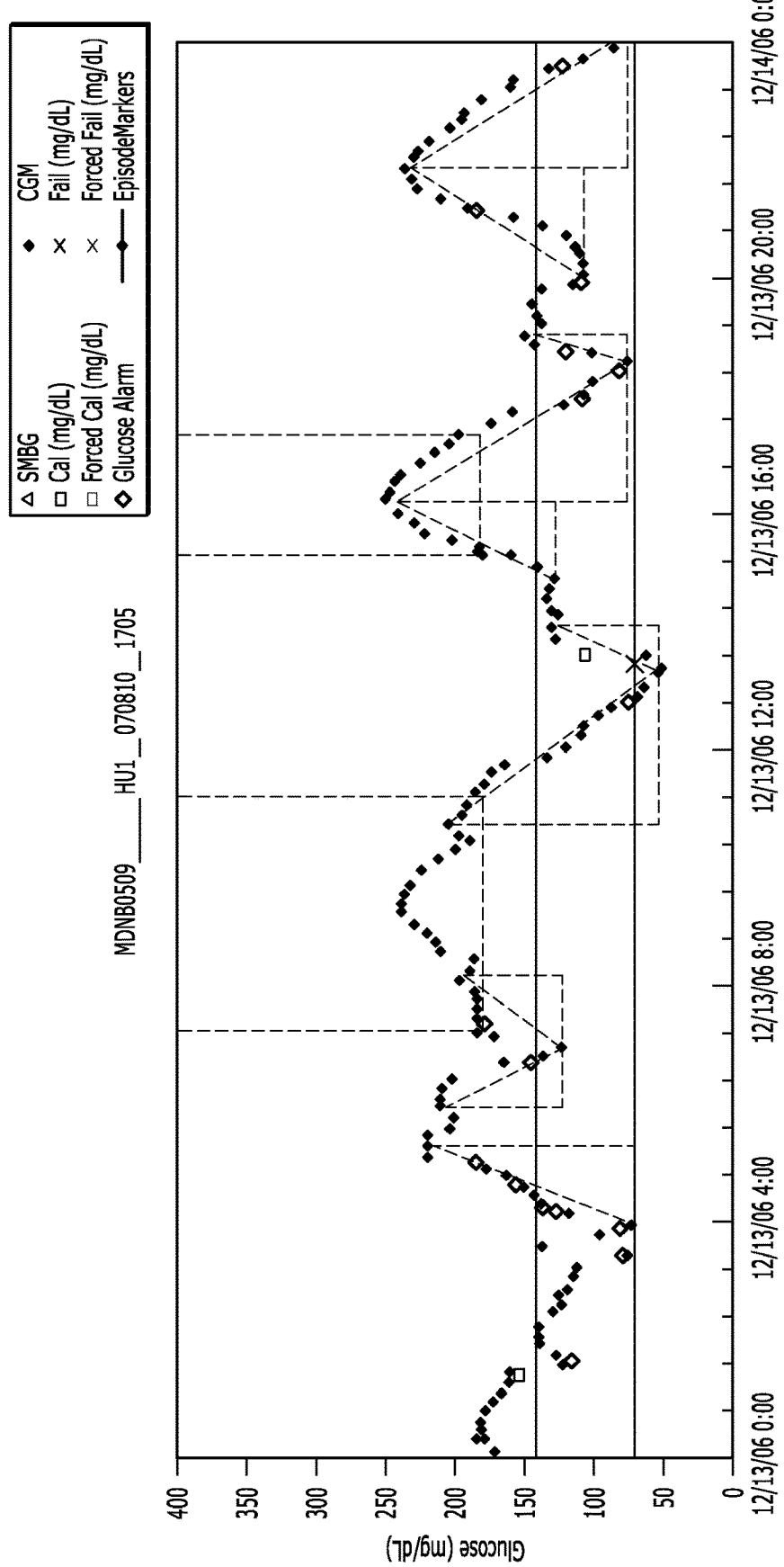
FIG. 17 shows yet another daily glucose profile example having CGM data with patterns overlayed.
Figure 18:
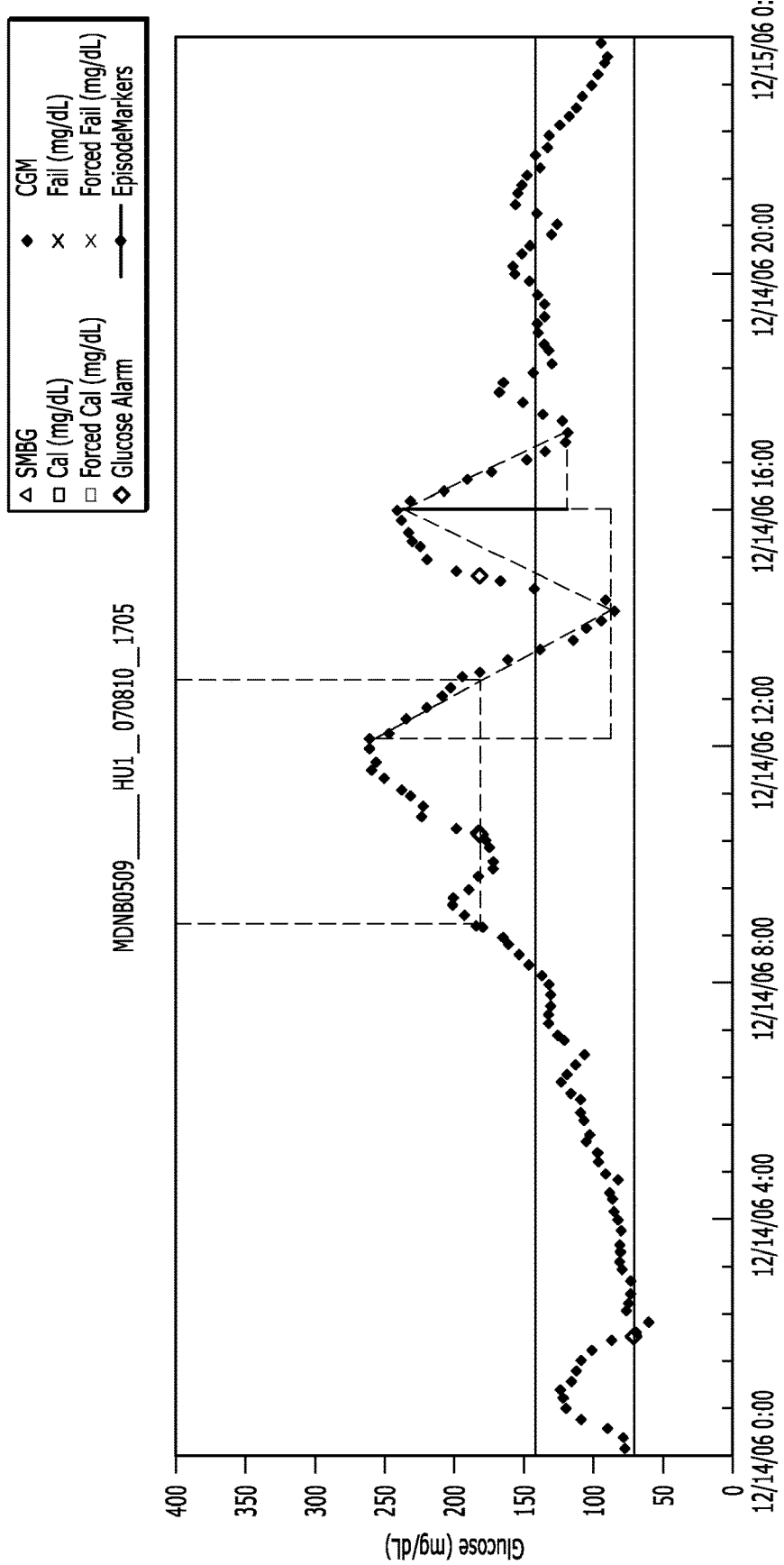
FIG. 18 shows even another daily glucose profile example having CGM data with patterns overlayed.

Illustrative views are presented in FIGS. 11 through 18 in which are shown overlays of behavior patterns on graphs where the vertical shows glucose in mg/dL and the horizontal shows time in a thirty-hour span. Both FIGS. 11 and 12 are related to self-care patterns while FIGS. 13-18 show CGM data overlayed with patterns. For example, in FIG. 13, too little insulin was given at 5:49 am, insulin was given too late at 4:59 pm, and too little insulin was given at 10:20 pm.
Glucose Metric Mappings to Diabetes Treatment Recommendations The invention provides a means to convert glucose data into clinically relevant treatment decisions and the means to map metrics generated from glucose results to treatment recommendations that take into account minimizing the risk of hypoglycemia is described.

The goal is to determine the appropriate therapy modification for a patient based on the measured glucose data. The metrics used are glucose median and glucose variability, calculated for a specified period of time. Variability (or volatility) may be estimated using many different possible metrics—for this description, the lower 40% percentile is used to represent variability. Median is chosen as it is less sensitive to outliers than the mean. However, any metric that would represent central tendency of data may be readily used here.

The Glucose Control Grid

The glucose median and variability may be illustrated graphically where, for instance, the median is represented along the y-axis and the variability is represented along the x-axis. As will be described, this graph will be divided up into zones that represent possible treatment recommendations. This graph is called the Control Grid. These zones can be represented mathematically and implemented in software to provide automated therapy recommendations based on glucose data, as will be described. In addition, the Control Grid itself may be displayed to the "HCP" (healthcare provider) and/or patient by the software.

Figure 19:
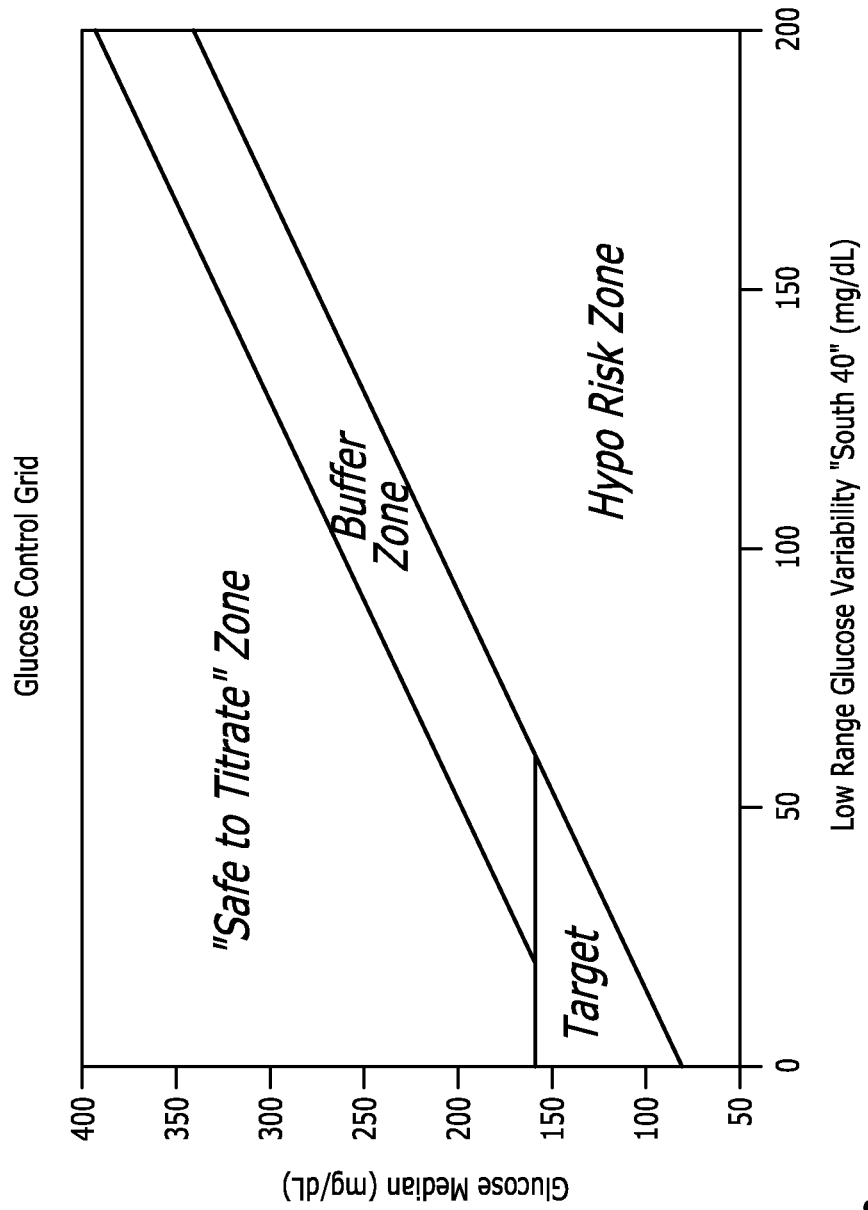
FIG. 19 shows a glucose control grid in which a patient's glucose median and variability are plotted.
Figure 20:
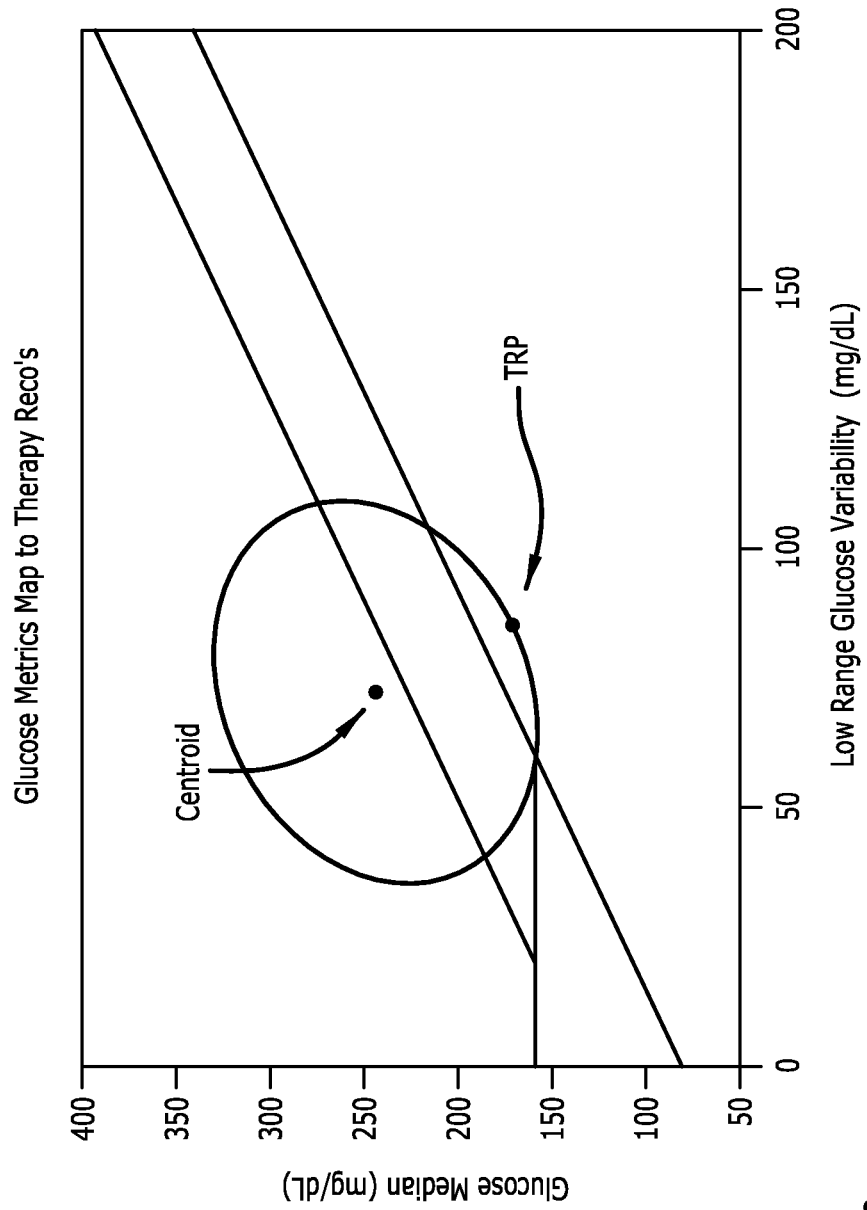
FIG. 20 shows a glucose metrics map to therapy recommendations.

One version of the control grid is illustrated in FIG. 19. A patient's glucose median and variability can be plotted on this grid. Also, the uncertainty in the estimate of the median and variability can be plotted here, for instance, as represented by a cloud of points, or a "bubble", or some other representation, as described previously. These metrics are compared to the lines defining the zones, as will be described below. Note that there are many possible metrics that can be used for comparison, such as the centroid or "best estimated" of the metric, or the 95% confidence point of the metric (referred to as the Treatment Recommendation Point—"TRP"), as illustrated in FIG. 20. Other possible metrics can be readily contemplated.

On this particular control grid shown in FIG. 19 there are four zones defined. The Hypo Risk zone is defined as the region below the hypo risk line where it is determined that, if the TRP falls below, the patient is at an unacceptable risk of hypoglycemia. In this case, the displayed treatment recommendations would be related to reducing the patient's glucose variability and/or increasing the patient's glucose median. For instance, one specific recommendation related to reducing glucose variability would be for the patient to eat more regularly. A specific recommendation related to increasing glucose median would be to reduce the dose or dose rate of glucose-lowering medication.

The Target zone is the ultimate goal for the patient and HCP. The Target zone is defined as being above the Hypo Risk line and below a Target line—the Target line can be adjusted by the HCP to provide an achievable treatment goal appropriate for a particular patient. The preferred embodiment of the logic is that the patient is in the Target zone if a) the TRP is not below the Hypo Risk line and b) the metric centroid falls within the Target zone.

The Buffer zone is defined as the region above the Target zone and the Hypo Risk zone, but below a line defined as an offset above the Hypo Risk zone. This offset is representative of the possible or expected drop in median due to an increase in glucose-lowering mediation. This zone represents the region where, if the TRP was contained within it, it would be unsafe to recommend an increase in medication, since it may drive the patient into the Hypo Risk zone, assuming that glucose variability did not change. In this case, the displayed recommendation would be related to reducing the patient's glucose variability.

Figure 21:
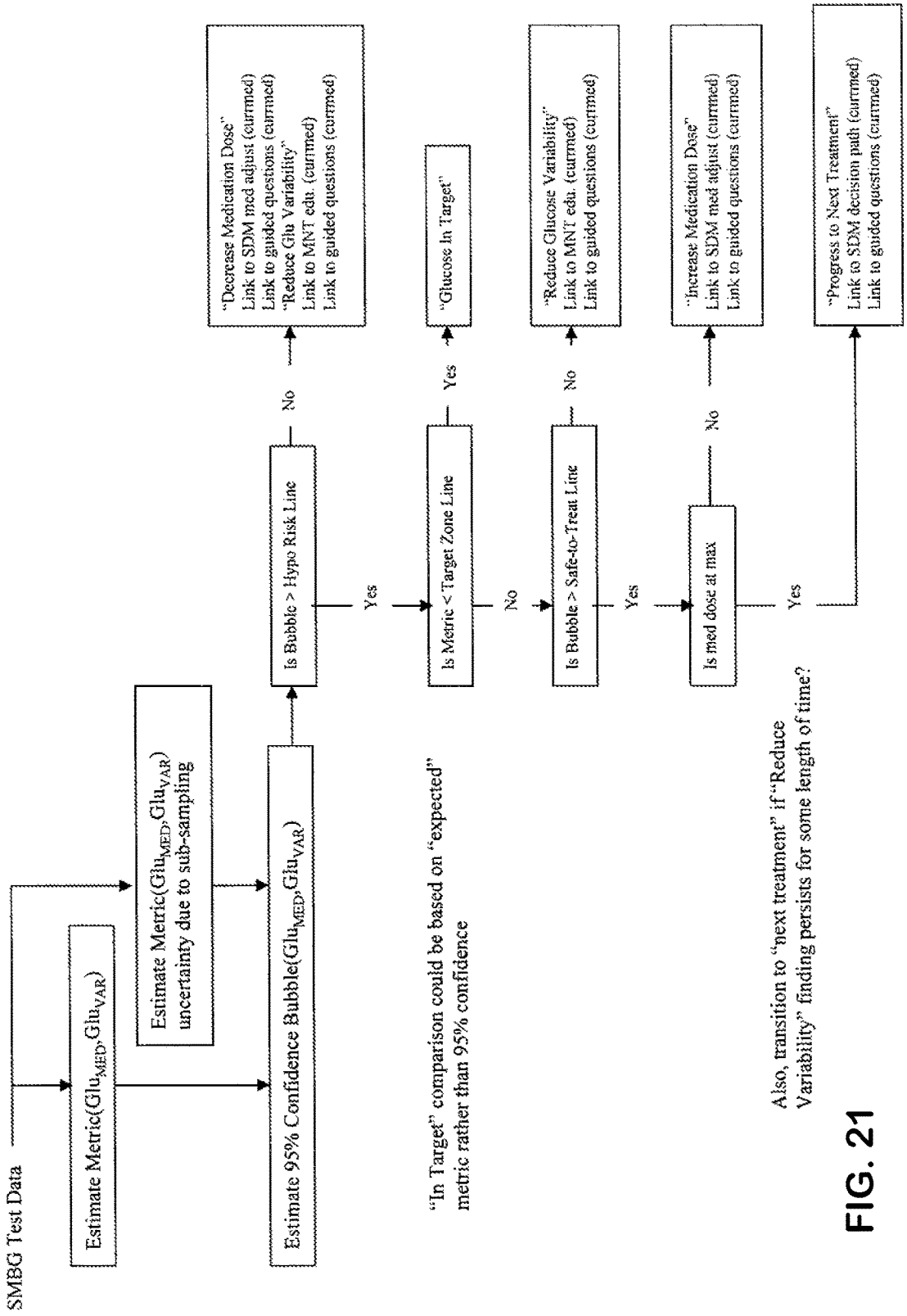
FIG. 21 shows a treatment recommendation algorithm functional flow.

The "Safe to Titrate" zone is defined as the region where the TRP is above the Buffer zone and above the Target zone. Here the recommendation would be related to increasing the patient's glucose-lowering medication dose in order to reduce their median glucose. The logic diagram in FIG. 21 illustrates the mapping described above.

Figure 22:
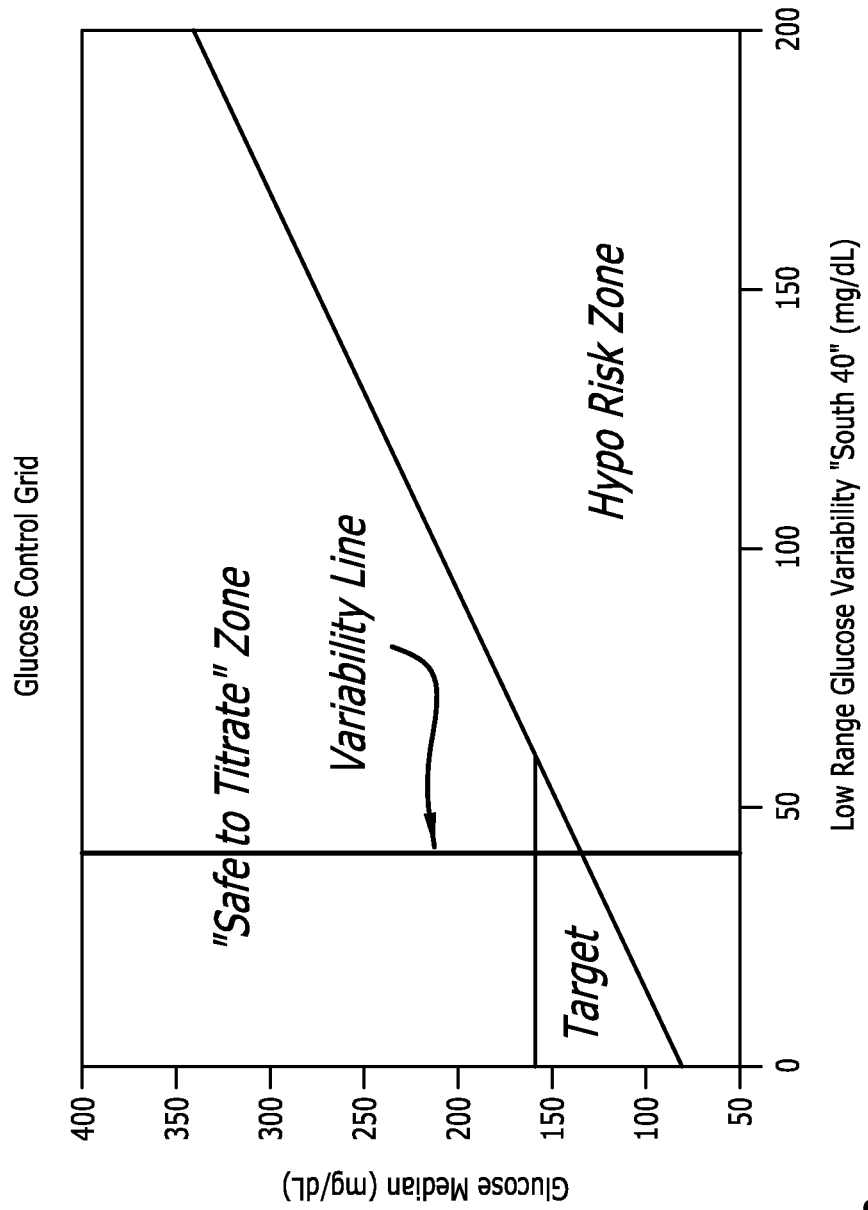
FIG. 22 shows a Glucose Control Grid modified from FIG. 19 with a variability line includes.

The Control Grid can be fashioned a number of different ways. For instance, what has been described as straight lines may be more appropriate to describe as curves, for instance, for the Hypo Risk line. As another example, a Control Grid design is shown in FIG. 22 which illustrates two modifications to the previous Control Grid example. The first modification is to remove the Buffer zone and replace it with recommendations displayed that specifically indicate the distance from the Hypo Risk line. For instance, for a TRP that is located 30 mg/dL above the Hypo Risk line in the "Safe-to-Titrate" zone, the recommendation may read "Increase dose of glucose-lowering medication, margin to safely reduce median glucose is 30 mg/dL". The modified recommendations can indicate both the margin above and below the Hypo Risk line. For instance, for a TRP that is located 10 mg/dL below the Hypo Risk line, the recommendation may read "Decrease dose of glucose-lowering medication, a 10 mg/dL increase in median glucose is needed to reduce hypoglycemia risk to a safe level". Alternatively, the recommendation may indicate the positive or negative horizontal distance from the Hypo Risk line, in terms of variability reduction. Combination of these can also be contemplated. The main reason to eliminate the fixed buffer zone is that dose increments may achieve different glucose median reductions, depending on the medication used or the patient's physiology. Another embodiment is to provide a mechanism where the HCP can modify the Buffer zone depending on these factors that could impact glucose median reductions.

The second modification to the Control Grid shown in FIG. 22 is the addition of a vertical Variability line used to drive variability related recommendations. Here, some or all of the zones are further divided into sub-zones. In the sub-zones where the centroid metric is to the right of the Variability line, variability related recommendations are provided. Where the centroid metric is to the left of the Variability line, variability related recommendations are not provided. The Variability line may be defined as fixed at a specific location on the x-axis; that is, at a specific variability value. The preferred embodiment is to for the x-axis location of the Variability line to depend on the Target line and/or the Hypo Risk line. For instance, the location may be determined by the intersection of the Target line and the line defined as 50 mg/dL above the Hypo Risk line. This provides for variability recommendations appropriate for the target set for a specific patient.

Another example of a control grid includes inclusion of a buffer zone at an offset above and/or below the Hypo Risk line. For instance, if the TRP is within this zone, then the recommendations would not include a recommendation for medication adjustment. Outside this zone, the recommendation would include a medication adjustment recommendation. Another example is a zone defined by the Hypo Risk zone divided by the Target line. For a centroid metric above this line, the recommendation would not include decreasing medication, but below the line, the recommendation would include decreasing medication. With these examples, it is clear how alternative zones can be designed and utilized.

Zones may also indicate multiple recommendations at varying degrees of importance. The degree of importance may be indicated by the order in which they are listed, or by color coding the recommendations, or by any other appropriate means.

Recommendations may also include other factors not directly related to treatment. For example, the recommendations may pertain to the need to increase SMBG (self-monitored blood glucose) sampling frequency. Additional sub-zones can be included in the control grid, for instance, such that when the TRP is below the Hypo Risk line, but the centroid metric is above the Hypo Risk line, the recommendation includes reduction in variability and the need to increase sampling frequency in order to reduce uncertainty in the metric. The sampling frequency increase recommendation can also be generated by comparing the size of the "uncertainty bubble" to a predetermined size and if the bubble crosses one or more of the lines on the grid, then an increase in sampling frequency is recommended. Various measures of "uncertainty bubble" size can be contemplated, including a figure of merit of the distance between the centroid and the TRP.

Configuration of Control Grid Logic

In a further aspect, it is contemplated that the parameters of the Control Grid may be modified by the HCP. The software that implements the automated therapy recommendation logic would provide a means, such as a popup screen, for the HCP to alter the lines on the Control Grid, or select certain features of the Control Grid. A preferred embodiment is to allow the HCP to select from a pick list of possible Target levels and Hypo Risk levels. The Target levels on the list may be associated with various diabetes complication statistics such as corresponding A1c. For instance, it may be more acceptable for a patient with A1c of 10% to have a near-term target of 9% rather than 7% so as not to be discourages. The Hypo Risk levels may be adjusted as necessary to tailor to a patient's tolerance of hypoglycemia. The Hypo Risk pick list labeling may be associated with expected frequency of hypoglycemia, a relative measure of hypoglycemia risk such as High, Medium, Low, or any other appropriate labeling. In the software, the Recommendation algorithm may be initially run with default parameters (either predefined in the code or set to the last algorithm run for that patient from a previous doctor's visit). A popup window would be provided to allow the HCP to alter one or more of these algorithm input parameters as needed, and the algorithm is rerun, generating new recommendations.

Control Grid by Time of Day

Another aspect of this invention is to use the Control Grid based algorithm to process data for specific time periods of the day or relative time periods related to key events. For example, four key time periods can be defined as overnight/fasting (12 am-8 am), post breakfast (8 am-12 pm), post lunch (12 pm-6 pm), and post dinner (6 pm-12 am). Glucose data collected for multiple days can be grouped into these time periods and the Control Grid algorithm run for each group. This is useful for generating recommendations that are specific to time periods. For instance, variability recommendations may be generated specific to meals or overnight. For patient's whose treatment is multiple daily injections (MDI) of insulin, the time-period targeted recommendations may be specific to insulin needs during these times of day. For instance, the Control Grid for the over-night/fasting period may indicate that medication dosage should be increase; the recommendation may indicate that the patient's long-acting insulin dose should be increased.

Figure 23:
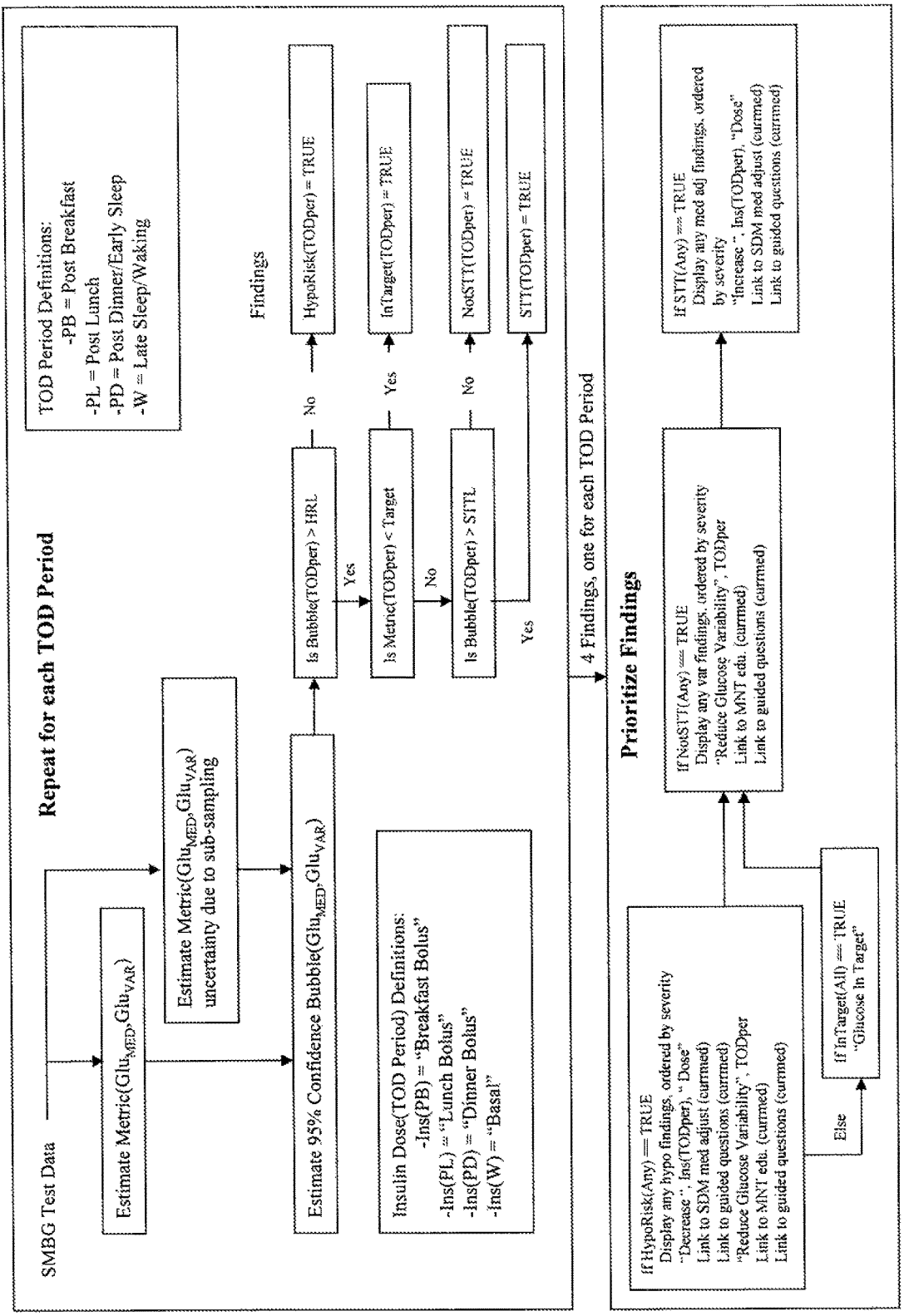
FIG. 23 shows an option treatment recommendation algorithm functional flow.

The treatment recommendation logic may be more complicated when multiple Control Grids are used. An example of this logic is shown in the FIG. 23.

Alternatively to fixed time periods, the Control Grid algorithm can be applied to time periods defined relatively to events. Specifically, data grouping can be determined, for example, a) 4 hours past breakfast, b) 4 hours past lunch, c) 4 hours past dinner, and d) 4-10 hours past dinner. Various permutations of this example can be imagined. The data groups will then be processed by the multiple Control Grid algorithm as described above.

Second-Stage Logic to Drive Recommendations

An augmentation of the treatment recommendation described above using the Control Grid algorithm is to provide second-stage logic to further narrow the possible recommendations that can be made. For instance, there are many different recommendations for reducing glucose variability, such as "stop snacking", "don't forget to take your medication", "don't miss meals", "adjust correction dose of insulin". A glucose control zone may be associated with a number of these recommendations. A second stage of logic may be used to narrow down the list of recommendations. Detection of episodic patterns, as described elsewhere, can be used in this second stage to narrow the list of recommendations. For instance, if an instance of low fasting glucose is detected preceded by a post-dinner high glucose, this may be an indication of occasional correction dosing to mitigate a high glucose value, and the logic could direct the recommendation to only include "adjust correction dose of insulin". The logic may require a certain frequency of occurrence of an episodic pattern.

Recommendation Structure and Logic Integrated with Treatment Stage

The mapping of glucose data to treatment recommendations may be implemented with the use of a lookup table. The inputs to this table are the output of the Control Grid analysis and the current treatment and treatment stage. The outputs are recommendations of different types that are displayed. FIG. 24 shows a simple example of a treatment recommendation lookup table. Notice that multiple recommendations can be associated with a single input combination. The concept of a lookup table can be easily extended to more complex glucose metric to recommendation mappings.

Recommendations can take the form of text that is directly displayed, as indicated in the column labeled "Recommended Text" in FIG. 24. They can also take the form of links to source documents and specific pages of the source documents. The content of these source documents may provide more detailed instructions regarding treatment changes. For instance, for a recommendation to change dosage of a medication or a change in treatment, the source document may be published instructions for medication start and adjustment, and the link could be specified to present the appropriate page of these instructions. Another form of recommendations could be questions displayed to guide the HCP in interviewing their patient to uncover underlying issues in self-care management. These questions could be in the form of text to be directly displayed, or reference material. Recommendations may also take the form of guidance about testing frequency or how to alter algorithm input parameters. The key benefit here to the user is that this information is targeted based on analysis of the patient's glucose tests.

Note that, as illustrated in FIG. 24, recommendations can be tailored to current treatment.

Additional types of recommendations or outputs associated with the inputs to this table can be implemented, including for instance, links to sources of definitions, links to appropriate pages of a user guide, or links to graphical displays of the data appropriate to illustrate the glucose analysis finding and recommendation. The links could be instantiated by the user via buttons (the software would need to place a button associated with the recommendation when needed), or they could be instantiated similarly with a hotspot, or could automatically present the linked information in a popup window or a window dedicated for this information.

The structure for the lookup table may be altered when recommendations are to be provided based on multiple time-of-day periods. This could be done using multiple tables or incorporating multiple algorithm result inputs and multiple associated groups of recommendations into a single table.

As noted previously, if a second stage of logic is employed, the lookup table needs to be adjusted to accommodate this. For example, if hypoglycemic risk is detected in 3 of the 4 time-of-day periods, rather than display a separate recommendation related to reducing hypoglycemic risk for each time period, the second stage logic would map these into a general recommendation and indicate that it applies to the three time periods.

Glucose Episode Detection System and Method

A robust search system and method are described for identifying clinically relevant glucose episodes from strip- and sensor-derived glucose measurements. This is an improvement of existing data analysis and report generation systems and methods present in informatics systems. This invention proposes methods to search glucose data for episodes of interest. Existing informatics software typically focus on overall summary statistics, such as median and percent of readings in target. Collecting clinically-meaningful glucose episodes and doing analysis on those provides a higher-level view of the data and may provide more actionable information.

Figure 25:
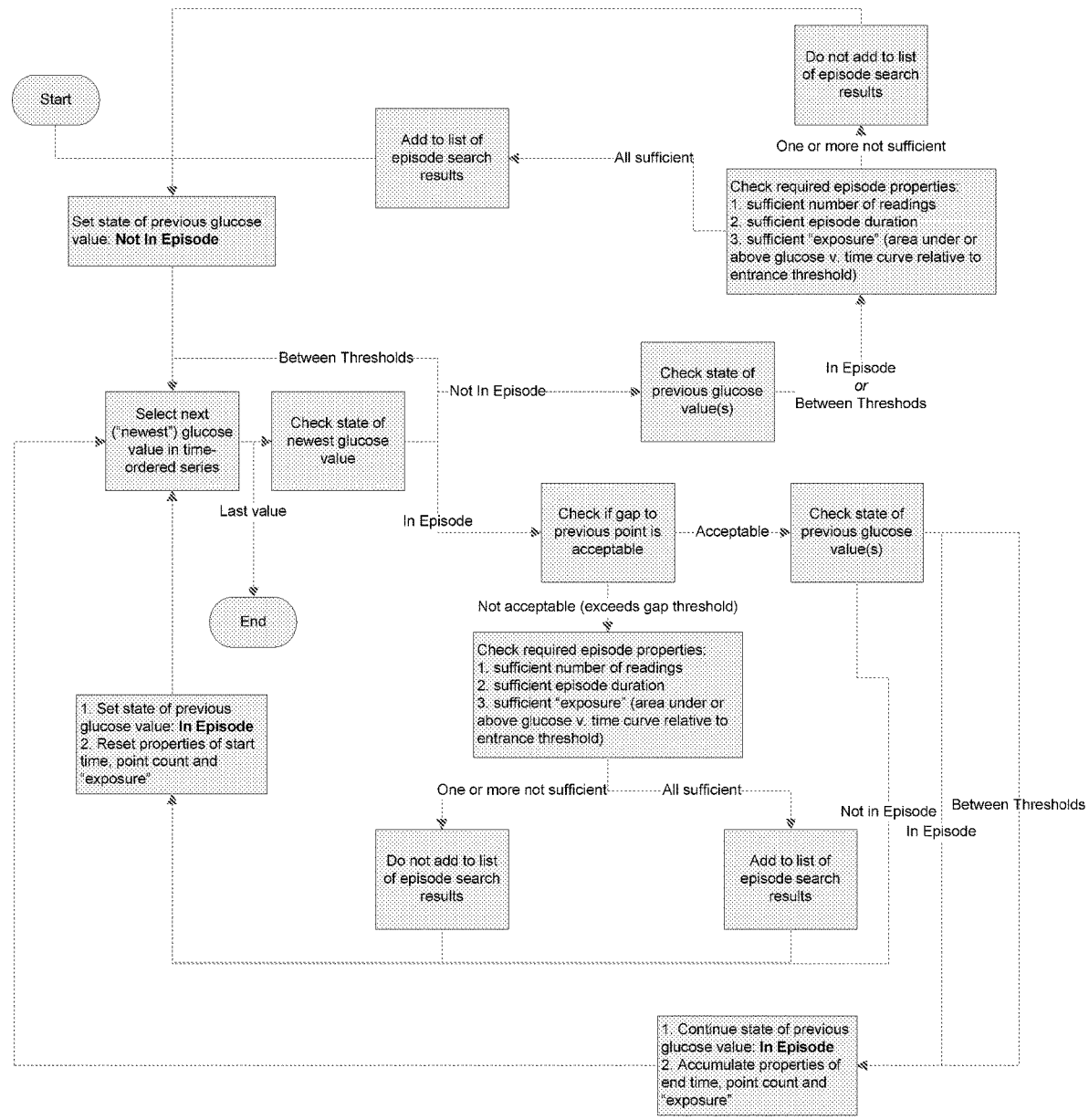
FIG. 25 shows a block diagram of threshold-based episode detection algorithm.

The present invention addresses the difficulties encountered (e.g. briefness/outliers, gaps, noise) in searching frequent (say every 1 to 30 minutes) glucose values to detect extreme episodes of clinical interest. Therefore, the episode search algorithm results can be more clinically meaningful. In addition, this invention specifies the properties of episodes that can be clinically meaningful. These properties can also be used to construct sequences, or "chains", of episodes that have specific clinical meaning related to self-care behaviors. See FIG. 25 for a block diagram of an embodiment of a threshold-based episode detection algorithm in accordance with aspects of the invention.

Figure 26:
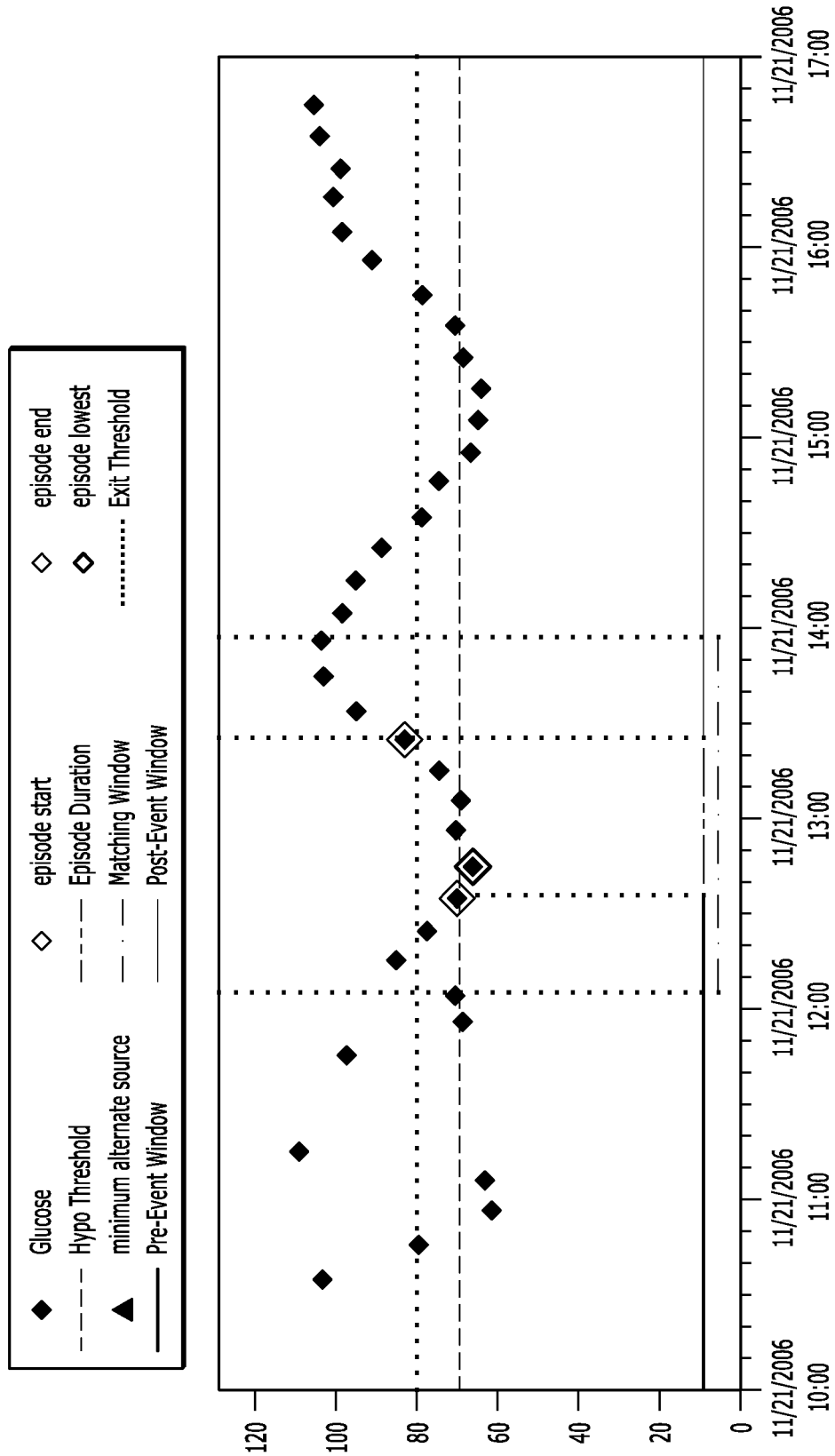
FIG. 26 shows a hypoglycemic episode example.
Figure 27:
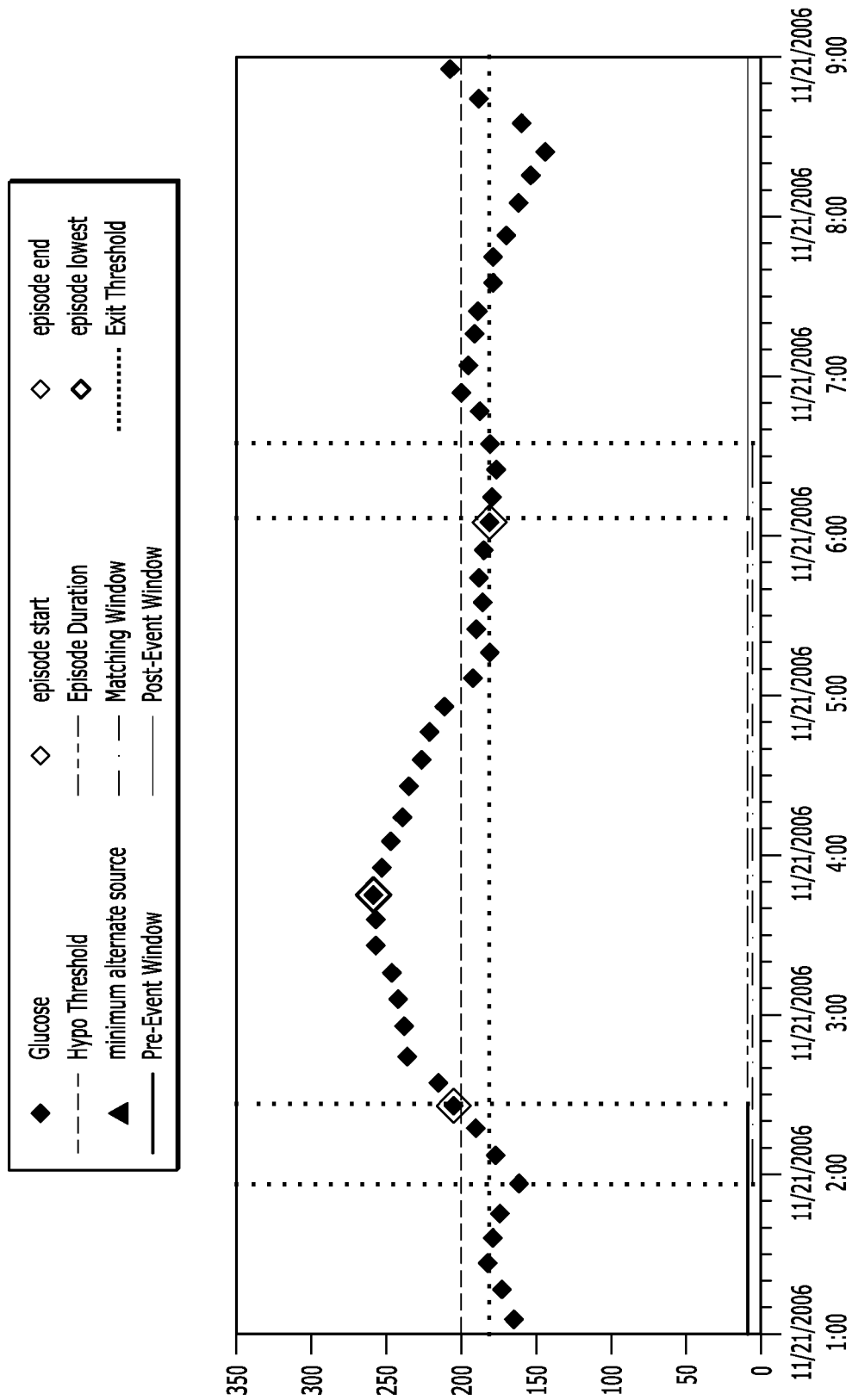
FIG. 27 shows a hyperglycemic episode example.
Figure 29:
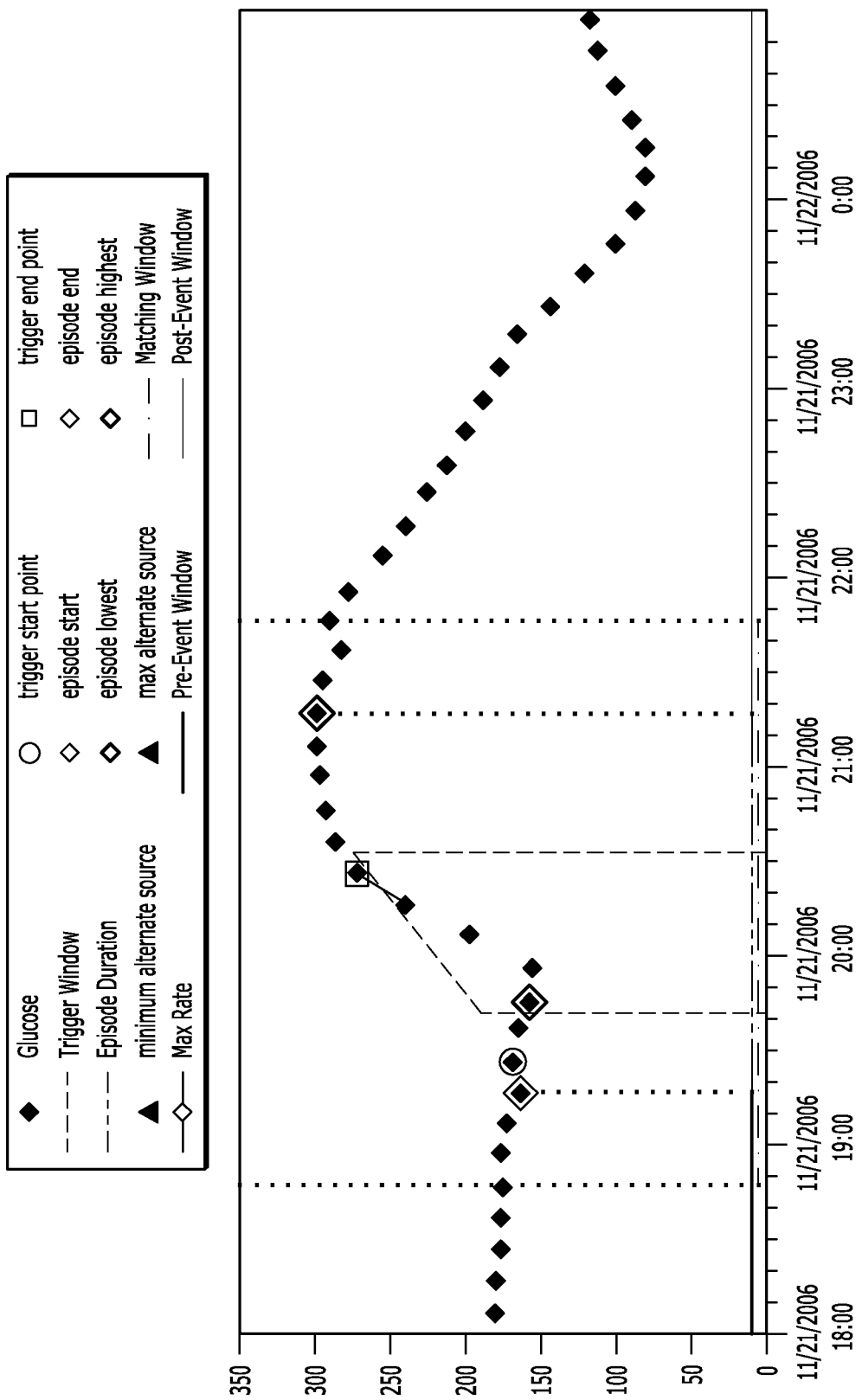
FIG. 29 shows a glucose rise episode detection example.
Figure 30:
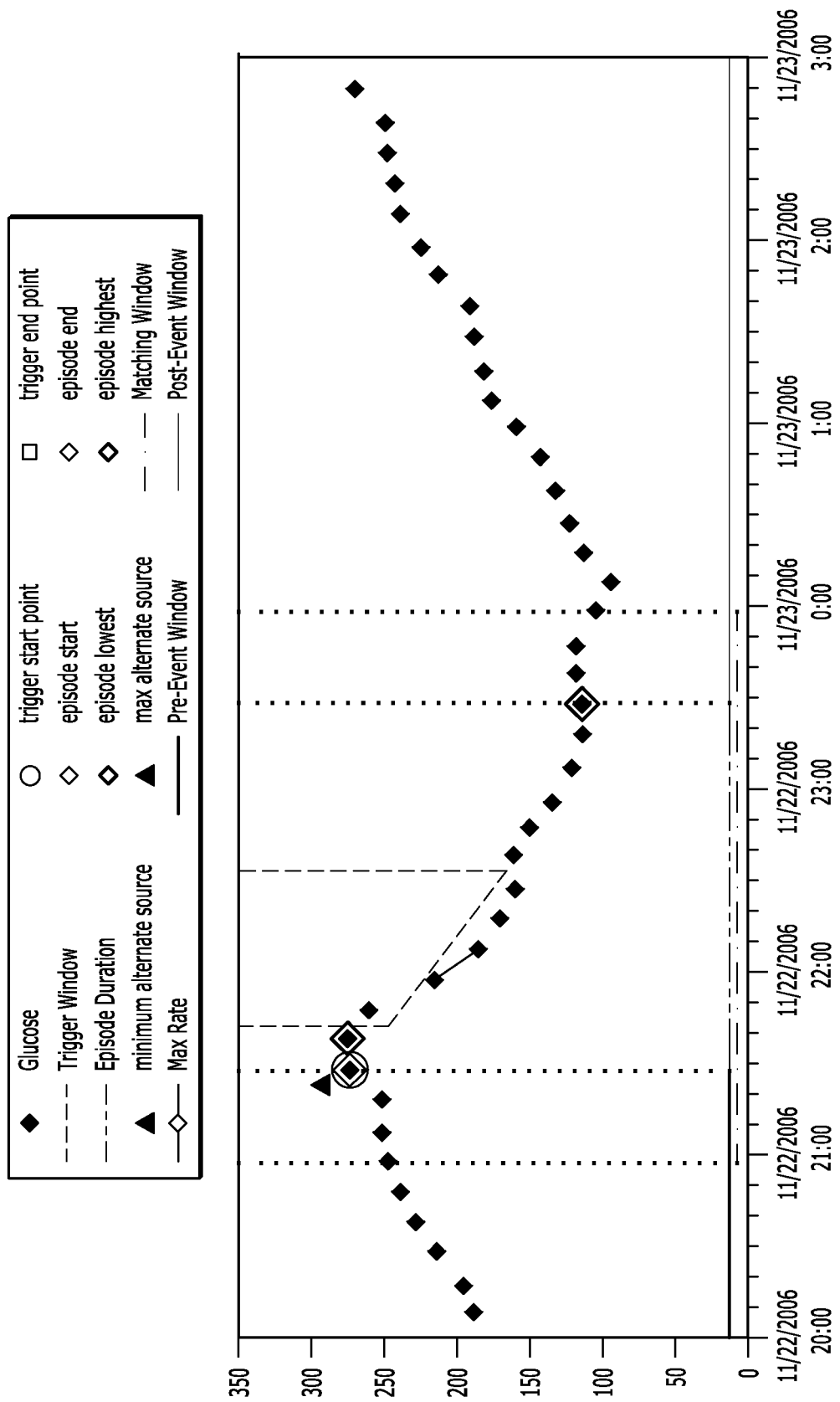
FIG. 30 shows a glucose fall episode detection example.

The core logic of episode analysis falls into two families: threshold-based, and change-based. Looking for episodes in both directions suggest four basic episode types:

1. Low Glucose/Hypoglycemia (readings below a threshold) (see FIG. 26)
2. High Glucose/Hyperglycemia (readings above a threshold) (see FIG. 27)
3. Glucose Fall (rate of change more negative than a (negative) threshold) (see FIG. 29)
4. Glucose Rise (rate of change more positive than a (positive) threshold) (see FIG. 30)

Figure 28:
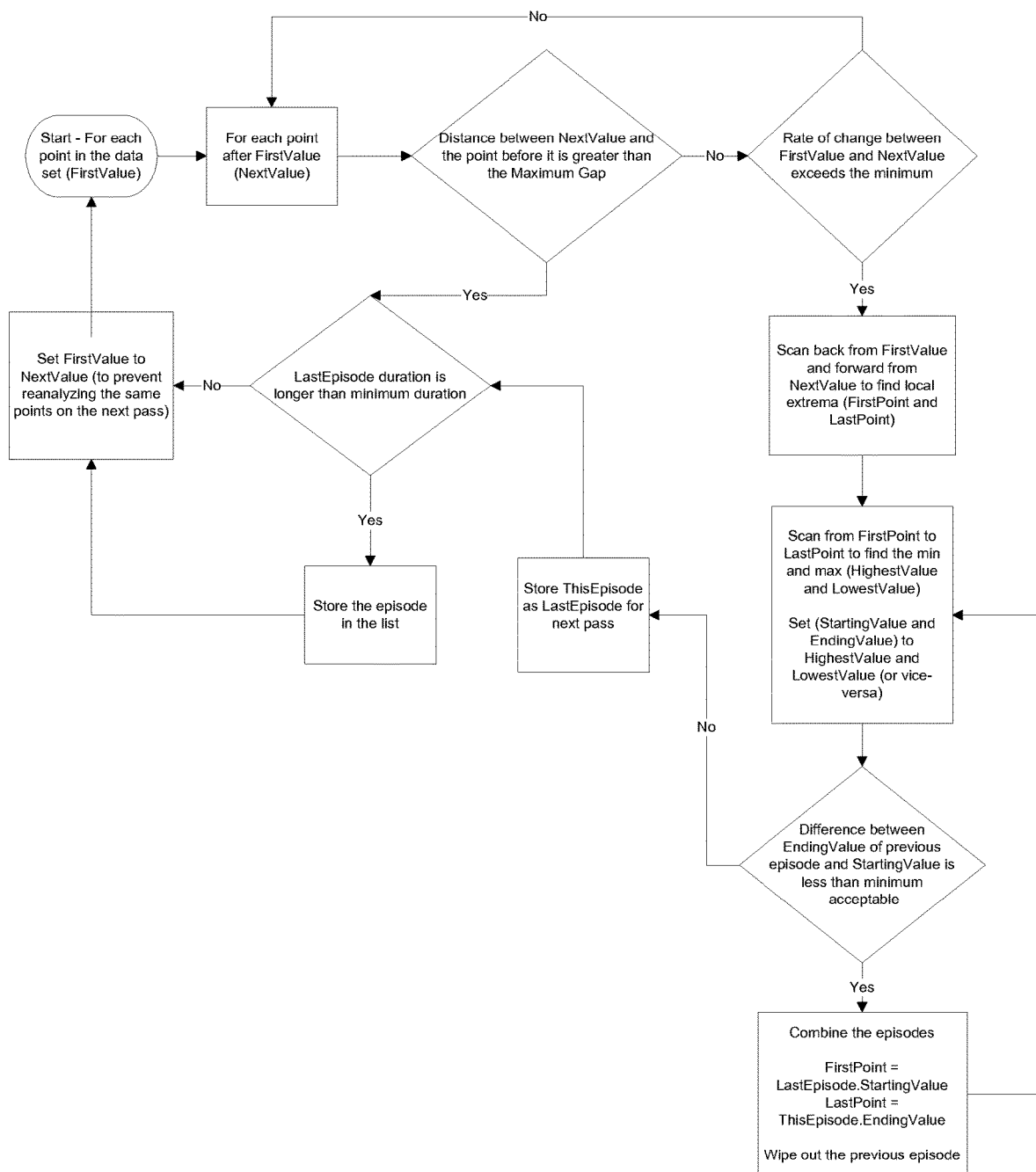
FIG. 28 shows a block diagram of change-based episode detection algorithm.

In addition, when looking for sequences, or "chains", of episodes, it is foreseen to be useful to also define a "within target" episode, where glucose values are maintained between an upper and lower bound for a period of time. Detection of these episodes can be done by extension of the threshold-based episode detection algorithms. See FIG. 28 for a block diagram of a change-based episode detection algorithm in accordance with aspects of the invention.

Threshold-Based Episodes

The simplest form of threshold-based logic would be to just group all consecutive points (above/below) a threshold into an episode. This invention improves on this approach to address the following challenges:

Very brief episodes/outlier values are not clinically relevant—The present invention manages this challenge by requiring a minimum number of readings and/or a minimum duration and/or a minimum area outside the threshold to consider the episode for analysis; an episode failing any of the requirements is ignored.

Gaps (periods of time lacking readings) in the data can significantly alter episode durations—The present invention manages this by setting a maximum gap duration. Any gaps longer than the maximum result in the episode spanning the gap are split into two separate episodes that are each analyzed, assuming that they individually meet all analysis criteria.

Noise in the signal will cause many episodes to be recorded when the true value is close to the threshold—The present invention manages this by defining an exit threshold inside (less extreme than) the episode threshold. This serves to debounce the signal, because the episode is only terminated following a threshold crossing if the signal also crosses the exit threshold.

Properties of threshold episodes, as so defined, can be defined for clinical utility, including but not limited to: threshold value, most extreme value (magnitude of excursion past threshold), episode duration, or episode area. This provides a virtually limitless catalog of episode types, each of which, if independently clinically relevant, could form the basis for reports and analysis.

Visual Representation of Relative Positions of Thresholds:
In Episode (Hyperglycemia)
    Hyperglycemic Episode Threshold
Between Thresholds (Hyperglycemia)
    Hyperglycemic Exit Threshold
Not In Episode
    Hypoglycemic Exit Threshold
Between Thresholds (Hypoglycemia)
    Hypoglycemic Episode Threshold
In Episode (Hypoglycemia)
Example Pseudocode Implementation of Threshold-Based Episode Detection Algorithm:

```
//"State" is the previous condition, "PointState" is the condition for the new point
void BuildList( )
{
    EpisodeState State = NotInEpisode;
    For Each CGMValue In Database
        EpisodeState PointState = GetEpisodeState(CGMValue)
        if (PointState == InEpisode)
        {
            if (Gap from previous point >= maximum gap)
            {
                //end of possible episode
                //if it passes all checks...
                        if (ReadingsInEpisode >= MinimumReadings
                            && EpisodeDuration >= MinimumDuration
                            && EpisodeArea >= MinimumArea)
                        {
                            //add it to the list of episodes
                        }
                //Start of posssible episode
                //record start time, reset point count and cumulative area
            }
            if (State == NotInEpisode)
                //Start of possible episode
                //record start time, reset point count and cumulative area
            }
            else if (State == InEpisode)
            {
                //continuation of possible episode
                //push back end time, increment point count, add to cumulative area
            }
            else // if (State == BetweenThresholds)
            {
                //debounce region
            }
            State = InEpisode;
        }
        else if (PointState == NotInEpisode)
        {
            if (State == BetweenThresholds || State == InEpisode)
            {
                //end of possible episode
                //if it passes all checks...
                        if (ReadingsInEpisode >= MinimumReadings
                            && EpisodeDuration >= MinimumDuration
                            && EpisodeArea >= MinimumArea)
                        {
                            //add it to the list of episodes
                        }
            }
            State == NotInEpisode;
        }
    Next CGMValue
}
```

Change-Based Episodes

The simplest form of change based logic would be to group all consecutive monotonically increasing/decreasing points into an episode. This invention improves on this approach to address the following challenges:

Changes small in magnitude are not meaningful—the present invention manages this by requiring the core of the episode to have a rate of change that exceeds a threshold. The core of the episode is the set of points that initially trigger the analysis, when two points are found that have a high enough rate of change for a long enough time between them, they form the core of an episode which is expanded by scanning outwards for local extrema.

Signal variation exaggerates the rate of change of very brief episodes—the present invention manages this by enforcing a minimum duration over which the rate of change must exceed the threshold.

Gaps (periods of time lacking readings) in the data can significantly alter episode durations—the present invention manages this by setting a maximum gap duration. Any gaps longer than the maximum result in the episode spanning the gap are split into two separate episodes that are each analyzed, assuming that they individually meet all analysis criteria. All of the points before the gap are considered a complete (potential) episode with the last point being the point preceding the gap. All the points after the gap form the start of a (potential) new episode.

Noise in the signal breaks the monotonicity of the change during periods of relatively slow change—the present invention manages this by merging episodes that are close together into a single episode. The result of the merge is a newly defined episode containing all of the points between the first point of the first episode and the last point of the second episode, inclusive.

Episodes merged in this way could have intermediate extreme points outside of the end values—the present invention manages this is by redefining the start and end of the episode to be the most extreme points anywhere in the newly merged episode.

Episodes redefined in this way could include spikes caused by two closely spaced points where one of which is an outlier—the present invention manages this by enforcing the minimum duration criteria (rejecting those that do not meet the criteria).

Properties of change episodes, as so defined, can be defined, including but not limited to: maximum rate, delta (highest-lowest values), lowest value, and highest value. This provides a virtually limitless catalog of episode types, each of which, if independently clinically relevant, could form the basis for reports and analysis.

Example Pseudocode Implementation of Change-Based Episode Detection Algorithm:

```
void BuildList( )
{
    For Each FirstValue In Database
        For Each NextValue In Database (Starting at FirstValue)
            if (Distance between NextValue and point before it > MaxGap)
            {
                if (Last Episode passes checks)
                {
                    //log last episode
                }
                        FirstValue = NextValue
                        Next FirstValue
            }
            else if (GetRateOfChange(FirstValue, NextValue) > Threshold)
            {
                StartingValue = ScanBackForLocalExtrema(FirstValue);
                EndingValue = ScanForwardForLocalExtrema(NextValue);
                HighestValue = FindMaxBetween(StartingValue, EndingValue);
                LowestValue = FindMinBetween(StartingValue, EndingValue);
                Starting Value = (HighestValue or LowestValue);
                EndingValue = (LowestValue or HighestValue);
                if (StartingValue is close enough to EndingValue of last episode)
                {
                    //merge with last episode
                }
                else
                {
                    if (Last Episode passes checks)
                    {
                        //log last episode
                    }
                    //store this episode as last episode for next pass
                }
            }
        Next NextValue
    Next FirstValue
}
```

Using Glucose Medial and Variability Metrics to Detect Prolonged Hyperglycemia Risk and Provide Guidance to Modify Treatment The use of the control grid concept (glucose median vs. glucose variability) to associate glucose readings with risk of prolonged hyperglycemia and to direct treatment guidance.

Figure 31:
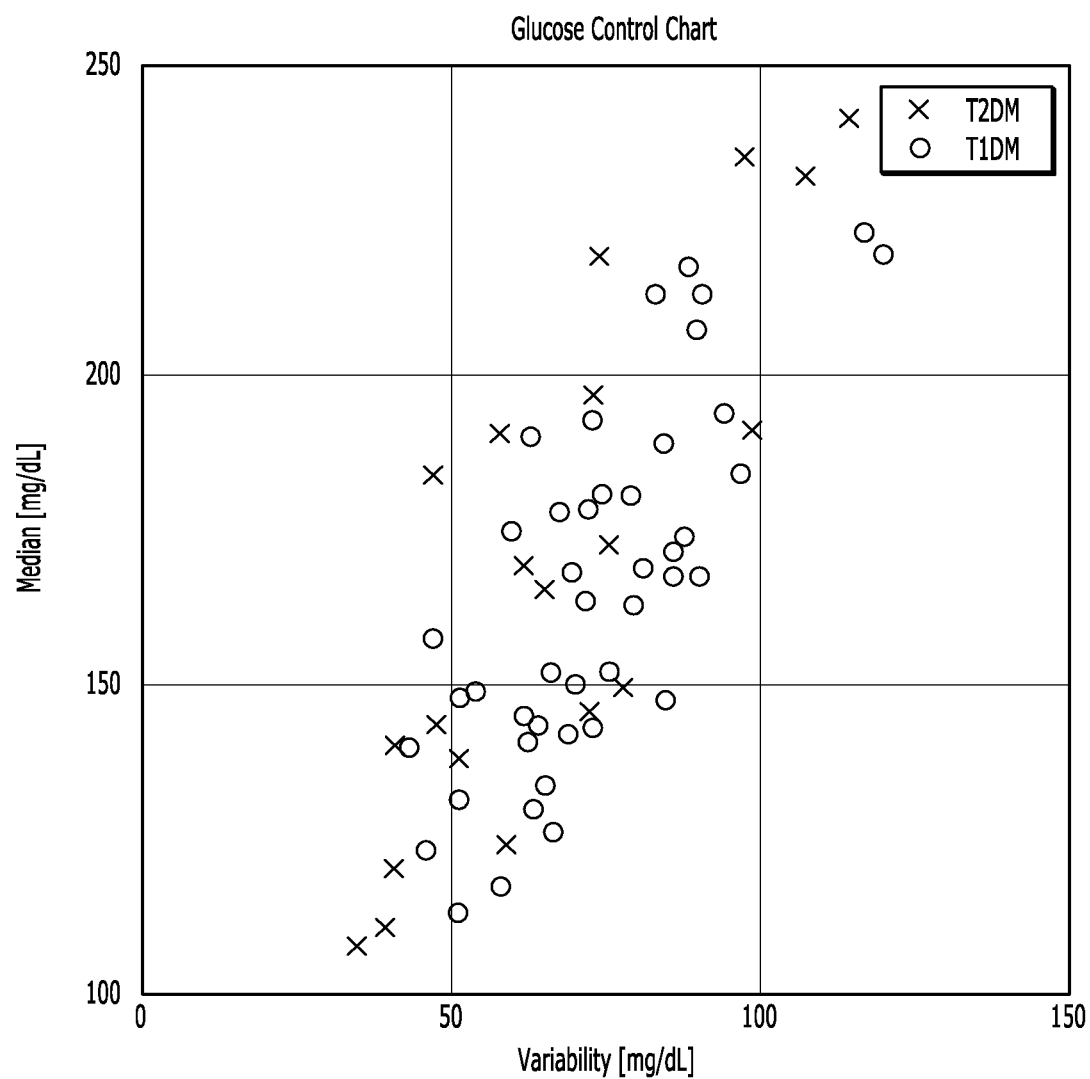
FIG. 31 is an example of a glucose control chart showing the states of sixty-six patients with diabetes mellitus.

A patient's state of glucose control can be assessed in terms of two simple metrics. The first relates to the ability to maintain a desirable glucose level on average. The second relates to the ability to minimize the glucose excursion in the presence of meals and other factors. A method to graphically present these two metrics was previously developed. In one embodiment of this aforementioned graphical representation, median glucose is the first metric, and the difference between the median and the 10th percentile glucose is the second. This graphical representation, called glucose control chart, is shown in FIG. 31. The first metric is shown on the y-axis, and the metric concept is shown on the x-axis.

In addition to the patient's state of glucose control, other clinically relevant information can be provided to enhance one's understanding of the impact of a planned treatment on the patient's various clinical state. Two clinical risks exist, namely risk of retinopathy due to long term high average glucose, and risk of acute hypoglycemia.

This invention provides extensions in which risk of hyperglycemia and accumulated high average glucose, are further elaborated. Risk of hyperglycemia and its link to the glucose control chart is derived in a similar manner as that of the risk of hypoglycemia. Risk of accumulated high average glucose can be separated into long (i.e. in the course of months or more) and medium (i.e. in the course of half a day or more) term exposure to high average glucose.

An example of the risk of long-term accumulated high average glucose, the risk of retinopathy. Other long-term risks such as the risk of nepropathy, neuropathy, macrovascular disease, and microalbuminuria, are tied to the patient's HbA1c, and thus can be linked to the glucose control chart in the same manner for the risk of retinopathy. An example of the risk of medium-term accumulated high average glucose, such as DKA (diabetic ketoacidosis), and the linking of such risk to the glucose control chart, is described in this disclosure.

Figure 32B:
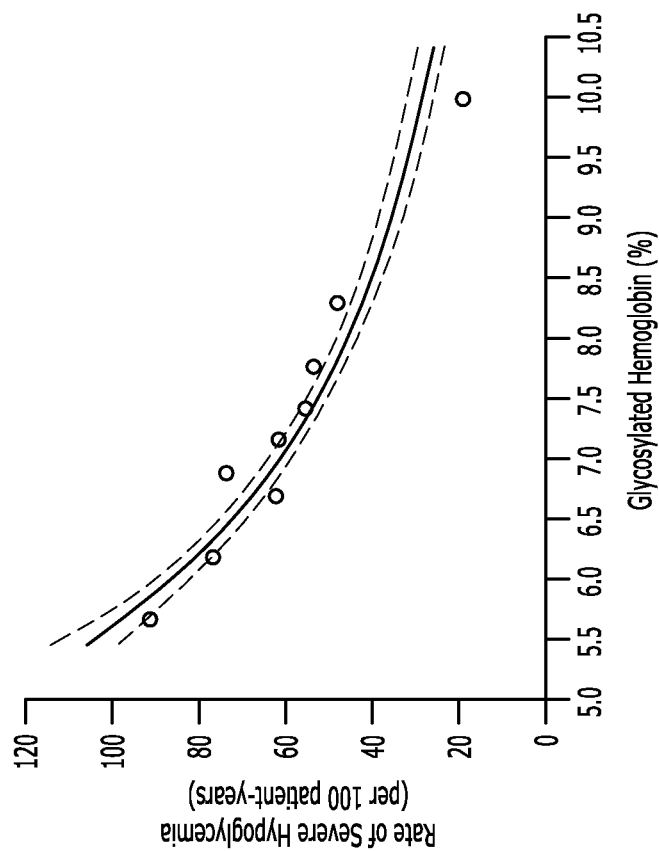
FIGS. 32A and 32B show an association between HbA1c and risk of retinopathy and HbA1c and risk of severe hypoglycemia.
Figure 32A:
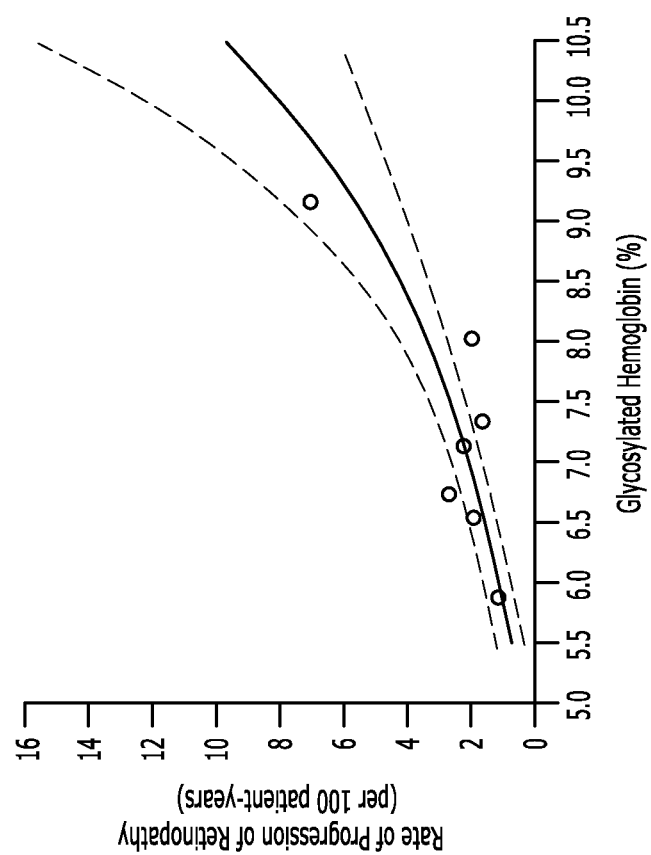

Long-term complications cause major morbidity and mortality in patients with insulin-dependent diabetes mellitus. Studies have established these clinical risks with measurable markers, where an association between long-term complications and HbA1c are often made. For example, associations between HbA1c and risk of progression of retinopathy, and between HbA1c and risk of severe hypoglycemia, are shown in FIGS. 32A and 32B.

Figure 33:
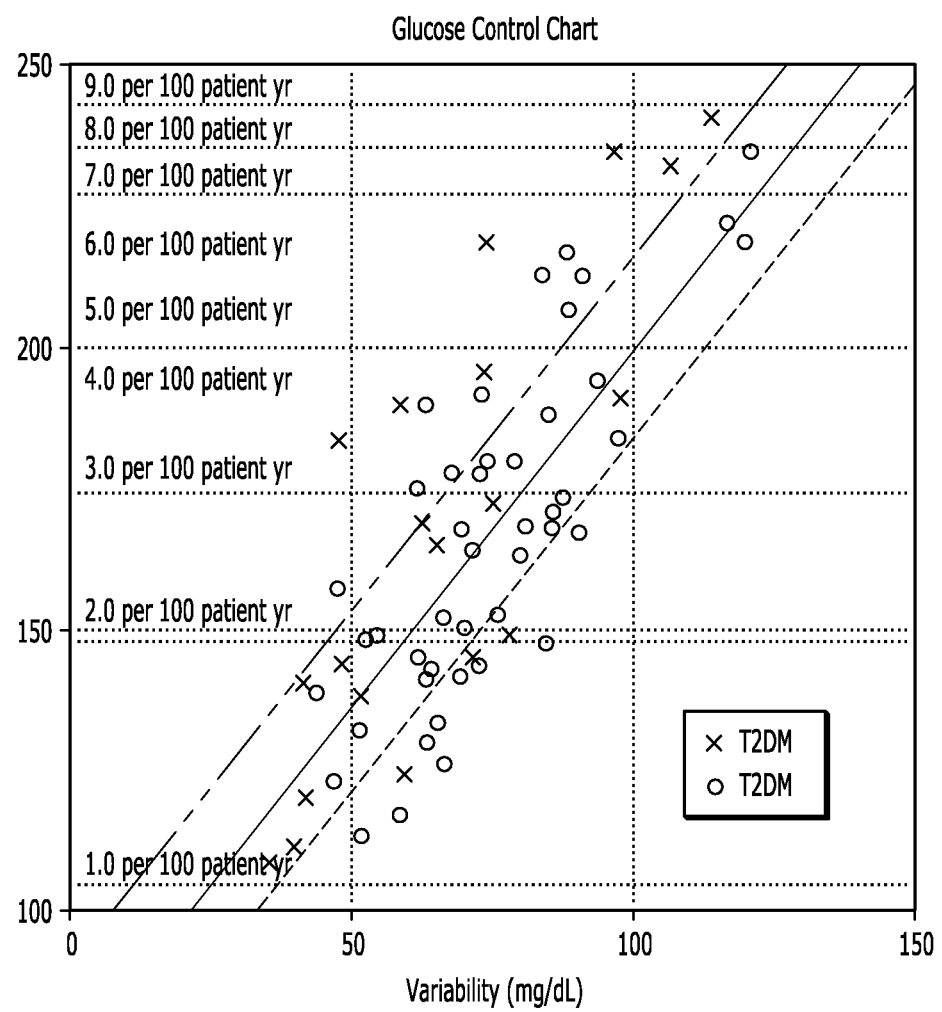
FIG. 33 shows an example of more than one clinical risk overlaid on a glucose control chart.
Figures 34A, 34B:
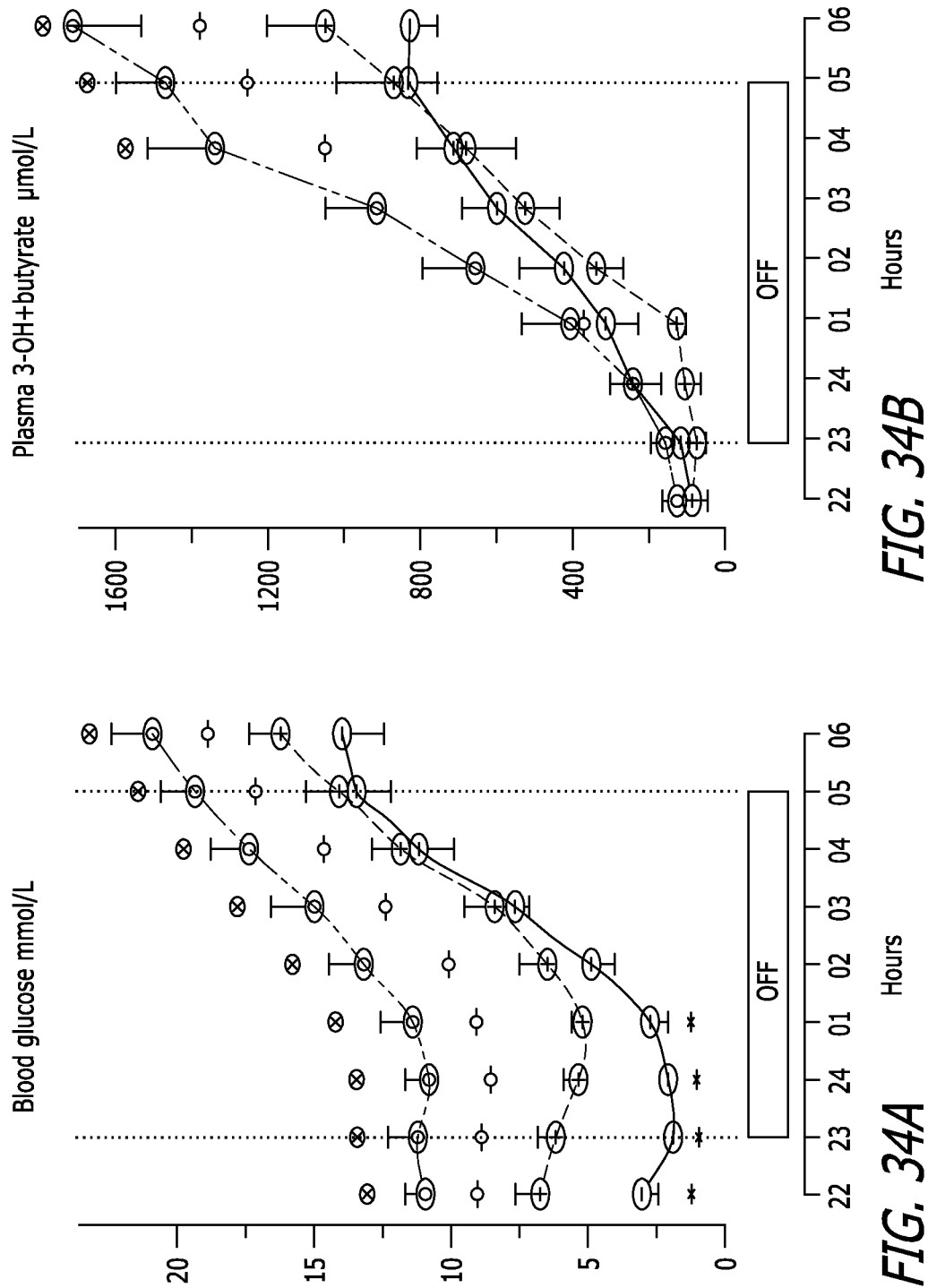
FIGS. 34A and 34B show the time relationship between glucose and β-hydroxybutyrate.

A patient's state of glucose control, represented by a single point in the glucose control chart for each patient, can be assessed relative to long term complications (that are associated with long-term exposure to high glucose) and hypoglycemia risk. The remaining two types of risk, risks associated with medium-term exposure to high glucose such as DKA, and hyperglycemia risk, requires a slightly different approach. An example of multiple risks overlaid on a glucose control chart is provided in FIG. 33.

Method to Link Medium-Term Exposure to High Glucose (e.g. DKA) to Glucose Control Chart The development of DKA risk lines require the knowledge of the number of DKA events over a fixed time period for each subject data. Then, the DKA event count over the fixed period of time, or equivalently the DKA frequency for each patient, are paired to the median and variability glucose values for each patient. A surface fit of the DKA risk (in terms of DKA frequency) is made based on these patient data.

The difference lies in obtaining the DKA frequency. Since DKA is an indirect result of glucose, where DKA occurs when a patient's -hydroxybutyrate (-OHB) level exceeds 15 mmol/L[ ], an estimate of -OHB level based on each patient's glucose time series is calculated. FIGS. 4A and 4B illustrate examples of the time relationships between blood glucose and Plasma 3-OH+butyrate (-OHB) upon suspension of insulin infusion on T1DM subjects. Using study data such as this, a linear, time invariant (LTI) transfer function model that maps glucose to -OHB can be constructed. Then, this model can be used to traverse through each patient's glucose data time series, in order to produce estimates of -OHB over the period where each patient's glucose data is available. Similar to counting the number of hypoglycemic events on the glucose time series, one can count the number of times the -OHB level exceeds 15 mmol/L. For each patient data, this results in their DKA frequency can then be further implemented to obtain DKA risk lines.

Method to Link Hyperglycemia Risk to Glucose Control Chart

Again, the development of hyperglycemia risk lines require the knowledge of the number of hyperglycemic events over a fixed time period for each subject data. Then, the hyper event count over the fixed period time, or equivalently the hyper frequency for each patient, are paired to the median and variability glucose values for each patient. Then, similar to the hypoglycemia fit, a surface fit of the hyperglycemia risk is made based on these patient data.

With lines associated with hyperglycemia risk included in the control chart, a zone of hyperglycemia risk is defined and treatment modifications may be associated with this zone. Specifically, if the median vs. variability point falls into this zone, treatment modification may be recommended to help the patient avoid this zone, similar to what has already been disclosed with regard to hypoglycemia risk zones. And like what has already be described for hypoglycemia risk zones, the Treatment Recommendation Point may be used to determine if the zone is indicated, as opposed to the best estimate of the median and variability.

Insulin Titration Using Glucose Median and Variability Metrics to Avoid Hypoglycemia Glucose median and variability are used in a "smart" insulin titration algorithm that gets patients in target faster than standard titration techniques and is less likely to cause hypoglycemia.

Insulin titration algorithms provide a means for the diabetes patient to incrementally adjust their insulin doses until their glucose levels are within target range. Titration algorithms typically rely on a very small amount of SMBG test data (for some algorithms, as few as one reading) to make titration decisions, which means that often the titration direction recommended is in error. In order to minimize the likelihood of hypoglycemia occurrences that might occur due to these recommendation errors, traditional algorithms use titration increments that are a small fraction of their total daily dose. Then if one or two titration direction mistakes occur, the net change in dose is small and unlikely to cause hypoglycemia. The result is that it can take a long time, typically twelve weeks or more, to achieve target glucose levels and optimal insulin dosing. Also, for titration algorithms that rely on episodic SMBG testing, hypoglycemia occurrences will still occur since long periods of time are not accounted for by the sparse sampling. Finally, traditional titration algorithms do not explicitly identify glucose variability problems that may be preventing successful titration to achieve glucose targets—high variability may prevent reductions in median glucose levels without causing undesirable hypoglycemia risk.

The titration algorithm invention described here uses statistical methods to provide titration guidance such that glucose targets are reached in less time, with less likelihood of hypoglycemia. The invention also provides a means to indicate to the patient and doctor when glucose variability may be preventing successful achievement of glucose targets.

Figure 35:
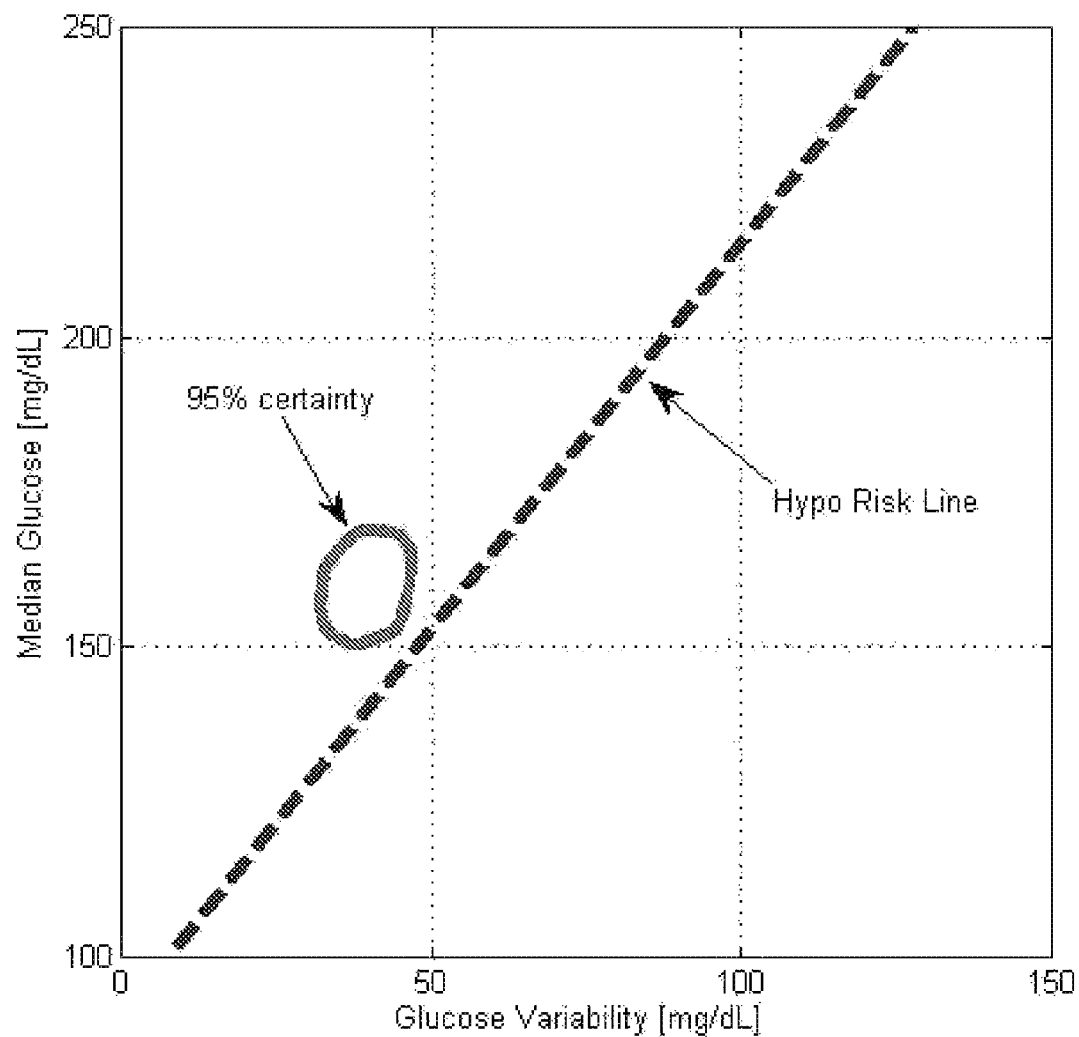
FIG. 35 shows a control grid of a patient's current glycemia state with a "Hypo Risk Line" with at least 95% certainty of no hypoglycemia risk.

The "control grid" is a technical method used to generate treatment recommendations from glucose readings. The control grid is a plot of median glucose Gm vs. glucose variability Gv (for example, the distance between the median to the lower 10th percentile), with sections defined that are attributed to glucose recommendations. One important aspect of the control grid is referred to as the "Hypo Risk Line" (FIG. 35). This line is associated with an expected number of hypoglycemia occurrences for a given glucose median and variability. In addition, along with the best estimate of the median and variability, the 95% certainty "bubble" can be plotted on the control grid—if this bubble is above the hypo risk line, then the patient should anticipate, with 95% certainty, not to exceed the frequency of hypoglycemia occurrences associated with the hypo risk line (otherwise referred to as the "Hypo Risk Tolerance"). The point on the bubble closest to the hypo risk line is the "Treatment Recommendation Point" or TRP. If the TRP is above the hypo risk line, then the recommendations are consistent with safely increasing insulin or other medications that are known to cause hypoglycemia. If the TRP is below the hypo risk line, then the recommendations are consistent with either decreasing insulin or not adjusting insulin, and/or taking steps to reduce glucose variability. (Note that the "certainty bubble" concept is only used as an intuitive graphical illustration as does not exactly describe how the 95% certainty calculation is performed.)

The vertical difference between the TRP and the hypo risk line is referred to as the Margin To Treat (MTT). For a given glucose variability, a positive value for the MTT (that is, the TRP is above the hypo risk line such as illustrated by the vertical distance marked by the δ in FIG. 36) corresponds to the amount of reduction in the median glucose that can occur before the TRP crosses below the hypo risk line. This can be associated with the amount of insulin increase allowed before causing a high risk of hypoglycemia, as defined by the hypo risk line. A negative value for the MTT (such as illustrated by the vertical distance marked by the red δ in FIG. 36) corresponds to the amount of increase in the median glucose needed for the TRP to be above the hypo risk line and is associated with the amount of insulin decrease needed to transition to a low risk of hypoglycemia.

This invention utilizes the MTT as the metric to drive insulin titration, in such a way to manage the risk of hypoglycemia. The MTT would be calculated at the end of each titration period based on the glucose readings measured during this period, and the MTT would be used to determine the insulin change recommendation. Another titration period would commence where more glucose readings would be received, and at the end of the period, again the MTT would be calculated and used to determine the insulin change recommendation, and so on.

The advantage of using the MTT is that it not only provides the direction of the titration (increase or decrease) but also amount of the titration, in the form of desired glucose median change. Since the glucose for different diabetes patients responds differently for a given change in insulin dosage, the MTT cannot be used directly to drive titration amount. Another aspect of this invention is that the titration algorithm will learn how a change in insulin affects the median glucose for a specific patient, and will use this measured affect to convert the MTT to a specific insulin change amount. In the first embodiment, the first titration amount may be preset to correspond to a conservative value defined by predetermined patient information such as patient weight or known insulin sensitivity, or it may be defined as a conservative value based on a worse case physiological model of a patient (that is, the most insulin sensitive). For a subsequent titration, the insulin titration sensitivity (ITS) may be estimated as the change-in-median-glucose/change-in-insulin. The insulin change recommendation for this titration could then be calculated as MTT/ITS; however, it would be safer, since the ITS is an estimate, to reduce the insulin change by taking into account the uncertainty in the ITS estimate.

Estimating a Varying ITS Value Over Time

Alternatively, the ITS value can be refined over time based on past patient data and a priori population information. Let median glucose measurement Gm(k) be computed and stored at every titration period index k. Let the insulin dose I(k) be stored at every titration period index k. Let the latest ITS value γ(k) be a function of Gm and I at the latest and previous titration period indices k and k−1:

$$\gamma(k) := \frac{Gm(k) - Gm(k-1)}{I(k-1) - I(k)} \quad [1]$$

Then, for the next titration period index k+1, the recommended insulin dose I(k+1) is equal to the latest dose I(k) plus an adjustment factor:

$$I(k+1) = I(k) + \frac{Gm(k) - Gm(k+1)}{\gamma(k+1)} \quad [2]$$

Note that in Eqn. 2, the ITS value γ(k+1) for the next titration period is not directly known, hence an estimate, $\hat{\gamma}(k+1)$, must be made. The estimation of γ(k+1) is deferred after other elements of the recommended insulin dose, I(k+1), for the next titration period has been determined.

Figure 36:
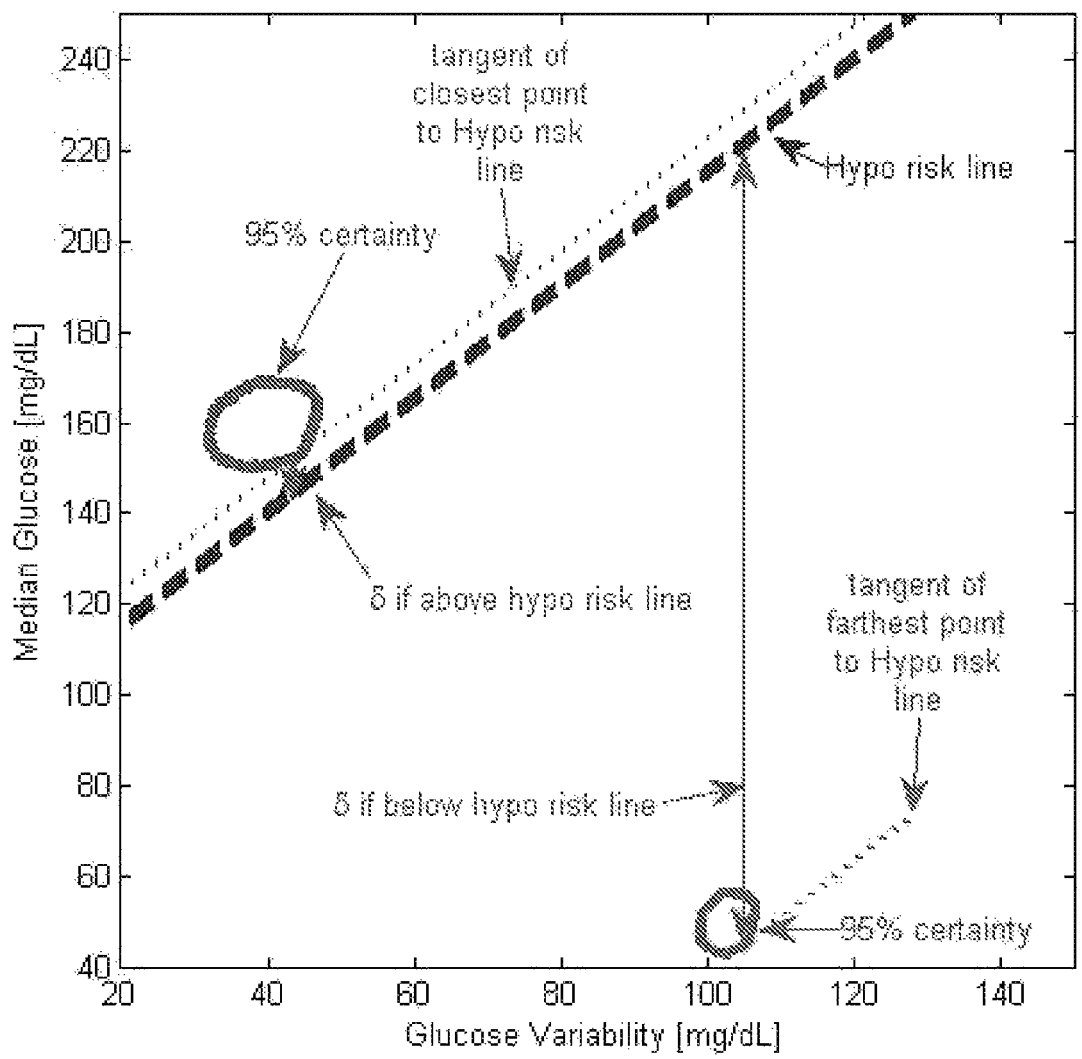
FIG. 36 shows the sign of the MTT value being positive or negative, depending on patient data relative to hypo risk line.

Let the MTT value for the next titration period be represented by δ(k+1), as computed by the glucose control chart-based strategy defined above and illustrated in FIG. 36. Then, we would like for the next median glucose Gm(k+1) to change from the latest median glucose Gm(k) in the amount specified by δ(k+1). The target median for the next titration period, Gt(k+1), is then:

$$Gt(k+1) := Gm(k) - \delta(k+1) \quad [3]$$

Setting the next Gm value (i.e. Gm(k+1)) to equal the MTT-derived target value Gt, and substituting the ITS value for the next titration period with its estimate $\hat{\gamma}(k+1)$ (yet to be defined), one can compute the next titration dose I(k+1):

$$I(k+1) = I(k) + \frac{Gm(k) - Gt(k+1)}{\hat{\gamma}(k+1)} = I(k) + \frac{\delta(k+1)}{\hat{\gamma}(k+1)} \quad [4]$$

i.e.

$$I(k+1) = I(k) + \Delta(k+1), \Delta(k+1) = \frac{\delta(k+1)}{\hat{\gamma}(k+1)}$$

Estimating a Varying ITS Value Over Time Using a Moving Average of Past Values

In the second embodiment, estimation of the ITS value for the next titration period is obtained from the moving average of N past computed ITS values:

$$\hat{\gamma}(k+1) := \frac{1}{N} \sum_{j=k-N}^{k} \gamma(j), \quad \gamma(k) \geq 0 \quad [5]$$

In other words, the next insulin dose is calculated by using Eqn. 4, where the next ITS value is determined by Eqn. 5, and the next MTT is determined by the control grid.

Figure 37:
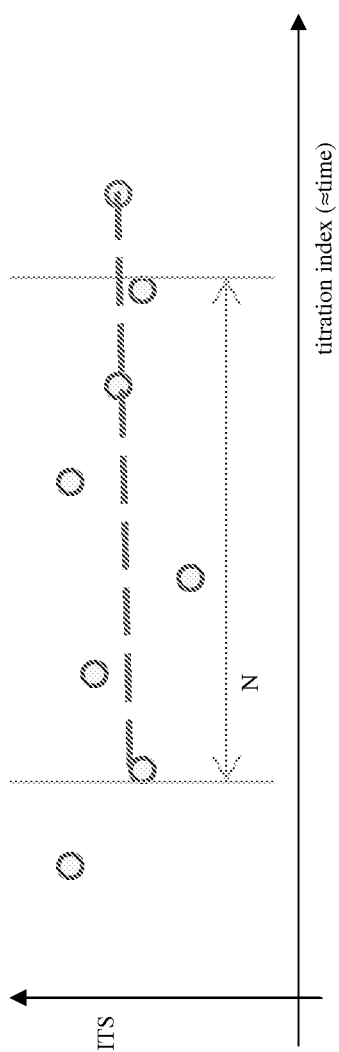
FIG. 37 presents a one-step projection of a straight line fit based on past data.

Estimating a Varying ITS Value Over Time Using a One-Step Prediction Based on Past Values In the second third embodiment, the estimation of the ITS value for the next titration period is obtained from the projected straight line Least-Squares (LS) Error fit of N past computed ITS values (FIG. 37). In other words, the next insulin dose is calculated by using Eqn. 4, where the next ITS value is determined by the projected LS error fit as illustrated in FIG. 37, and the next MTT is determined by the control grid.

Using MTT to provide fixed step dose changes

In the third fourth embodiment, the ITS value and MTT are used to provide a fixed set of increments depending on the HCP's assessment of the patient's ITS value, combined with the MTT sign (i.e. positive or negative) is used to determine a fixed amount. The result is a progression of titration changes that are more similar to current MD-based consensus guidelines. For example:

$$I(k+1) = I(k) + \Delta(k+1) \quad [6]$$

Where, if the HCP deems the patient's ITS to be on the extremely low side, $\Delta$ is determined by:

$$\Delta(k+1) = \begin{cases} +1U & \text{if } \delta(k+1) > 20 \text{ mg/dL} \\ -1U & \text{if } \delta(k+1) < 10 \text{ mg/dL} \\ 0 & \text{otherwise} \end{cases} \quad [7]$$

Note that the decision to choose the values +1 and −1 units, as well as at least a 20 mg/dL MTT for a dose increase and a −10 mg/dL MTT for a dose decrease depends on the HCP's expertise. The determination of whether a patient's ITS (which can be computed by either the moving average of N past values, projected LS error fit of the N past values, etc.) is on par with the population average or not primarily depends on the HCP's assessment of the patients insulin sensitivity factor and the patient's past propensity for observed or symptomatic hypoglycemia. Alternatively, these values can also be set a priori based on population study data. A mechanism similar to the ADA/EASD consensus guideline can also be adopted:

$$I(k+1) = I(k) + \Delta(k+1) \quad [8]$$

$$\Delta(k+1) = \begin{cases} +4U & \text{if } 50 < \delta(k+1) \text{ mg/dL} \\ +2U & \text{if } 0 < \delta(k+1) \leq 50 \text{ mg/dL} \\ 0 & \text{if } \delta(k+1) = 0 \text{ mg/dL} \\ \min(-4U, -0.1I(k)) & \text{otherwise} \end{cases} \quad [9]$$

Figure 38:
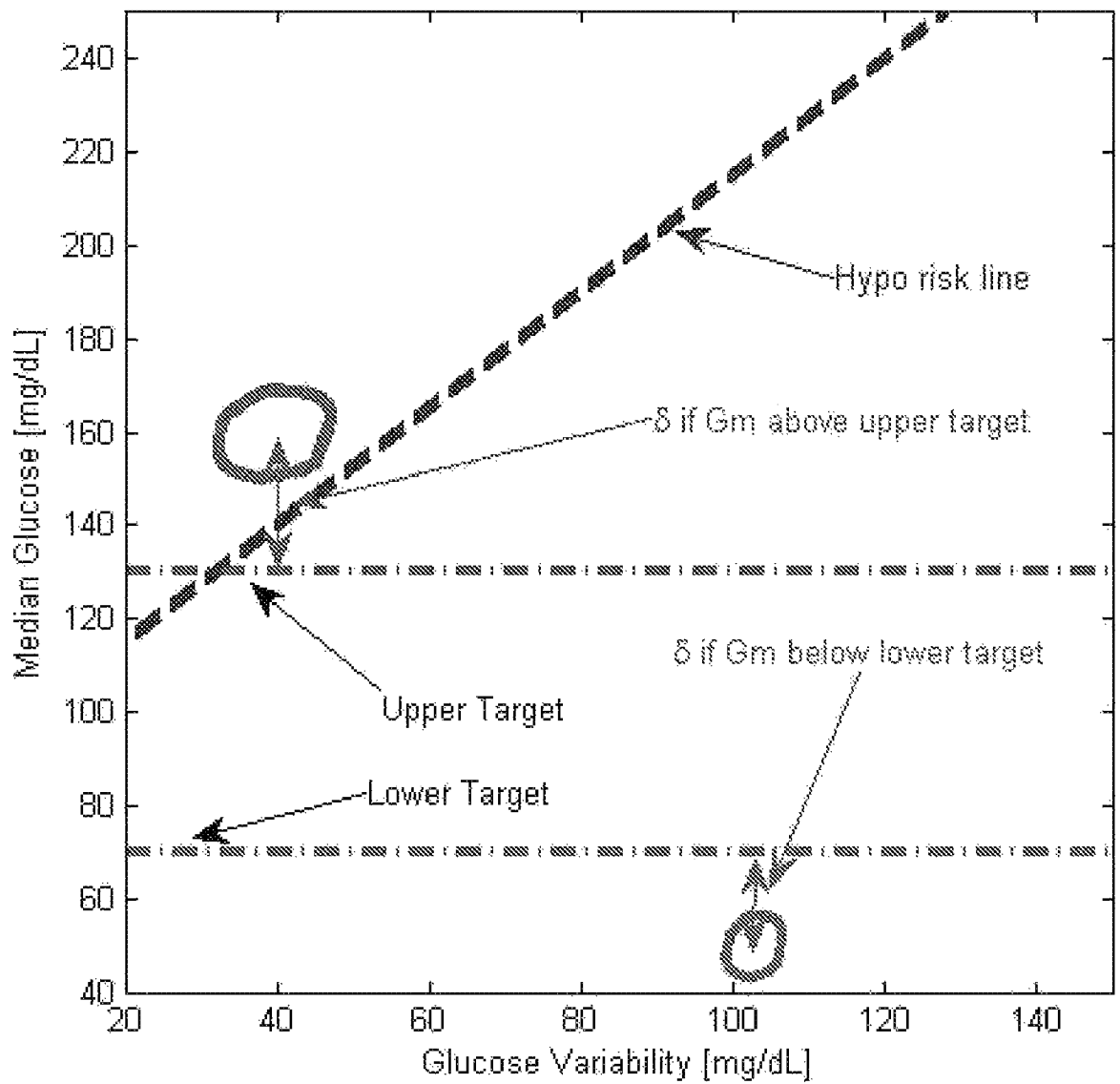
FIG. 38 is an illustration of the ADA/EASD consensus guideline.

The primary difference between the embodiment described in Eqns. 8 and 9 and that of the ADA/EASD consensus guideline is that in the consensus guideline, the MTT is based solely on the median glucose, and takes no consideration of the risk of hypoglycemia due to the patient's glycemic variability. For comparison, the consensus guideline is charted into the control grid (FIG. 38), where the single hypo risk line has been replaced by the upper and lower target glucose ranges at 130 (green dash-dot line) and 70 (red dash-dot line) mg/dL values, and the use of the 95% confidence has been replaced by either a measurement average or any one measurement below 70 mg/dL. Whenever Gm is within the 2 target limits, $\delta$ is assumed to be 0.

Providing an Adaptive Safety Factor when Increasing Dose

In the fifth embodiment, an additional safety element based on the variability of ITS over many periods are used to reduce the chance of an excessive dose increase. The safety element involves adding a multiplicative safety factor $\alpha$, which is varied over time to accommodate for the patient's changing situation. A preferred embodiment of this safety element modifies Eqn. 4 as follows:

$$I(k+1) = I(k) + \Delta(k+1) \quad [10]$$

$$\Delta(k+1) = \begin{cases} \alpha(k+1)\dfrac{\delta(k+1)}{\hat{y}(k+1)} & \text{if } \delta(k+1) > 0 \\ \dfrac{\delta(k+1)}{\hat{y}(k+1)} & \text{otherwise} \end{cases}$$

Note that the safety factor only affects dose increase, in the sense that large ITS variability reduces the certainty of the information, which may increase the risk of unmodeled hypoglycemia. As a result, what was deemed to be a safe dose increase may need to be slightly attenuated. The safety factor can start at a neutral value of 1, which makes both possibilities described in Eqn. 10 above identical. In the preferred embodiment, the safety factor is computed relative to an a priori baseline ITS variability vb:

$$\alpha(k+1) = \dfrac{1}{1 + \left[\dfrac{v(k)}{vb}\right]^2} \quad [11]$$

Where the latest variability v(k) is computed from the standard deviation of the past N ITS values relative to the best fit line as described in FIG. 37. Alternately, the baseline ITS variability can be computed online based on ITS values over a longer horizon N2 (N2>>N).

Accounting for Changes in Glucose Variability Between Titrations

In the five embodiments described, the determination of the Margin To Treat (MTT) value for the next titration period index k+1, $\delta$(k+1), is computed with the assumption that the "certainty bubble" is wide enough to account for slight changes in the patient's glucose variability Gv between the latest and next titration periods. In other words, any changes in basal insulin dose will only affect Gm, and treatment uncertainties due to changes in Gv is accounted for by the "certainty bubble". The following 3 embodiments account for changes in Gv when determining the next basa insulin dose I(k+1).

Accounting for Changes in Glucose Variability Between Titrations Via a Simple Decoupled Model In a sixth embodiment, the progression of the patient's glucose variability Gv is tracked in order to estimate the amount of change in glucose variability. This process can be similar to the estimation/one step projection of ITS as depicted in FIG. 37. The difference is instead of using past ITS to predict the next ITS value, the fifth embodiment uses past Gv to predict the next Gv. This information can then be used to adjust the MTT, by replacing Gv(k) of the latest "certainty bubble" with the predicted Gv(k+1) value, thereby shifting the patient's glucose control value to the left or right based on the difference in Gv. Afterwards, basal insulin is assumed to only affect Gm. Hence, MTT and the rest of the calculation can be performed as before.

Accounting for Changes in Glucose Variability Between Titrations Via a Coupled Insulin Sensitivity Gradient Model In a seventh embodiment, the adjustment of MTT value to account for glucose variability relies on the estimation of an insulin titration gradient (ITG), Γ, finding a lowest point in the "certainty bubble" from the latest titration index k from a possibility of points whose tangent line is parallel to the Hypo risk line, and finally calculate the recommended insulin dose I for the next titration index. The details are outlined as follows.

In the foundation of the prior embodiments, it was assumed that a change in basal insulin I affects the patient's median glucose Gm, but not glucose variability Gv. As a result, the notion of insulin titration sensitivity relates changes in I to changes in Gm. In a more comprehensive model, this one-dimensional concept is replaced by an insulin titration gradient, where the vertical component is identical to the definition of ITS, and the horizontal component relates changes in I to changes in Gv. In other words:

$$\Gamma(k) := \frac{Gv(k) - Gv(k-1)}{I(k-1) - I(k)} e_x + \frac{Gm(k) - Gm(k-1)}{I(k-1) - I(k)} e_y \quad [12]$$
$$= \Gamma_x(k) e_x + \Gamma_y(k) e_y$$

Figure 39:
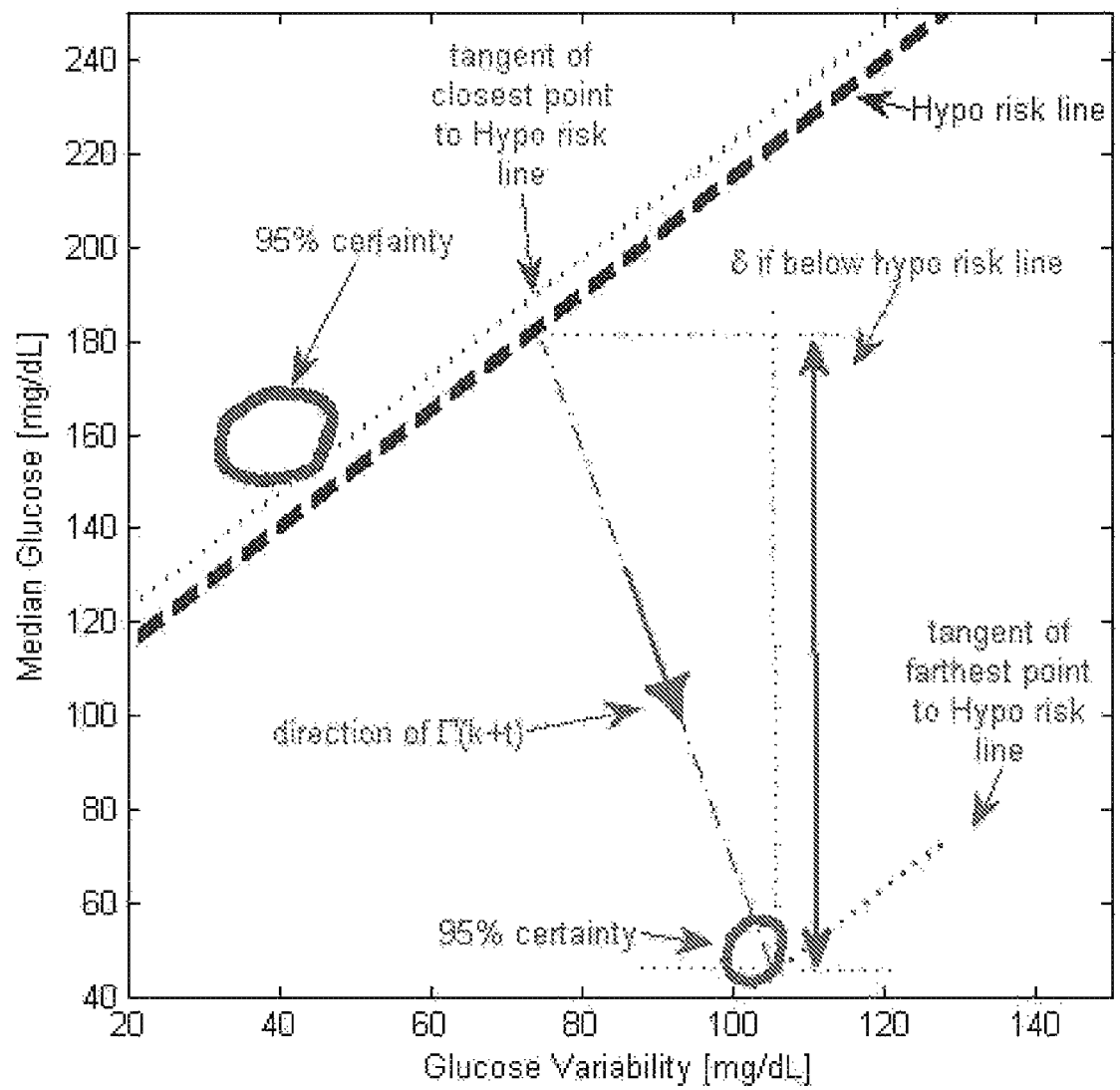
FIG. 39 shows a determination of MTT taking into account both median glucose and glucose variability and vector adaptation.

The effect of basal insulin I is now a vector that spans the horizontal basis $e_x$ representing glucose variability, and the vertical basis $e_y$ representing median glucose. Both $e_x$ and $e_y$ are unity vectors. This vector adaptation to the basic principle for the four example embodiments illustrated in FIG. 36 is illustrated in FIG. 39.

Take candidate points in the "certainty bubble" whose tangent (red dotted line) parallels the Hypo risk line, and pick one with the smallest median glucose value. For the moment, assume Γ(k+1), the value of ITG for the next titration index, has been estimated, and has the direction as depicted by the red arrow in FIG. 39. Then, extend the previously selected point towards the Hypo risk line along the direction of γ(k+1). The vertical component is similar to the original MTT as described in the first four embodiments. However, the value of MTT (represented by the distance δ in FIG. 39) is somewhat shorter than the similar situation depicted in FIG. 36. The reason is that in the vector case, any non-vertical effect of changing insulin dose can reduce or increase the likelihood to crossing the Hypo risk line.

Similar to the original scalar case (i.e. the first five embodiments), the recommended insulin dose I(k+1) equals the latest dose I(k) plus an adjustment factor:

$$I(k+1) = I(k) + \frac{Gm(k) - Gm(k+1)}{\hat{\Gamma}_y(k+1)} \quad [13]$$

Where $\hat{\Gamma}_y$ (k+1) is the estimate for the vertical component of ITG, to be defined. The target median glucose depends on the latest median glucose Gm(k) and the MTT represented by the length δ in FIG. 39:

$$Gt(k+1) := Gm(k) - \delta(k+1) \quad [14]$$

Then, setting the next Gm value (i.e. Gm(k+1)) to equal the MTT-derived target value Gt, and substituting $\Gamma_y$(k+1) value for the next titration period with its estimate $\hat{\Gamma}_y$ (k+1) (yet to be defined), one can compute the next titration dose I(k+1):

$$I(k+1) = I(k) + \Delta(k+1), \Delta(k+1) = \frac{\delta(k+1)}{\hat{\Gamma}_y(k+1)} \quad [15]$$

In this embodiment, estimation of the vertical component of the ITG value for the next titration period is obtained from the moving average of vertical components of N past ITG values:

$$\hat{\Gamma}_y(k+1) := \frac{1}{N} \sum_{j=k-N}^{k} \Gamma_y(j), \quad \Gamma_y(k) \geq 0 \quad [16]$$

The horizontal component of the ITG value could also be independently computed in a similar manner:

$$\hat{\Gamma}_x(k+1) := \frac{1}{N} \sum_{j=k-N}^{k} \Gamma_x(j), \quad \Gamma_x(k) \geq 0 \quad [17]$$

Accounting for changes in glucose variability between titrations via a coupled insulin sensitivity gradient model, with a coupled estimation of the insulin sensitivity gradient model.

In an eighth embodiment, the process is identical to the seventh embodiment, with the exception of a joint estimation of the vertical and horizontal components of the ITG value. A preferred implementation is to define a polar representation of ITG:

$$\Gamma_m(k) := \sqrt{[\Gamma_x(k)]^2 + [\Gamma_y(k)]^2} \quad [18]$$
$$\Gamma_r(k) := \frac{\Gamma_x(k)}{\Gamma_y(k)}$$

Where the ratio is selected such that singularity is avoided by not placing the typically smaller element, $\Gamma_x$, on the denominator. Following this polar representation, one-step predictions of the magnitude $\Gamma_m$ and ratio $\Gamma_r$ can be conducted by independently applying the same LS error fit of a line depicted in FIG. 3, replacing the ITS by $\Gamma_m$ and $\Gamma_r$ in each case, independently.

Variability: The system would notify the patient and/or HCP when variability was too high and needed to be reduced if they wanted to achieve a lower target medium. Specifically, the system would output: a) lowest median achievable for current variability, and b) variability target needed to achieve median target. The variability would be indicated as too high if the MTT was greater than the difference between the current TRP and the desired median. This output would most beneficially be made to the patient's HCP so they could work with the patient to address self-care behavior to address variability. A target variability could also be provided, which in one embodiment may be calculated as the intersection of the hypo risk line and the target median.

Using methods described in any of the embodiments, the lowest median achievable $\hat{G}m(k+1)$ given the current variability is equal to the target median glucose used in the calculations, as outlined in Eqns. 3 and 14:

$$\hat{G}m(k+1):=Gt(k+1) \quad [19]$$

The variability target $\hat{G}v(k+1)$ needed to achieve median target can be computed in the seventh and eighth embodiments by taking I(k+1) (the suggested insulin dose), $\hat{\Gamma}_x(k+1)$ (the estimated horizontal component of the ITG), I(k) (the latest measured insulin dose), and Gv(k) (the latest glucose variability), in the following manner:

$$\hat{G}v(k+1)=Gv(k)+[\hat{\Gamma}_x(k+1)[I(k)-I(k+1)]] \quad [20]$$

Basal vs. basal/bolus: The algorithm described thus far could apply to glucose lowering medications and specifically medications that can cause hypoglycemia, such as basal insulin and sulfonyurea. Extending this algorithm to basal and prandial dose insulin is more complicated, as there are four key dosing times-per-day, each associated with a glucose profile time-per-day: fasting, post-breakfast, post-lunch and post-dinner (note that other dosing regimens may be considered here more generally). A control grid would be determined for each period. One approach for this more complicated dosing is to incorporate a basal/bolus interaction model into the titration algorithm. A basal/bolus interaction model would take into account that the basal dose impacts not only fasting glucose but also post-meal glucose, and that the rapid-acting dinner dose often impacts the fasting glucose. A simple interaction model could associate the long-acting dose with an apportioned effect on each of the four time-of-day median glucose levels: for instance, an incremental insulin sensitivity could be determined for each time-of-day period associated with the basal dose (mg/dL per unit) Likewise, the dinner and fasting periods could have in incremental insulin sensitivity associated with the rapid-acting dinner dose.

Meter vs. PC Software vs Hybrid: This system can be implemented any number of ways. For instance, it may be implemented fully on a glucose meter. It is likely that the meter would have features that allowed an HCP or other caregiver to configure the titration parameters, such as maximum titration levels or other possible parameters for the algorithm. The algorithm could also be implemented fully on a personal computer or other non-meter computing device or remotely in the "cloud". Here the HCP may be involved to approve the titration recommendations. A hybrid system can be contemplated where portions of the algorithm are available either on the meter and/or on the remote computing device. One example of this embodiment is where the algorithm is implemented remotely, and an HCP is notified of the titration recommendation and must approve it. The remote computer would then download the titration recommendation. Many other variations of this hybrid scheme can be contemplated.

Simplified Expert Algorithm for Therapy Management System Informatics System

An embodiment related to a Therapy Management System (TMS) is disclosed. In the prior art, an "Expert Algorithm" calculates the numerical results that drive the treatment recommendations. The prior art algorithm is numerically complex and takes a significant amount of time to produce results. The waiting time is noticeable and detracts from the user's experience.

In particular, the calculation of the uncertainty in the estimate takes a substantial amount of computation time. The uncertainty is used to find the distance from the center value to a value called the "Treatment Recommendation Point" (TRP), which is vital to the operation of the TMS. Twice this distance is known as the "Figure of Merit" (FOM). This embodiment uses the results of the current expert algorithm to make a simple approximation to the FOM, thus bypassing a lengthy calculation.

Figure 40:
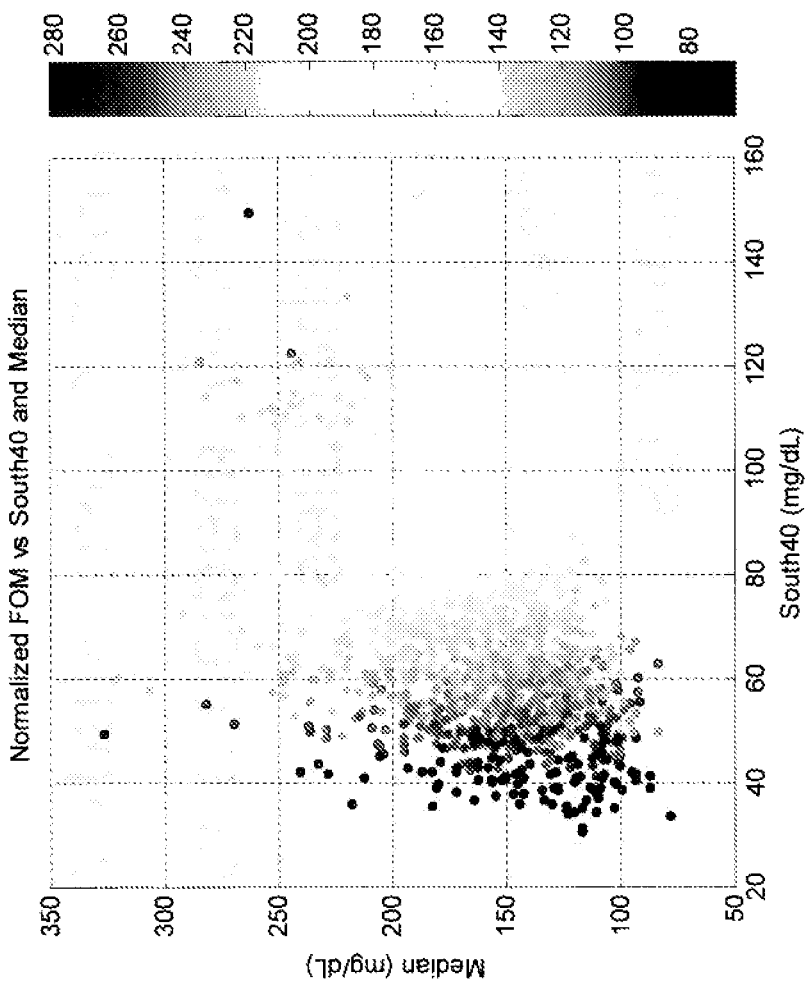
FIG. 40 is a scatter plot of FOM vs. south40 and median.
Figure 41:
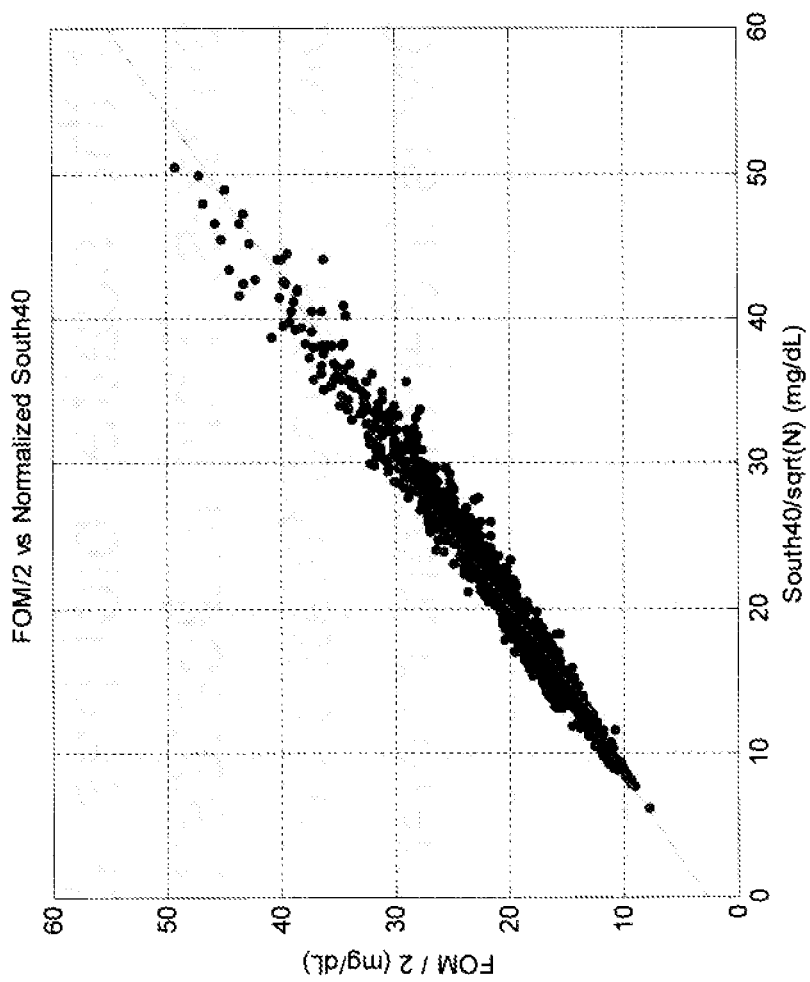
FIG. 41 is a scatter plot of FOM/2 vs. normalized south40.
Figure 42:
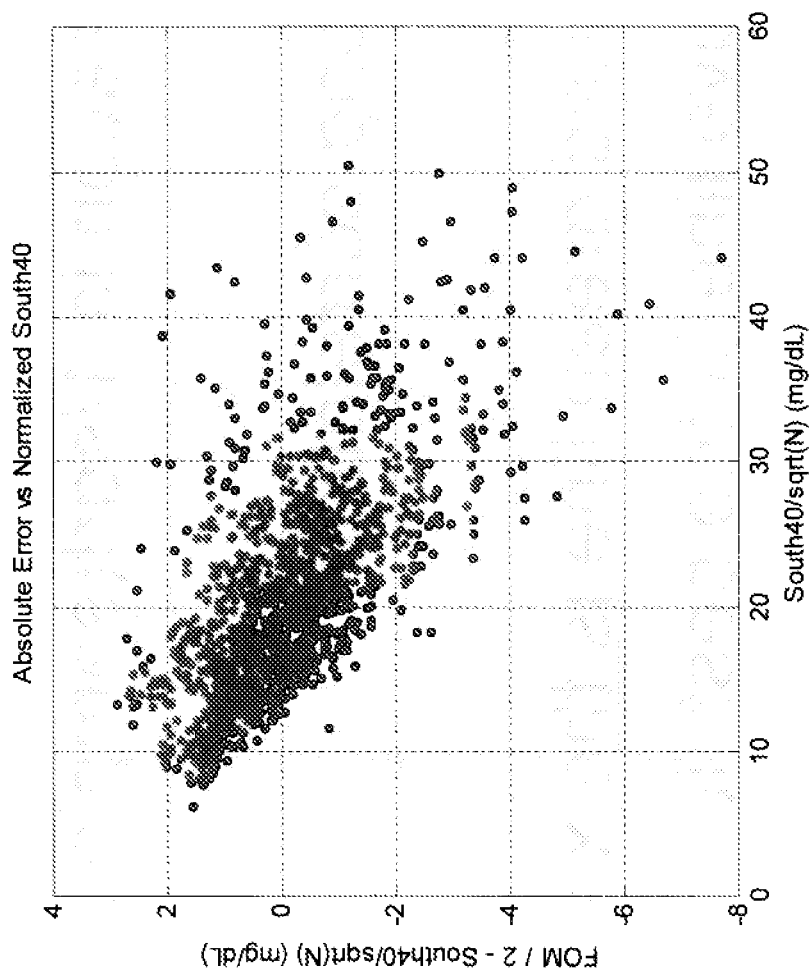
FIG. 42 is a scatter plot of error using FOM/2=south40/√N.
Figure 43:
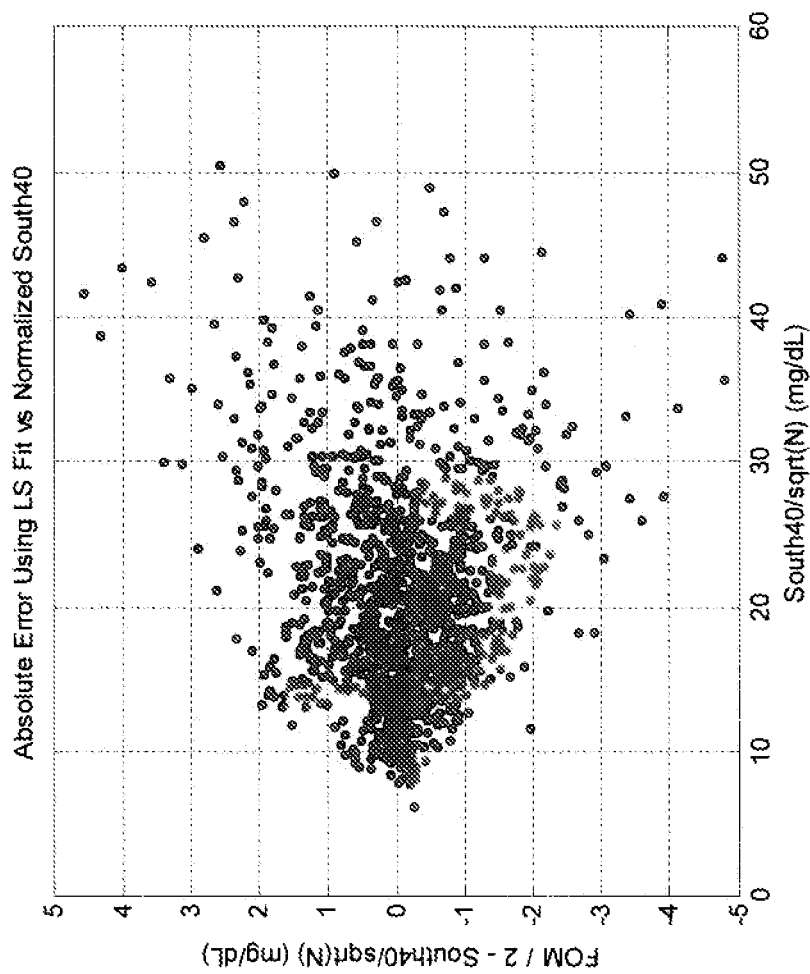
FIG. 43 is a scatter plot using least squares fit.
Figure 44:
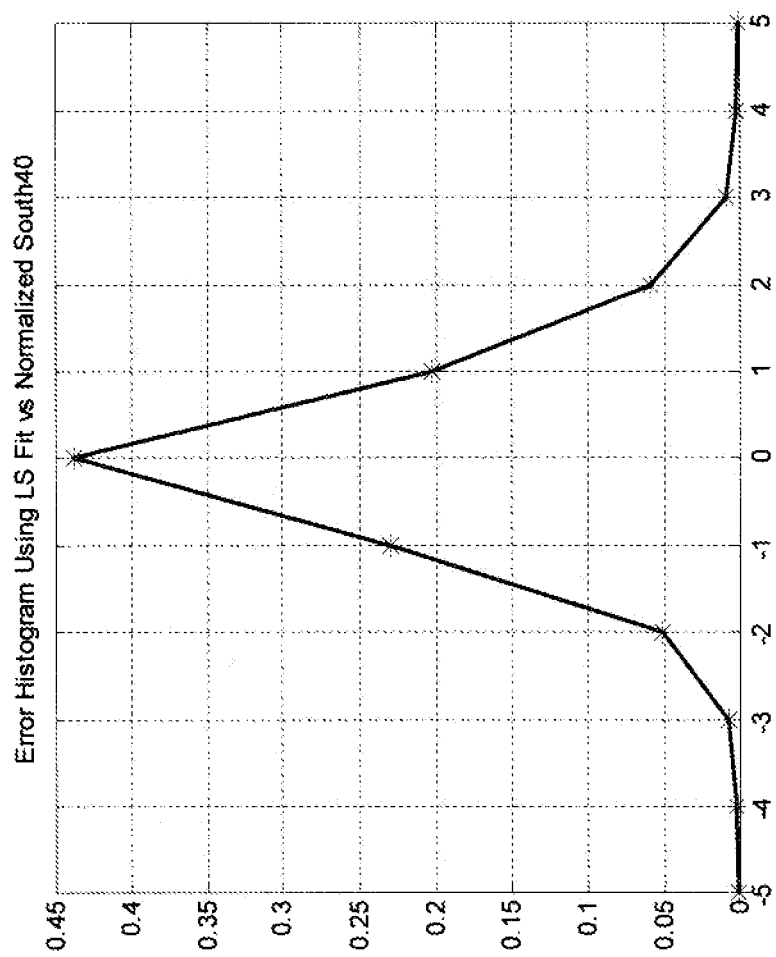
FIG. 44 is an error (with LS fit) histogram showing an error histogram using LS fit vs. normalized south 40.

Referring to the drawings, FIG. 40 shows a scatter plot of the figure of merit vs. the South40 and the glucose median. The scatter plot has strong vertical stripes which indicates that the FOM is a strong function of the south40 and the FOM is independent of the median. FIG. 41 presents a FOM/2 vs. the normalized South40. The normalization is 1/the square root of the sample size. A very strong correlation is apparent. The dashed line is the x=y line. The second line is the best fit and is slope=0.8745 and intercept=2.57 mg/dL. FIG. 42 presents the error using the FOM/2-S40/square root of sample size. FIG. 43 presents the error using a least squares fit. FIG. 44 shows the error with the least squares fit histogram. By using the least squares fit, there are no errors larger than 5 mg/dL and the errors are symmetrical about 0.

As shown in FIGS. 40 through 47, there is a very strong linear relationship between the FOM, and the glucose variability (the "South40") and the number of data points, N. Using a linear regression, we find that $$FOM/2=2.57+0.8745*South40/\sqrt{N},$$

Thus, 5-10 seconds of calculation can be replaced by a few arithmetic operations. This relationship was tested on a different set of data (the Test Set). The error between the calculated FOM/2 and the approximated FOM/2 rarely exceeds 5 m/dL, which is much smaller than the FOM itself.

Figure 45:
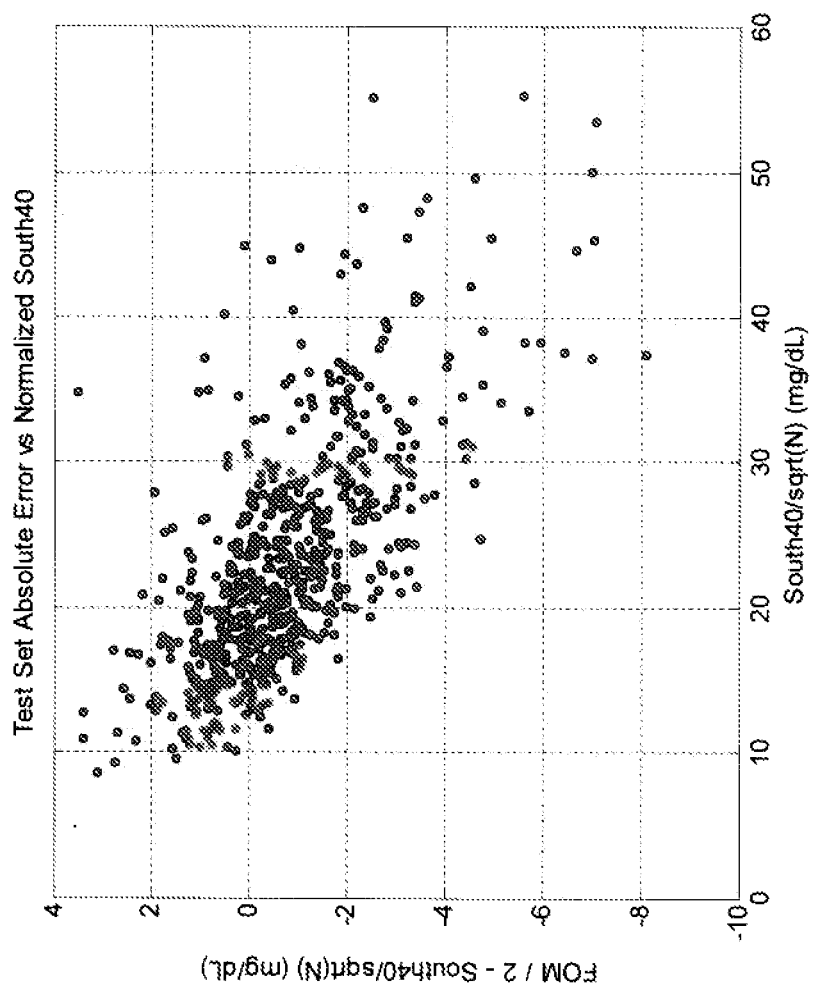
FIG. 45 is a scatter plot of test set data showing error using FOM/2=south40/√N.
Figure 46:
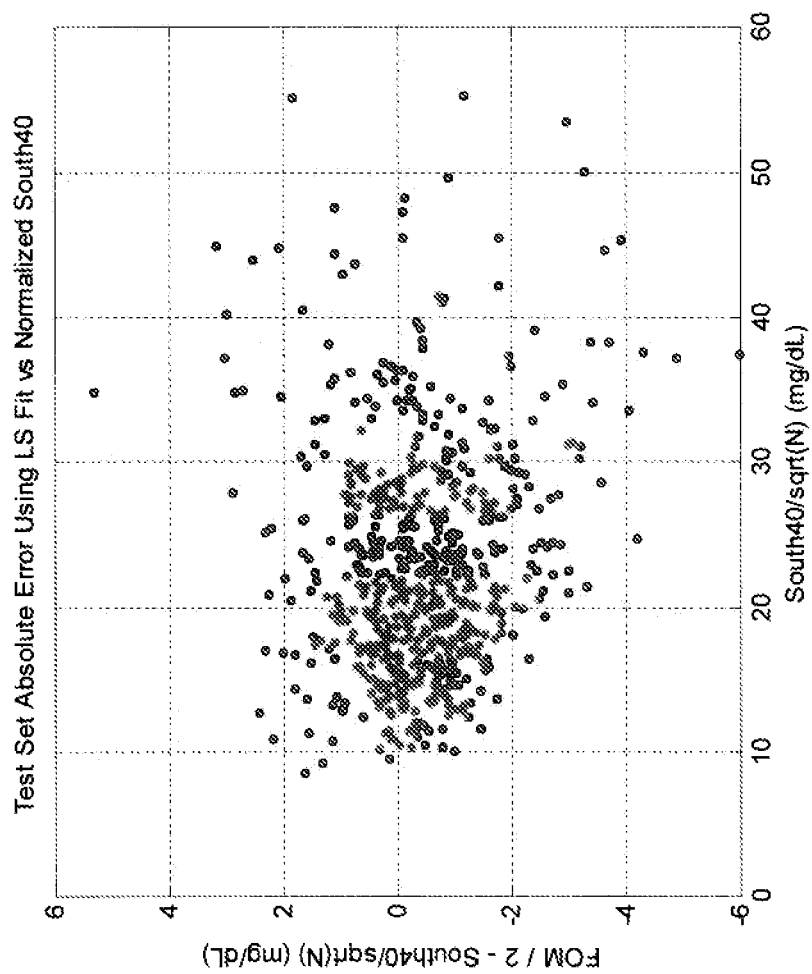
FIG. 46 is a scatter plot of test set data showing error using least squares fit.
Figure 47:
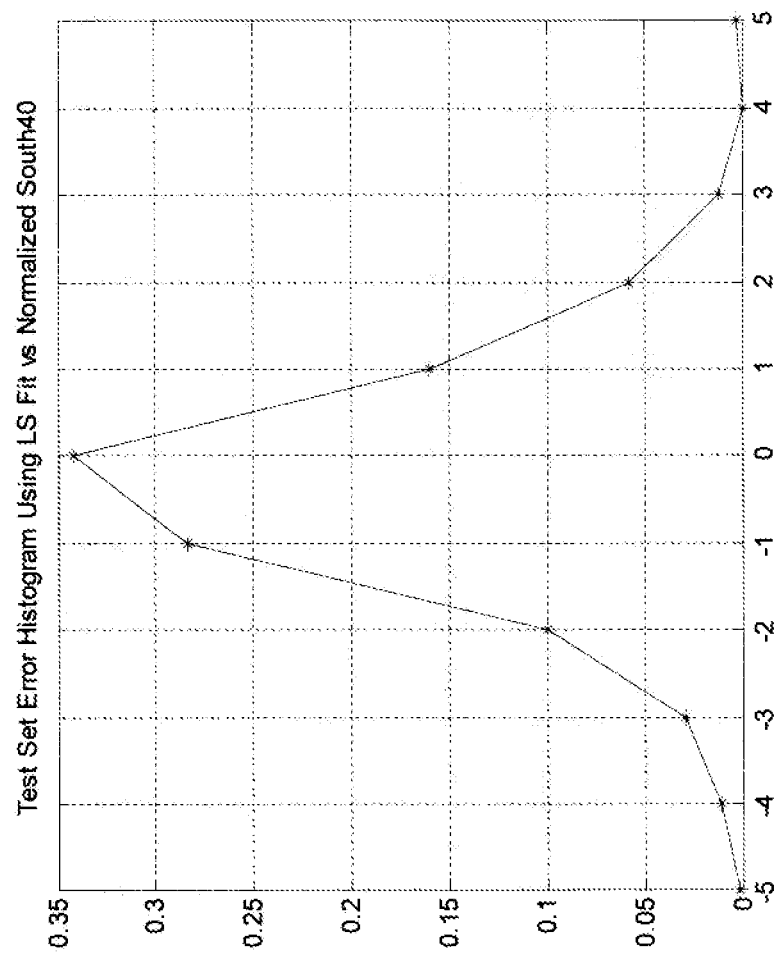
FIG. 47 is an error (with least squares fit) histogram of test set data showing a test set error histogram using a least squares fit vs. a normalized south40.

FIGS. 45 through 47 are based on test set data and FIG. 45 shows the error using the FOM/2=S40/square root of the sample size. FIG. 46 shows the error using the least squares fit, and the graph of FIG. 47 shows the error with the least squares fit histogram. The test set indicates that the correlation persists, and that the error is small.

Use of Meal Markers and Glucose Pattern Analysis to Improve Treatment Recommendations Using meal markers and/or glucose patterns to drive patient treatment recommendations. Previous recommendation systems do not use meal information and also do not exploit temporal relationships between glucose values. Use of meal markers can be used to give more targeted (and thus better) recommendations. Pattern analysis using temporal relationships opens up new analysis results that would have been missed when only looking at the collected data in aggregated form.

Meal markers could be used in many ways. Using them to bin data (e.g. post-Lunch values are those values after a recorded meal event between 10 am and 3 pm) would allow more accurate differentiation of points into meal 'bins', leading to more accurate recommendations for meal-specific problems. Recorded meal size and timing relative to insulin usage can be used to evaluate how well the patient is currently managing meals and suggest either overall (i.e. all meals) or targeted (i.e. only some meals) behavior improvements to improve glycemic control/reduce variability. Meal marker information can be collected in a variety of ways:

Explicitly (i.e. there is UI to allow the user to record a meal);

Implicitly based on other data collected (e.g. insulin information entered manually or read automatically from a dosing device); and Triggered based on an event (e.g. a configurable amount of time after a glucose measurement is taken).

The meal information could also be used to drive reminders for the user (e.g. to warn the user that they may have missed a meal bolus). This logic could take a variety of forms:
  Warn if there is a large rise without a recorded bolus
  Warn if no meal/insulin is logged for a long amount of time Patterns such as rapid rises and falls can also be fed into the analysis. Rapid falls could be treated as an independent risk factor for hypoglycemia. Recommendations could be adjusted accordingly in their presence. Rapid rises can be treated as an accurate measure of intraday variability. The number or magnitude of rapid rises present can be compared to the overall variability to determine interday vs. intraday variability. Having separate measures for the different classes of variability would allow recommendations to be targeted more precisely to the root cause of the high variability experienced by the patient.

For example, if a high number of rapid rises or falls have been detected, treatment recommendations may be focused on the timing an size of boluses. In the opposite case, where it is found that there is much more interday variability than intraday variability, treatment recommendations may be focused on lifestyle changes such as meal timing and exercise.

Two Threshold Analog to Control Grid Used for Therapy Decision Support

The use of alternate metrics for a control grid used for diabetes therapy decision support is described. Also, a means to determine an "upper" threshold of a target glucose range that is equivalent to a median target defined by A1c is described.

In prior control grids, the upper range was set by doctor preference and custom, for instance 190 mg/dL. However, for patients with high median or high variability, this traditional upper limit may not be appropriate. A means to set this range based on target A1c (or glucose median), measured variability, and hypo risk tolerance is described.

The control grid, disclosed previously, is the key part of a method that can be used to generate diabetes therapy recommendations from glucose data. The control grid is a plot of a measure of central tendency (e.g, median) vs. a measure of variability (e.g., median minus the 10% ile). The glucose data are used to generate these measures. Zones can be defined on the control grid corresponding to treatment recommendations, such as "safe to increase dose" or "reduce variability before increasing dose". In this way, glucose data can be mapped to recommendations.

Zones can be defined by identifying boundaries, such as above or below the target median, and above or below a metric that defines high hypoglycemia risk. A novel aspect of this method is a boundary that identifies high and low variability zones. One particularly useful variability boundary identifies the maximum variability that can coexist with low hypoglycemia risk and while below the target median.

In clinical practice, identifying high and low variability in this way is useful because it allows notification to a clinician that when glucose variability is high, adjusting medication dose amounts alone may not be useful for improving glycemic control, but that steps must be taken to identify causes of high variability and to mitigate these.

The disclosure below describes alternative methods to achieve the glucose-to-recommendation mapping. For example, instead of using median and variability, the method could employ any two statistical measures that define a distribution of data. For instance, the statistical measures could be based on a glucose target range. A target range, commonly used in diabetes management and well understood by diabetes clinicians, is simply a glucose range defined between two thresholds—for instance, $G_{LOW}=70$ mg/dL and $G_{HIGH}=140$ mg/dL. For continuous sensor data, a common measure related to target range is "time-within-target" ($t_{WT}$), defined as the percentage of data within this range or the average number of hours in a day within this range. Similarly, the "time-above-target" ($t_{AT}$) and "time-below-target" ($t_{BT}$) are defined.

Figure 48:
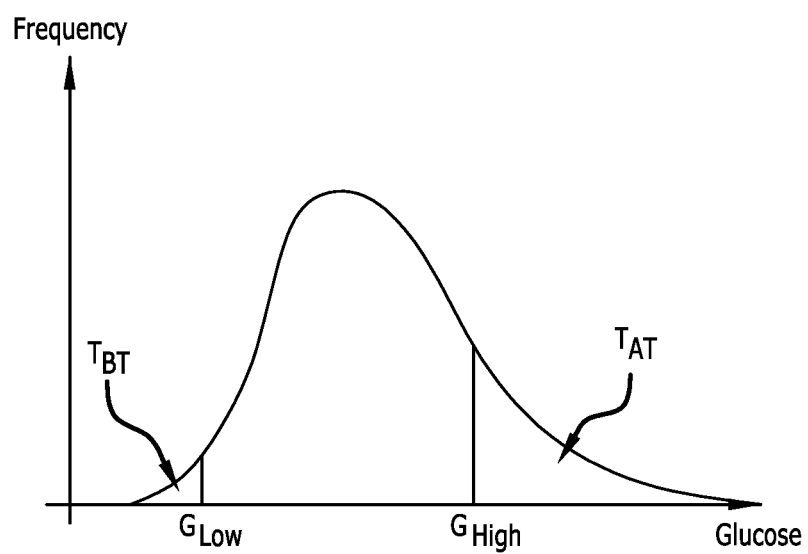
FIG. 48 is a plot of glucose data can be modeled as a distribution.

If we consider that glucose data can be modeled as a distribution (for instance, a gamma distribution), for predefined target thresholds $G_{LOW}$ and $G_{HIGH}$ we can calculate $t_{BT}$ and $t_{AT}$. An example of this is shown in FIG. 48.

We can also define, for these same thresholds, a metric $t_{BT\_HYPO}$ in which if exceeded by $t_{BT}$, then the patient may be determined to be at high hypoglycemia risk. For instance, we may define high hypoglycemia risk as whenever $t_{BT}$ is greater than 5% for $G_{LOW}=70$ mg/dL; in this example, $t_{BT\_HYPO}=5\%$. Likewise, a metric $t_{AT\_HYPER}$ can be defined in which if exceeded by $t_{AT}$, then the patient may be determined to be at high hyperglycemia risk. The degree of hypoglycemia risk can be adjusted by adjusting either the $G_{LOW}$ or $t_{BT\_HYPO}$. Likewise for hyperglycemia risk and $G_{HIGH}$ or $t_{AT\_HYPER}$.

Figure 49A:
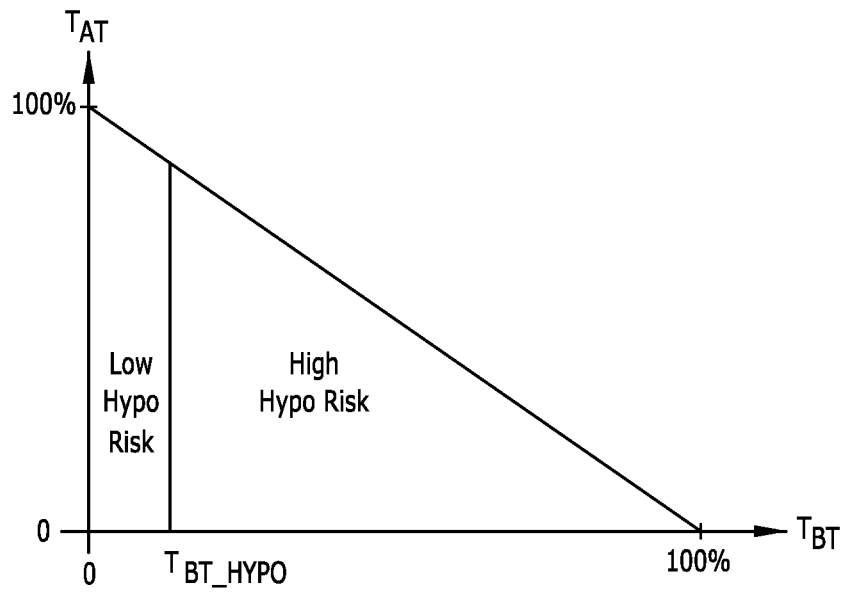
Figure 49B:
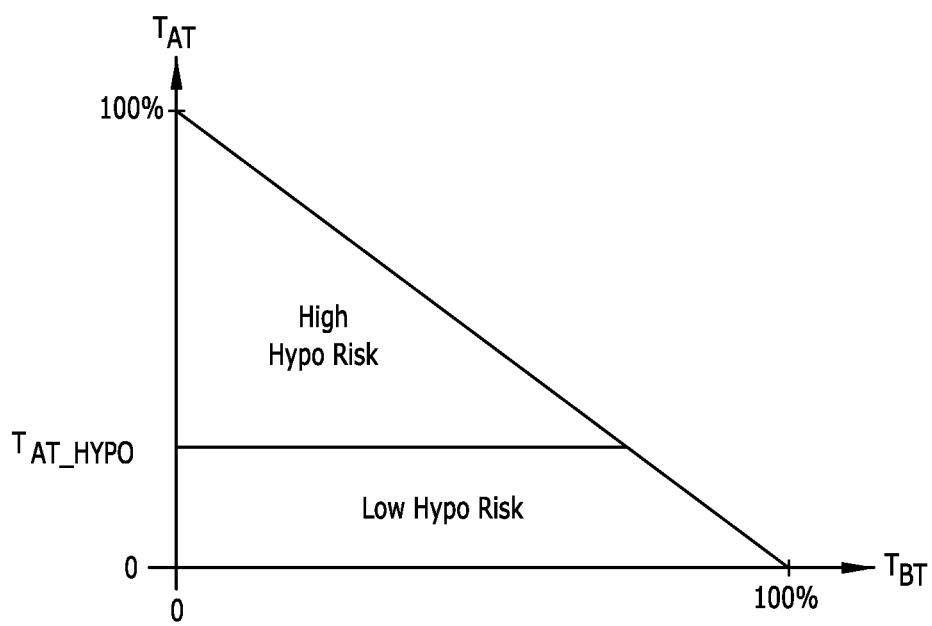
Figure 49C:
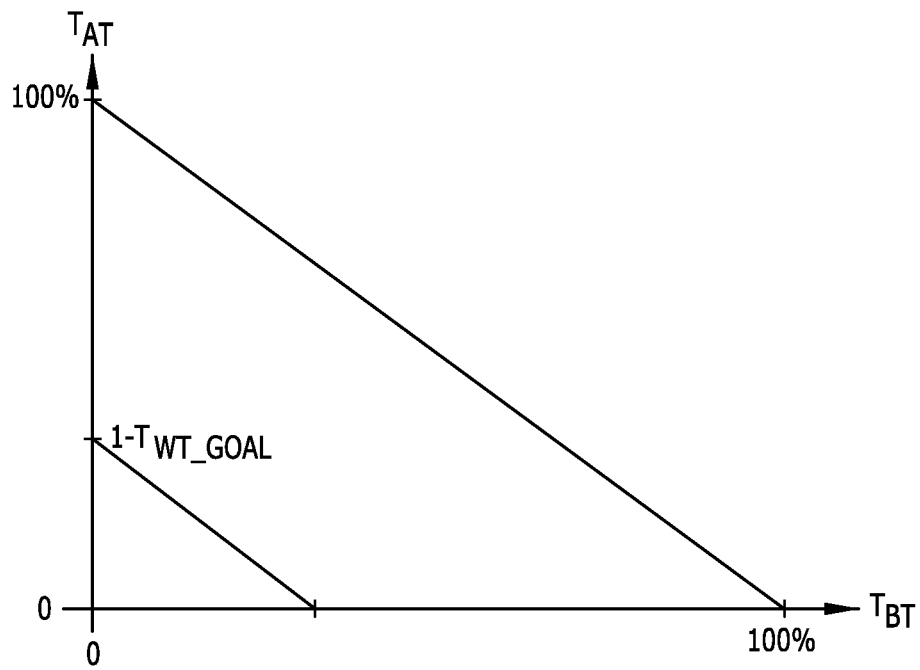
Figure 49D:
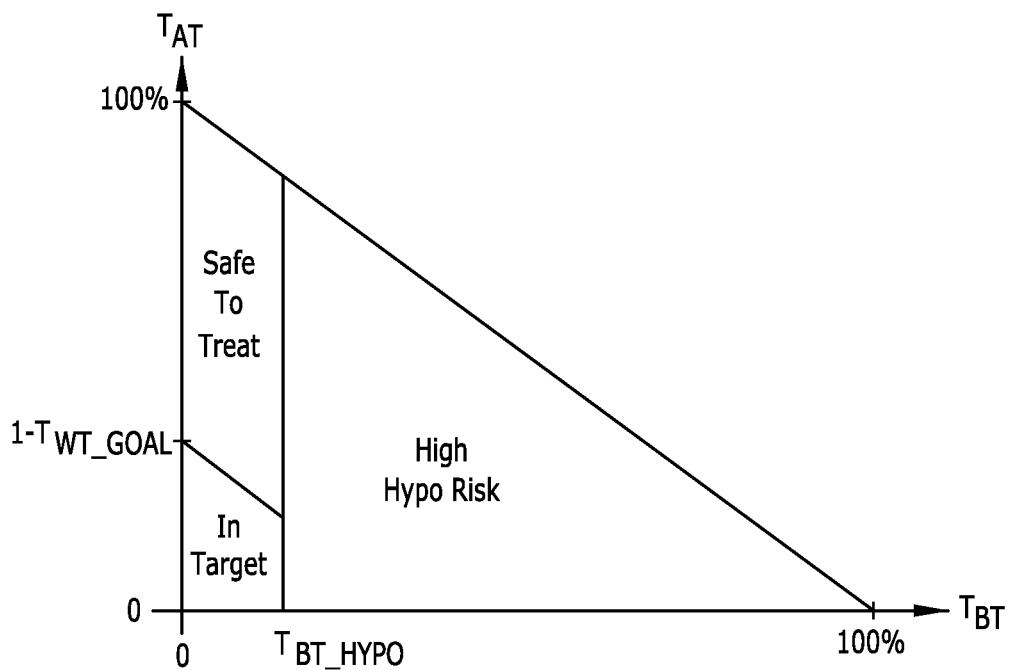

Any two of these three measures, $t_{BT}$, $t_{AT}$ and $t_{WT}$, can be used to define a control grid. FIGS. 49A-49F show a control grid defined by tAT and tBT. In FIG. 49A, a boundary is defined by $t_{BT\_HYPO}$, and two zones are created that identify hypoglycemia risk. FIG. 49B shows a different boundary defined by $t_{AT\_HYPER}$, which creates two zones that identify hyperglycemia risk. Alternatively, it may be more clinically appropriate to define a hyperglycemia risk boundary as a constant value of $t_{WT}$, which would translate to the $t_{AT}$ vs $t_{BT}$ grid as a line, illustrated in FIG. 49C. In FIG. 49D, we show an example of how these boundaries can be combined. In this case, the hypo risk boundary has precedence (since treating hypoglycemia is typically prioritized over treating hyperglycemia in practice). This results in three zones, as shown.

Figure 49E:
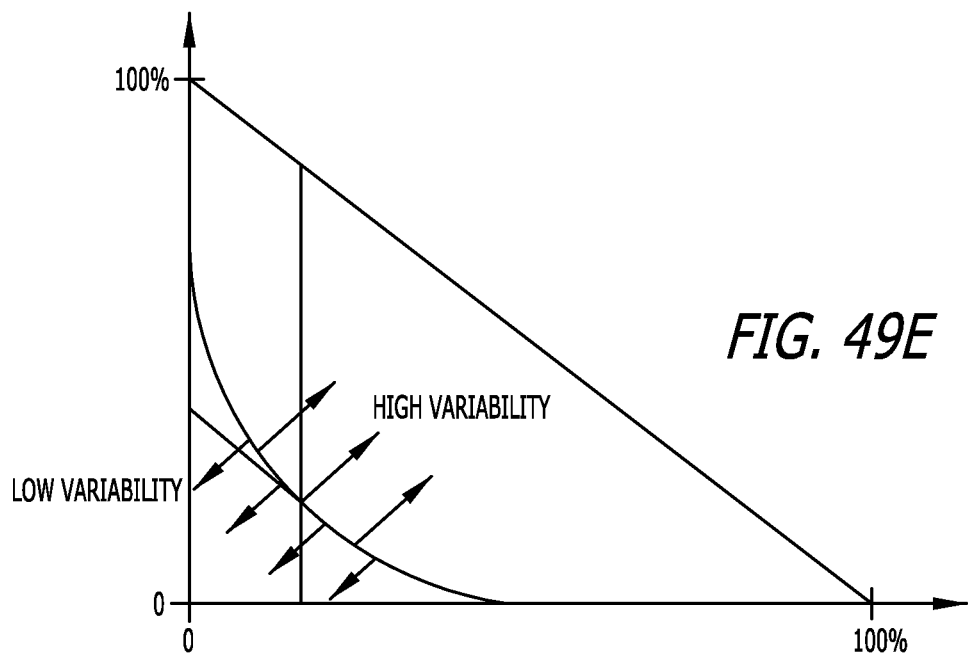
Figure 49F:
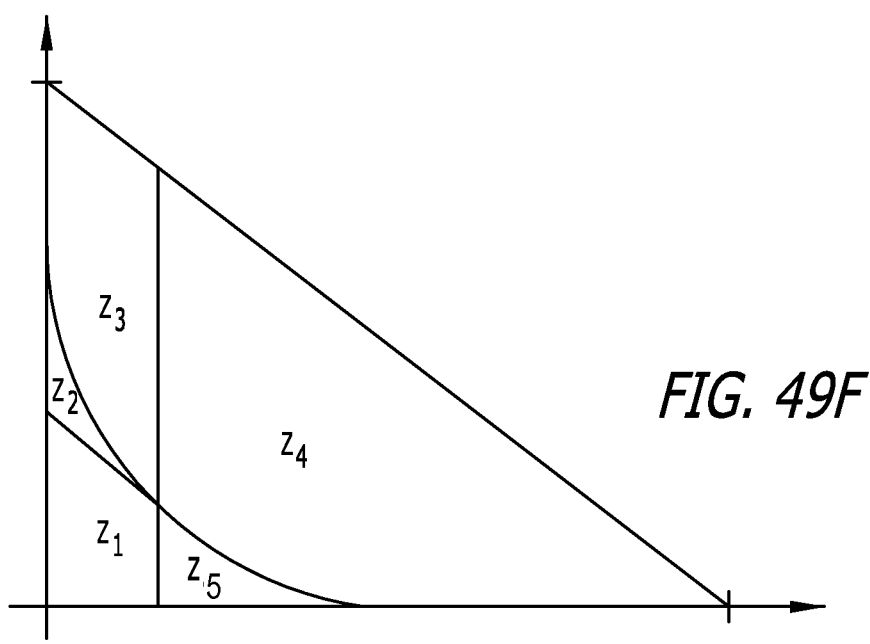

An important feature of the control grid, disclosed previously, is the identification of variability and its relationship to hypoglycemia risk. An appropriate boundary definition for high variability is where no further increase in variability can coexist with the target region. This constant variability boundary is illustrated in FIG. 49E, overlaying the other boundaries. In FIG. 49F, the boundaries are shown to identify five different zones; these zones can be mapped to assessments of the patient's glycemic control as shown in the table below, or to clinical recommendations, or to other classifications.

| | |
|---|---|
| Z1 = | In target |
| Z2 = | Safe-to-treat |
| Z3 = | Safe-to-treat, reduce variability |
| Z4 = | High hypoglycemia risk, reduce variability |
| Z5 = | High hypoglycemia risk, reduce medication |

Figure 50:
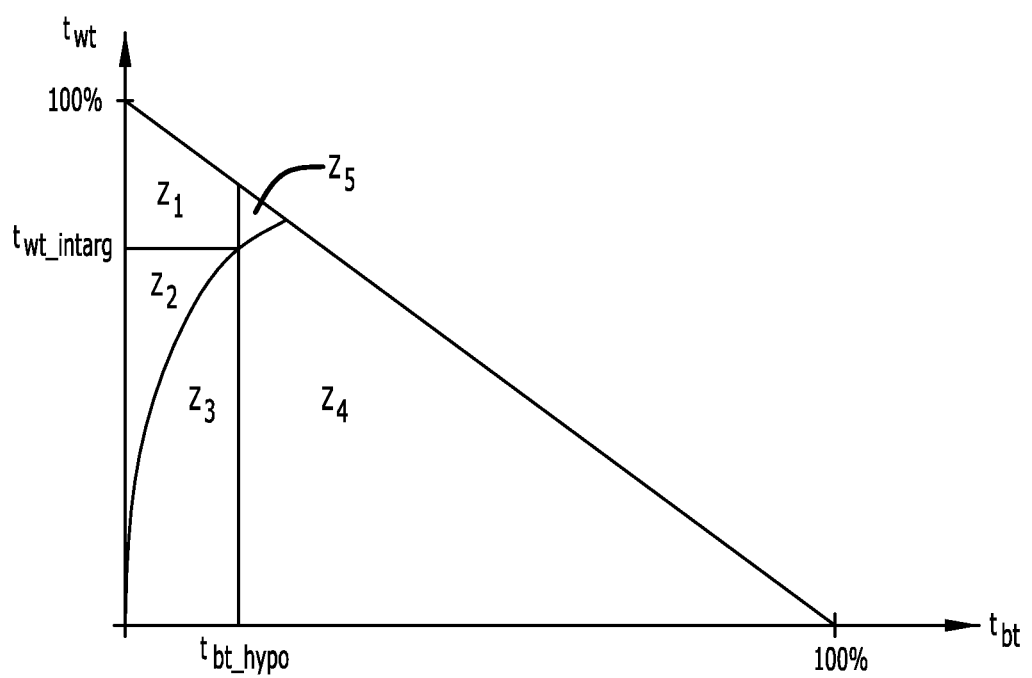
FIG. 50 is a grid with zones identified.

As mentioned, any statistical measure can be similarly used on the control grid. FIG. 50 shows a grid with zones identified with $t_{WT}$ on the y-axis and $t_{BT}$ on the x-axis.

Figure 51A:
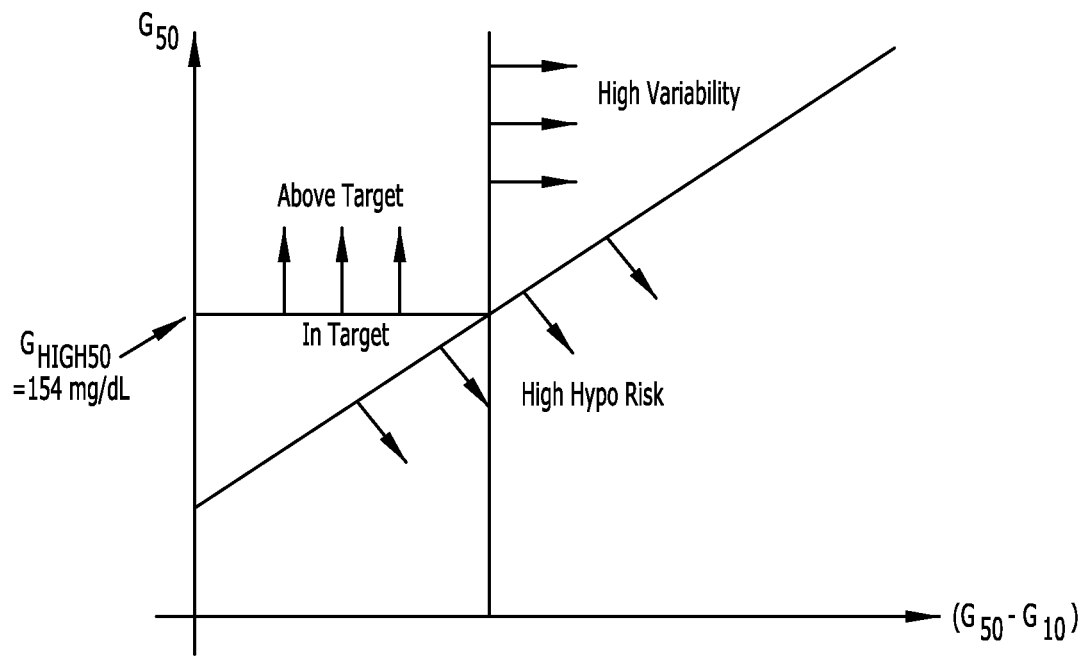
FIGS. 51A and 51B show the control grid.
Figure 51B:
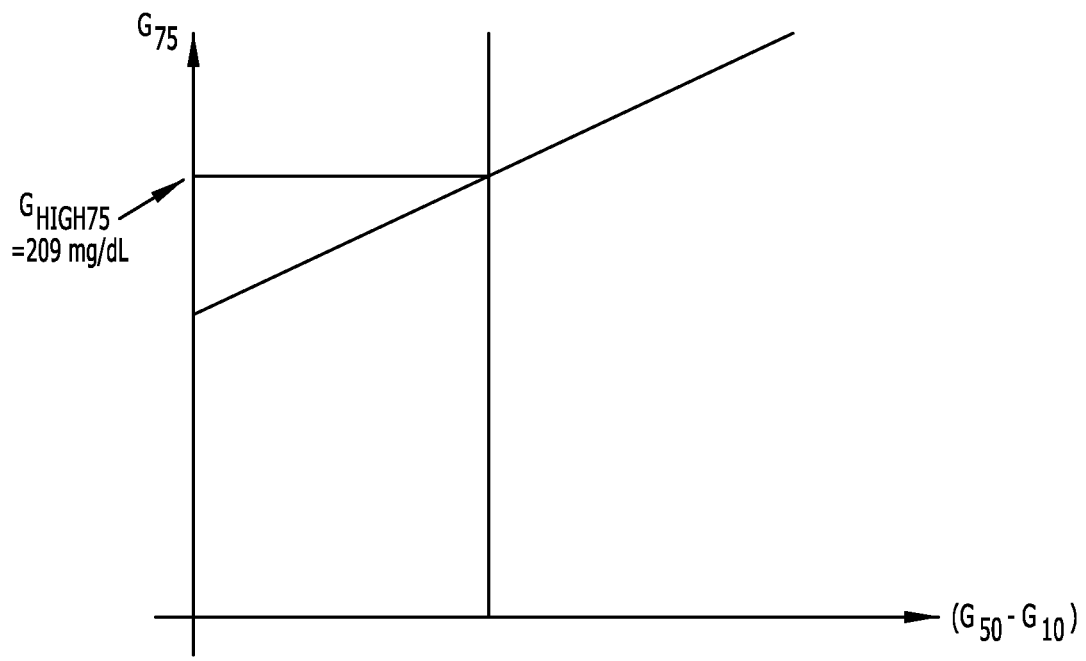

An alternate statistical measure that could be used, similar to those already discussed, is percentiles. For instance, the y-axis could be represented by the glucose 75%-ile ($G_{75}$) and the x-axis represented by the glucose 10%-ile ($G_{10}$). Now for predetermined hypo and hyper risk boundaries defined by $G_{LOW}$ and $t_{BT\_HYPO}$, and $G_{HIGH}$ and $t_{AT\_HYPER}$, we can determine equivalent target thresholds in terms of the $G_{10}$ and $G_{75}$ measures, $G_{LOW10}$ and $G_{HIGH75}$. This control grid is shown in FIGS. 51A-F1B.

As an example of the above embodiment, assume that hypo risk is defined by $G_{LOW}$=70 mg/dL and $t_{BT\_HYPO}$=7.2%, which means that a patient is at high risk for hypoglycemia if their glucose data are less than 70 mg/dL for more than 7.2% of the time. Also, assume that hyper risk is defined by $G_{HIGH}$=200 mg/dL and Tb=10%, which means that a patient is above target if their glucose data are greater than 200 mg/dL for more than 10% of the time. Using these values as parameters that define a gamma distribution model, we can calculate the target thresholds in terms of the measured percentiles, $G_{10}$ and $G_{75}$. $G_{LOW10}$=76 mg/dL and $G_{HIGH75}$=163 mg/dL. Patients and clinicians can now use these targets to control their glucose in an intuitive and robust way.

Note that any desired percentile may be used as a measure. Some choices will be more practical than others. For instance, it may not be practical to use $G_{10}$ and $G_{11}$, since it would require a tremendous amount of data to resolve the 1% difference. Also, $G_2$ and $G_{98}$ may not be good choices do to the large amount of data required to resolve the distribution tails. The original disclosure of the control grid chose $G_{50}$ and ($G_{50}$-$G_{10}$) as measures, since this roughly corresponds to choosing a central tendency measure and a variability measure, which is a common way to define distributions and requires less data to accurately estimate. $G_{75}$ and $G_{10}$, described above, may be good choices, as would be $G_{90}$ and $G_{10}$, as they lead to definition of a target range which is well understood by patients and clinicians as a tool for diabetes management. Also, these percentiles correspond to those used in the Ambulatory Glucose Profile standard used by many diabetes clinicians to assess patient glucose data. Finally, a good choice for percentiles may be $G_{75}$ and ($G_{50}$-$G_{10}$) or $G_{90}$ and ($G_{50}$-$G_{10}$), as these provide a high target range limit, and a variability measure that is well estimated by small amounts of data and is readily understood to be primarily an estimate of variability.

In previous control grid disclosures, it was described how the hypo risk boundary can be defined from glucose data from a population of patients. In this case the boundary was determined in terms of the $G_{50}$ and ($G_{50}$-$G_{10}$) measures. Using the same method, the boundary may be chosen for any percentile measures.

In general, this method could use any two statistical measures of data. Examples of other statistical measures are mean, mode, standard deviation, variance, MARD, LGBI, etc.

For the threshold that defines the high end of the target range, for instance $G_{HIGH75}$ or $G_{HIGH90}$, it can be useful to determine these thresholds based on the desired target A1c. In previous control grid disclosures, it was described how the target zone on the control grid had an upper bound defined as the target glucose median. This is the same as $G_{HIGH50}$. It has also been described how this target median can be associated with a target A1c. This is a useful parameter that can be adjusted by the clinician as it allows them to set an A1c target that may be more reasonable for the patient. For instance, the ultimate goal for all people with diabetes is to maintain an A1c value below 7%. However, if a patient currently as an A1c of 11%, it may be discouraging to use the 7% goal—it may be more realistic for the clinician to set an achievable goal of 9.5%. When the patient reaches this goal, the clinician can set a lower goal, and so forth. The target glucose median $G_{HIGH50}$ can be determined from the target A1c selected, as described elsewhere.

Figure 52A:
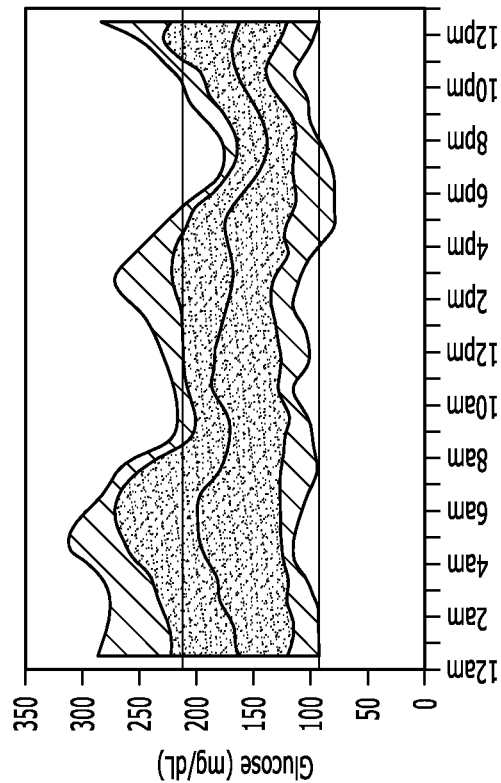
FIGS. 52A and 52B show gamma distributions of glucose over time.
Figure 52B:
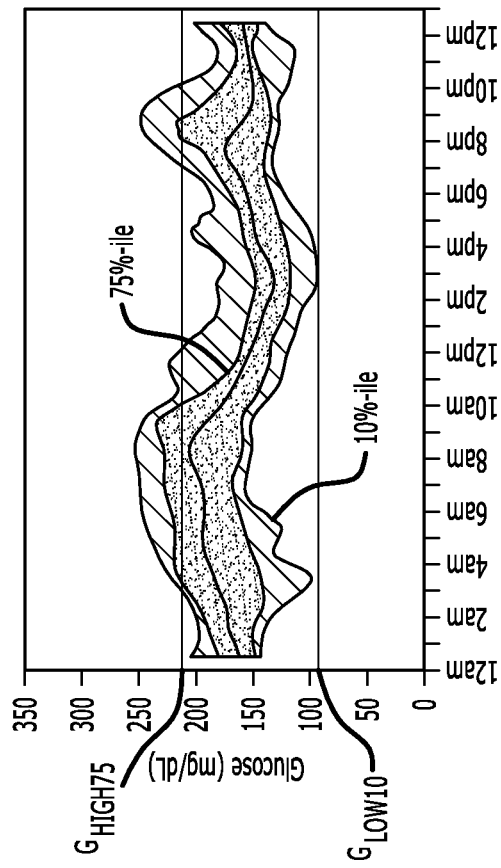

If a percentile measure different from the median is used, however, the equivalent target threshold must be determined in terms of this different measure. Unfortunately, unlike the median target which can be defined as described above for data with any possible value of statistical variability, other measures for the target, such as the 75%-ile and the 10%-ile, will depend on data variability. That is, using the measure $G_{75}$ for example, for a given median target, a corresponding $G_{HIGH75}$ could be calculated given an assumed distribution with a median at $G_{HIGH50}$ and a defined variation metric. This variation metric could be defined to be any value, but a logical choice is for it to correspond to a distribution that exactly meets the hypo risk criteria. Therefore, $G_{HIGH75}$ can be determined from a gamma distribution defined by a median at $G_{HIGH50}$, and with variation defined by $G_{LOW}$ and $t_{BT\_HYPO}$. As an example, given $G_{LOW}$=70 mg/dL and $t_{BT\_HYPO}$=7.2%, and $G_{HIGH50}$=154 mg/dL, the gamma distribution with these parameters would result in a value at the 75% percentile of $G_{HIGH75}$=209 mg/dL. This example is illustrated in FIGS. 52A and 52B where the G50 vs (G50–G10) control grid is shown with an equivalent G75 vs (G50–G10) control grid.

The key benefit of determining an equivalent target at the 75% or the 90% percentiles is that it is more natural for patients to manage their glucose based on keeping their glucose below a high target, rather than trying to achieve a median or mean glucose target. For example, a goal could be to keep their glucose below a value of 175 mg/dL 90% of the time. This target glucose value, $G_{HIGH90}$, that is determined by a clinician who defines their target A1c and their hypo risk level, can be provided to the clinician, caregiver and/or patient. One use would be to display a line on the AGP at this threshold value. Another use would be to load this value into a glucose meter which would be programmed to display the value as a line on glucose history plots, or to use the value in a calculation of $t_{AT}$.

Alternatives to the methodologies described above can be contemplated by changing the role of "inputs" and "outputs". For instance, rather than determine a high range threshold by setting the A1c goal and hypo risk threshold, a system could allow the clinician to set the desire high range threshold and hypo risk threshold, and determine the median target or equivalent A1c value. Another example is a system that would allow the clinical to set the A1c goal, hypo risk threshold and desired high range threshold percentile measure, and determine the associated high range threshold. Many other possibilities along this line are obvious. Other possible systems include one where a routine is applied to the data to determine the best fit to one of a number of possible distribution models, and this selected distribution is used in the method described.

When using sensor data, it is likely that enough data are collected to provide a good estimate of a distribution. For SMBG data, where fewer data points are usually available, it may be useful to fit the data to a distribution model, such as a gamma distribution, to calculate $t_{BT}$ and $t_{AT}$.

Note that distributions other than a gamma distribution may be used; however, for most common distributions, two parameters must be defined in order to uniquely define the distribution. This is the case for the examples above. The method described here could be generalized to distributions that require three or more parameters to uniquely define; in these cases, 3 or more measures need to be used, with corresponding metrics defined.

Figure 53A:
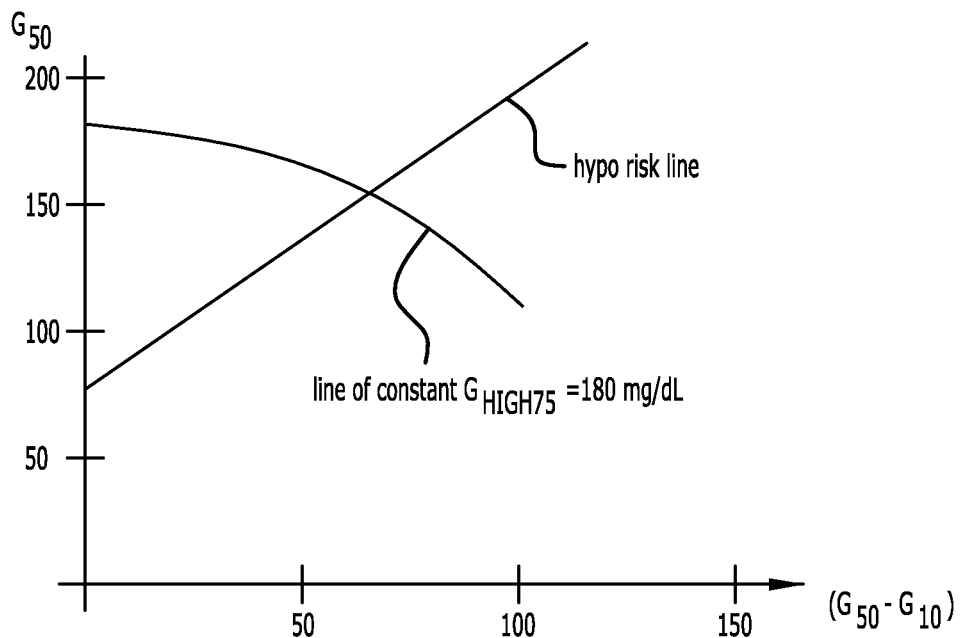
FIGS. 53A and 53B show two or more boundaries associated with a measure.
Figure 53B:
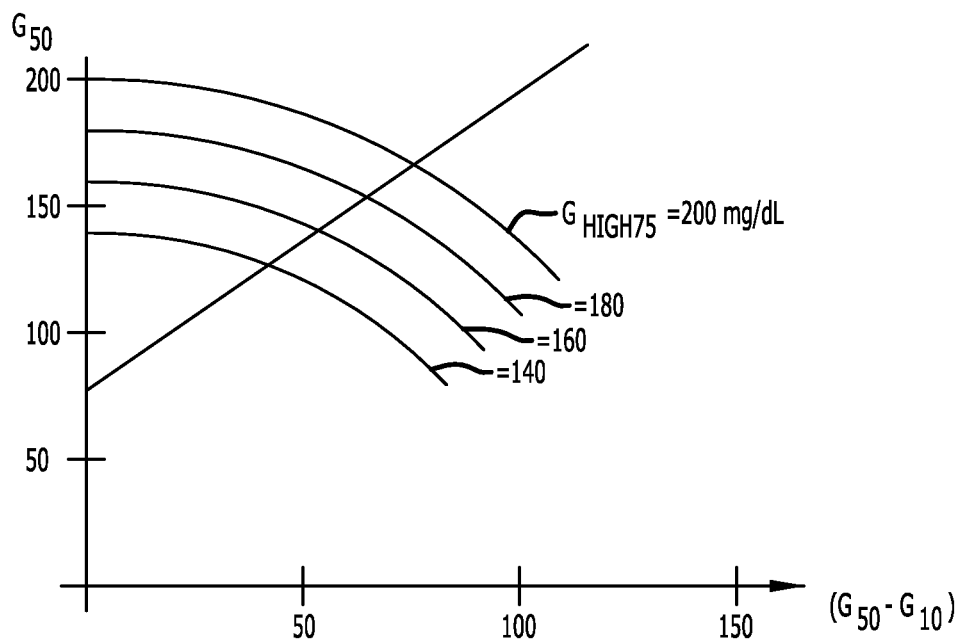

Another embodiment of the method described would incorporate two or more boundaries associated with a mea sure; for example, instead of this "above" and "below" (or "high" or "low"), we may have two boundaries that "high", "moderate" or "low." See FIGS. 53A and 53B. Previous disclosures describe these boundaries defined by gradations in the uncertainty associated with a measure; however, multiple boundaries may be associated with any measure for any reason.

high. If above the hyper risk threshold but below the hypo risk threshold, or if below the hyper risk threshold but above the hypo risk threshold, the variability may not be discernible using this method; however, in this case the recommendations may be limited to medication adjustment only, or may always include guidance to reduce variability as a conservative approach.

TABLE 5

Example rule-based control zone assignment algorithm

| | | | | |
|---|---|---|---|---|
| Hyperglycemia control (example criteria) | Within Target (<20% above high threshold) | Within Target (<20% above high threshold) | Above Target (>=20% above high threshold) | Above Target (>=20% above high threshold) |
| Hypoglycemia Risk (example criteria) | Low Risk (<10% below low threshold) | High Risk (>=10% below low threshold) | Low Risk (<10% below low threshold) | High Risk (>=10% below low threshold) |
| Glucose Variability (inferred) | Low Variability | Low Variability | Low Variability | High Variability |
| Control Zone | 1 | 10 | 3 | 12 |

Rule-Based Mapping to Medication Adjustment Guidance

A means of providing diabetes treatment recommendations using rule-based logic applied to a sample of glucose measurements is disclosed. Prior methods for recommendation logic have not typically incorporated glucose variability. The current invention leverages the observed and clinically-relevant relationship between median glucose, low-range glucose variability and hypoglycemia risk to derive treatment recommendations. This potential advantage is to make the recommendations more applicable and useful to patients and HCPs.

Figure 54:
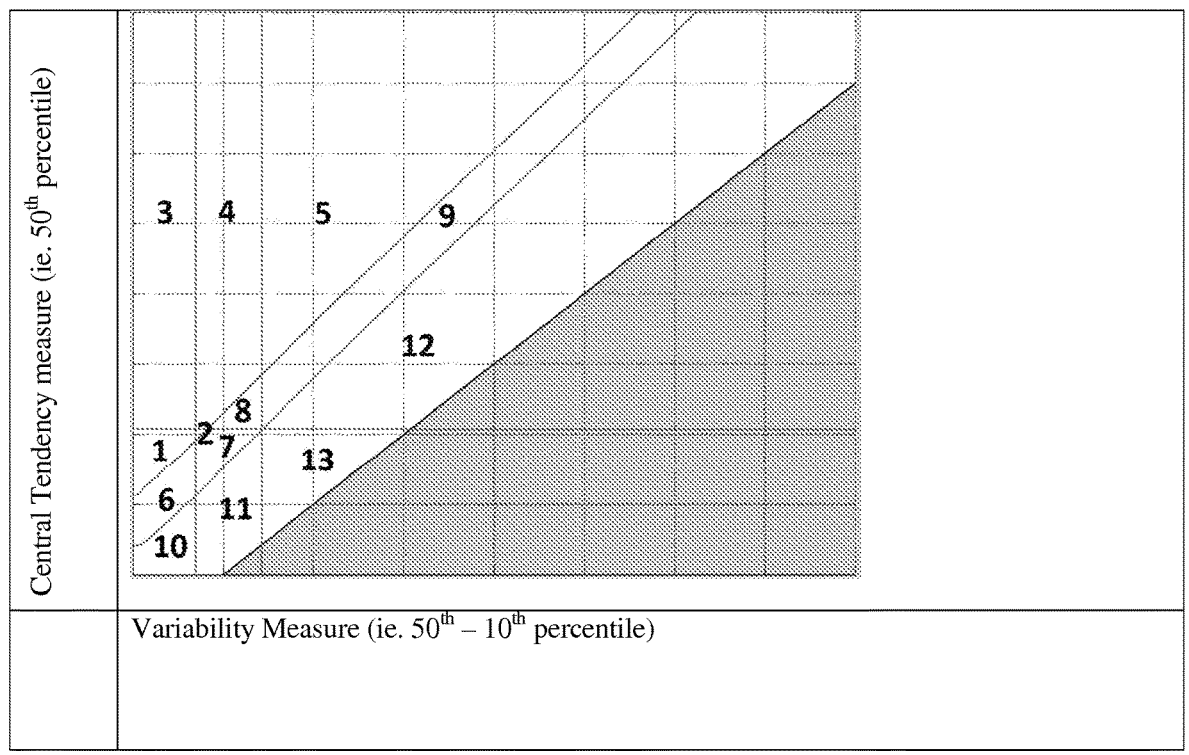
FIG. 54 is a graph of guidance zones.

The current embodiment provides a means of guiding diabetes treatment intervention by rule-based decisions applied to a sample of glucose measurements. As background, prior methods are based on determining a central-tendency value (i.e. 50th percentile) and a low-range variability value (i.e. 50th-10th percentile) to characterize the hyperglycemia control, variability control, and future risk of hypoglycemia. Given thresholds to determine categories of control (ie. "Above", "Within", "Below", or "High", "Moderate", "Low") for each of these, a number of zones can be associated with outputs to provide diabetes treatment guidance. An example of these zones are shown in FIG. 54. This defines the main example of a "zone assignment" algorithm.

Figure 55A:
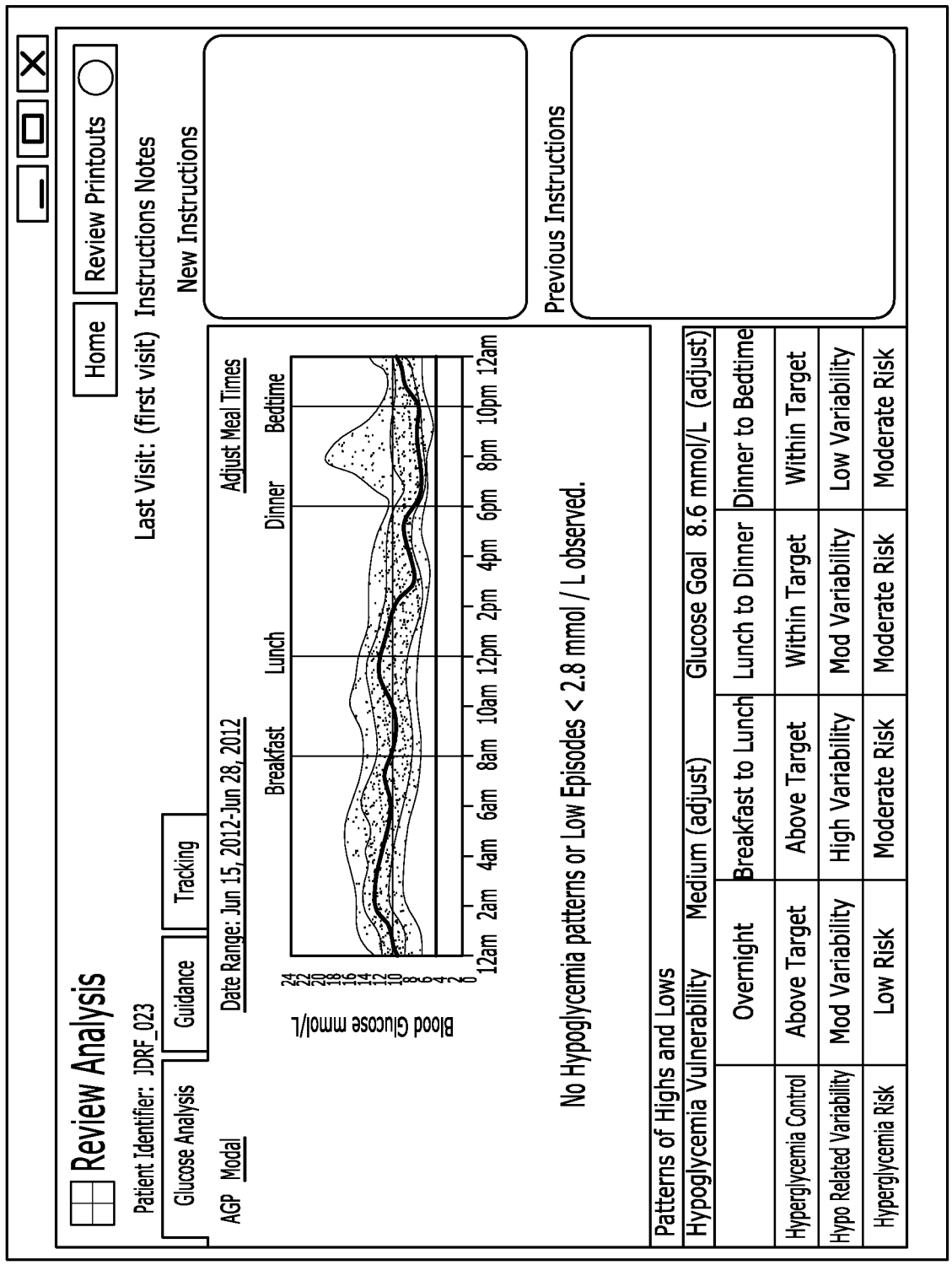

The current invention would use a number of rule-based decisions to arrive at "control zones", which could follow the same or similar mapping to guidance output, such as that shown in FIGS. 55A and 55B. These rules could bypass estimating glucose variability directly, but rather infer the glucose variability based on the outcomes of the rule checks. For example, in a simple case of checking above and below a single target glucose range for a single time period of interest (say "overnight"), the zone-assignment algorithm could be to check if the rate of above-target-range glucose values exceed a threshold or not (therefore "hyperglycemia control" would be "Above" or "Within") and then check if the rate of below-target-range glucose values exceed a threshold or not (therefore "hypoglycemia risk" would be "Low or "High"). The glucose variability could be inferred (as listed in Table 5) and the guidance output determined by the control zone as listed in Table 6.

For instance, if below both the hypo and hyper risk thresholds, then the variability would be determined to be low. Alternatively, if above both the hypo and hyper risk thresholds, then the variability would be determined to be Another method would be to explicitly estimate variability and compare to a threshold (or multiple thresholds) to determine if the result is "high" variability or "low" variability. Then the hypo and hyper risk measures are determined and applied to a risk metric table; one table is used when "high" variability is detected and another table is used if "low" variability is detected. Note that tables may be used or functions or any other equivalent means to process these results.

Another method would be to generate new thresholds to determine "high" or "low" variability, if above the hyper risk threshold but below the hypo risk threshold, or if below the hyper risk threshold but above the hypo risk threshold. One embodiment would be, it above the hyper risk threshold but below the hypo risk threshold, to determine a new high threshold as the 80%-ile of the data (or using the percentile corresponding to the hyper risk threshold), and determine a new low threshold as the new high threshold minus the difference between the hyper risk threshold and the hypo risk threshold. If the 10%-ile of the data is below this new low threshold, then the variability will be determined to be "high"; otherwise, the variability will be determined to be "low". Likewise, if below the hyper risk threshold but above the hypo risk threshold, then determine a new low threshold as the 10%-ile of the data, and determine a new high threshold as the new low threshold plus the difference between the hyper risk threshold and the hypo risk threshold. The result of this method is essentially the same as explicitly determining a variability measure of the data, but does not require this variability measure to be explicitly determined.

Other methods are related to the above in that they do not require explicit determination of variability. For instance, a high and low threshold pair can be created by adding or subtracting an identical offset to the hypo and hyper risk thresholds. Multiple threshold pairs can be created in this way, using a range of offsets. Then the 10%-ile and 80%-ile can be compared to all of these pairs and if for at least one pair, if above both the hypo and hyper risk thresholds, then the variability would be determined to be "high"; otherwise, the variability will be determined to be "low". This methodology can be extended to many different percentiles and scaling schemes. For instance, instead of determining the new high and low thresholds based on offsetting the hyper and hypo risk thresholds, other functions of the hyper and hypo risk thresholds could be contemplated. For example, a linear function may be used where a slope parameter that multiplies the hyper risk threshold is greater than one, in order reduce the likelihood that "high" variability would be determined when the glucose levels are tending higher.

Multiple levels of rule checks could be designed for hyperglycemia control and hypoglycemia risk. For example hypoglycemia risk could be stratified into three levels as:

Low Risk: <5% below low threshold
Moderate Risk: 5% to <10% below low threshold
High Risk: >=10% below low threshold This method may be enhanced by more specifically identifying medications to be added, increased or decreased. A table of medications could be used where each medication (or medication class) is represented by a row and attributes of the medication are represented in one or more columns. Attributes may include a relative effectiveness score by time period, so that if specific time of day periods (typically defined by meal times) are assessed for a patient and it is indicated that increased medication is recommended for that period, then the table could be scanned to look for the medication with the highest relative effectiveness for that period. Other attributes in the table could include contraindications, cost, side-effects, inconvenience, etc, and compared with relevant patient needs or exclusions.

Figure 56:
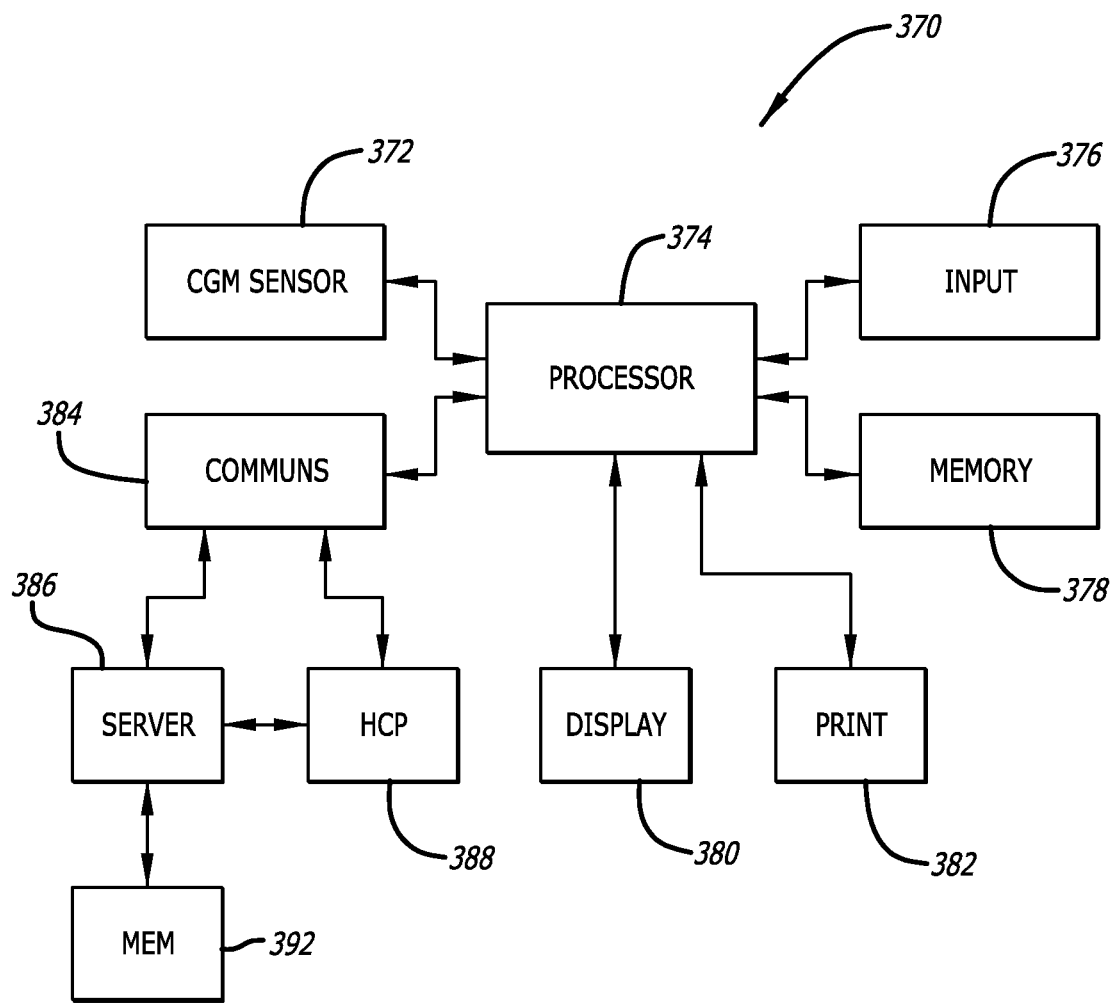
FIG. 56 is a block diagram of a system usable to embody inventive concepts disclosed and claimed herein, including a processor, a continuous glucose monitor, a memory, display, printer, and remote connections to servers.

Referring now to FIG. 56, a block diagram is presented showing an embodiment of a system 370 usable to accomplish the above. In particular, a CGM sensor 372 communicates sensed glucose signals to a processor 374. The processor is connected with an input device 376, such as a keyboard or pointing device or both, and may include additional or different input devices. A memory 378 stores data and programs to which the processor has access. Outputs from the execution of programs may be displayed 380 and/or printed 382. For example, Insights reports 69, control grids 145 and other data analyses or data presentations may be displayed and printed. The processor also has a communications capability 384 and may communicate over various means with other processors, servers 386, as required. In regard to an HCP 388, the processor 374 may communicate directly 390 or the HCP may obtain the processor output through a server 386 in a more indirect manner. Programs, such as those disclosed above, may reside on the memory 378 or may be obtained by the processor 374 from a remote source, such as from a memory 392 at the remote server 386. Other arrangements for data flow, application flow, and communications are possible. Multiple servers, local and remote, may participate as well as multiple memories. Although the memory 378 the process or shown as a single box, it may in fact be multiple memory devices. The same applies to other components of FIG. 56. Additionally, FIG. 56 components may be disposed on many different kinds of computing devices, such as a desktop computer, laptop computer, tablets, smart phones, and other. FIG. 56 provides only a single embodiment.

The methodologies describe above could be combined so that the system not only recommends specific medications, but also indicates when medication adjustment may not be useful or wise, but steps to identify and mitigate patient variability should be taken first.

Unless the context requires otherwise, throughout the specification and claims that follow, the word "comprise" and variations thereof, such as, "comprises" and "comprising" are to be construed in an open, inclusive sense, which is as "including, but not limited to."

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

TABLE 6

Association of Control Zone ("Zone") and Medication Guidance Output

| | Median | Variability | Hyporisk | Zone | Title Text | Dose Adj Text 1 | Dose Adj More Text 1 | Dose Adj Text 2 | Dose Adj More Text 2 |
|---|---|---|---|---|---|---|---|---|---|
| Overnight | Within Target | Low Variability | Low Hypo Risk | 1 | Overnight glucose is in target. | | | | |
| | Within Target | Mod Variability | Low Hypo Risk | 2 | Overnight glucose is in target. However, glucose variability is high. Consider the following action: | Reduce variability. | Reducing glucose variability will help to ensure that glucose levels can be sustained in the target range. | | |
| | Above Target | Low Variability | Low Hypo Risk | 3 | Glucose levels are high overnight. Consider the following action: | Increase LA dose - note that this may also lower glucose after meals. | Increasing the LA dose should reduce high glucose levels overnight. Note that this may also lower glucose levels after meals, so a decrease in the RA dose may be warranted for meals where glucose levels are within target. | | |
| | Above Target | Mod Variability | Low Hypo Risk | 4 | Glucose levels are high overnight. Also, glucose variability is high. Consider the following action: | Increase LA dose while reducing variability. Note that this may also lower glucose after meals. | Increasing the LA dose should reduce high glucose levels overnight. Note that this may also lower glucose levels after meals, so a decrease in the RA dose may be warranted for meals where glucose levels are within target. Also, reducing glucose variability will allow further increases in LA dose while keeping hypoglycemia risk low. | | |
| | Above Target | High Variability | Low Hypo Risk | 5 | <same as above> | <same as above> | <same as above> | | |
| | Within Target | Low Variability | High Hypo Risk | 10 | Glucose levels are low overnight, contributing to hypoglycemia risk. | Decrease LA dose. | Decreasing the LA dose should reduce hypoglycemia risk overnight. Note that | | |

TABLE 6-continued

Association of Control Zone ("Zone") and Medication Guidance Output

| | Median | Variability | Hyporisk | Zone | Title Text | Dose Adj Text 1 | Dose Adj More Text 1 | Dose Adj Text 2 | Dose Adj More Text 2 |
|---|---|---|---|---|---|---|---|---|---|
| | Within Target | Low Variability | Mod Hypo Risk | 6 | Consider the following action: | | this may also raise glucose levels after meals. | | |
| | Within Target | High Variability | High Hypo Risk | 13 | <same as above> | Reduce variability. | First priority should be to take steps to reduce glucose variability overnight. If it is unlikely that variability can be reduced substantially, consider the next option. | Or decrease LA dose, if variability cannot be reduced. | If it is not likely that variability overnight can be reduced, consider decreasing LA dose to reduce hypoglycemia risk. Note that this may also raise glucose levels after meals. |
| | Within Target | Mod Variability | High Hypo Risk | 11 | <same as above> | <same as above> | <same as above> | <same as above> | <same as above> |
| | Within Target | Mod Variability | Mod Hypo Risk | 7 | <same as above> | <same as above> | <same as above> | <same as above> | <same as above> |
| | Above Target | High Variability | High Hypo Risk | 12 | Glucose levels are high overnight. However, high glucose variability is contributing to hypoglycemia risk. Consider the following actions: | Reduce variability, no LA dose adjustment | First priority should be to take steps to reduce glucose variability overnight. If it is unlikely that variability can be reduced substantially, consider the next option. | Or decrease LA dose, if variability cannot be reduced. | If it is not likely that variability overnight can be reduced, consider decreasing LA dose to reduce hypoglycemia risk. Note that this may also raise glucose levels after meals. |
| | Above Target | High Variability | Mod Hypo Risk | 9 | <same as above> | <same as above> | <same as above> | <same as above> | <same as above> |
| | Above Target | Mod Variability | Mod Hypo Risk | 8 | <same as above> | <same as above> | <same as above> | <same as above> | <same as above> |
| Post-Dinner | Within Target | Low Variability | Low Hypo Risk | 1 | Post-dinner glucose is in target. | | | | |
| | Within Target | Mod Variability | Low Hypo Risk | 2 | Post-dinner glucose is in target. However, glucose variability is high. Consider the following action: | Reduce variability. | Reducing glucose variability will help to ensure that glucose levels can be sustained in the target range. | | |
| | Above Target | Low Variability | Low Hypo Risk | 3 | Glucose levels are high after dinner. Consider the following action: | Increase RA dinner dose - note that this may also lower overnight glucose. | Increasing the RA dose at dinner should reduce glucose levels after dinner. Note that this may also lower overnight glucose levels, so a decrease in the LA dose may be | | |

TABLE 6-continued

Association of Control Zone ("Zone") and Medication Guidance Output

| Median | Variability | Hyporisk | Zone | Title Text | Dose Adj Text 1 | Dose Adj More Text 1 | Dose Adj Text 2 | Dose Adj More Text 2 |
|---|---|---|---|---|---|---|---|---|
| Above Target | Mod Variability | Low Hypo Risk | 4 | Glucose levels are high after dinner. Also, glucose variability is high. Consider the following action: | Increase RA dinner dose while reducing variability. Note that this may also lower overnight glucose. | warranted if overnight glucose levels are within target. Increasing the RA dinner dose should reduce glucose levels after dinner. Note that this may also lower overnight glucose levels, so a decrease in the LA dose may be warranted if overnight glucose levels are within target. Also, reducing glucose variability will allow further increases in RA dinner dose while keeping hypoglycemia risk low. | | |
| Above Target | High Variability | Low Hypo Risk | 5 | <same as above> | <same as above> | <same as above> | | |
| Within Target | Low Variability | High Hypo Risk | 10 | Glucose levels are low after dinner, contributing to hypoglycemia risk. Consider the following action: | Decrease RA dinner dose. | Decreasing the RA dose at dinner should reduce hypoglycemia risk after dinner. Note that this may also raise overnight glucose levels. | | |
| Within Target | Low Variability | Mod Hypo Risk | 6 | <same as above> | <same as above> | <same as above> | | |
| Within Target | High Variability | High Hypo Risk | 13 | Glucose levels are low after dinner. High glucose variability is also contributing to hypoglycemia risk. Consider the following actions: | Reduce variability. | First priority should be to take steps to reduce glucose variability after dinner. If it is unlikely that variability can be reduced substantially, consider the next option. | Or decrease RA dinner dose, if variability cannot be reduced. | If it is not likely that variability after dinner can be reduced, consider decreasing RA dinner dose to reduce hypoglycemia risk. Note that this may also raise overnight glucose levels. |
| Within Target | Mod Variability | High Hypo Risk | 11 | <same as above> | <same as above> | <same as above> | <same as above> | <same as above> |
| Within Target | Mod Variability | Mod Hypo Risk | 7 | <same as above> | <same as above> | <same as above> | <same as above> | <same as above> |
| Above Target | High | High | 12 | Glucose levels are | Reduce variability, no | First priority should be | Or decrease RA | If it is not likely that |

TABLE 6-continued

Association of Control Zone ("Zone") and Medication Guidance Output

| | Median | Variability | Hyporisk | Zone | Title Text | Dose Adj Text 1 | Dose Adj More Text 1 | Dose Adj Text 2 | Dose Adj More Text 2 |
|---|---|---|---|---|---|---|---|---|---|
| | Target | Variability | Hypo Risk | | high after dinner. However, high glucose variability is contributing to hypoglycemia risk. Consider the following actions: | RA dinner dose adjustment | to take steps to reduce glucose variability after dinner. If it is unlikely that variability can be reduced substantially, consider the next option. | dinner dose, if variability cannot be reduced. | variability after dinner can be reduced, consider decreasing RA dinner dose to reduce hypoglycemia risk. Note that this may also raise overnight glucose levels. |
| | Above Target | High Variability | Mod Hypo Risk | 9 | <same as above> | <same as above> | <same as above> | <same as above> | <same as above> |
| | Above Target | Mod Variability | Mod Hypo Risk | 8 | <same as above> | <same as above> | <same as above> | <same as above> | <same as above> |
| Post-Breakfast | Within Target | Low Variability | Low Hypo Risk | 1 | Post-breakfast glucose is in target. | | | | |
| | Within Target | Mod Variability | Low Hypo Risk | 2 | Post-breakfast glucose is in target. However, glucose variability is high. Consider the following action: | Reduce variability. | Reducing glucose variability will help to ensure that glucose levels can be sustained in the target range. | | |
| | Above Target | Low Variability | Low Hypo Risk | 3 | Glucose levels are high after breakfast. Consider the following action: | Increase RA breakfast dose. | Increasing the RA dose at breakfast should reduce glucose levels after breakfast. | | |
| | Above Target | Mod Variability | Low Hypo Risk | 4 | Glucose levels are high after breakfast. Also, glucose variability is high. Consider the following action: | Increase RA breakfast dose while reducing variability. | Increasing the RA breakfast dose should reduce glucose levels after breakfast. Also, reducing glucose variability will allow further increases in RA breakfast dose while keeping hypoglycemia risk low. | | |
| | Above Target | High Variability | Low Hypo Risk | 5 | <same as above> | <same as above> | <same as above> | | |
| | Within Target | Low Variability | High Hypo Risk | 10 | Glucose levels are low after breakfast, contributing to hypoglycemia risk. Consider the following action: | Decrease RA breakfast dose. | Decreasing the RA dose at breakfast should reduce hypoglycemia risk after breakfast. | | |
| | Within Target | Low Variability | Mod Hypo Risk | 6 | <same as above> | <same as above> | <same as above> | | |
| | Within Target | High | High | 13 | Glucose levels are | Reduce variability. | First priority should be | Or decrease RA | If it is not likely that |

TABLE 6-continued

Association of Control Zone ("Zone") and Medication Guidance Output

| | Median | Variability | Hyporisk | Zone | Title Text | Dose Adj Text 1 | Dose Adj More Text 1 | Dose Adj Text 2 | Dose Adj More Text 2 |
|---|---|---|---|---|---|---|---|---|---|
| | Target | Variability | Hypo Risk | | low after breakfast. High glucose variability is also contributing to hypoglycemia risk. Consider the following actions: | | to take steps to reduce glucose variability after breakfast. If it is unlikely that variability can be reduced substantially, consider the next option. | breakfast dose, if variability cannot be reduced. | variability after breakfast can be reduced, consider decreasing RA breakfast dose to reduce hypoglycemia risk. |
| | Within Target | Mod Variability | High Hypo Risk | 11 | <same as above> | <same as above> | <same as above> | <same as above> | <same as above> |
| | Within Target | Mod Variability | Mod Hypo Risk | 7 | <same as above> | <same as above> | <same as above> | <same as above> | <same as above> |
| | Above Target | High Variability | High Hypo Risk | 12 | Glucose levels are high after breakfast. However, high BG variability is contributing to hypoglycemia risk. Consider the following actions: | Reduce variability, no RA breakfast dose adjustment | First priority should be to take steps to reduce glucose variability after breakfast. If it is unlikely that variability can be reduced substantially, consider the next option. | Or decrease RA breakfast dose, if variability cannot be reduced. | If it is not likely that variability after breakfast can be reduced, consider decreasing RA breakfast dose to reduce hypoglycemia risk. |
| | Above Target | High Variability | Mod Hypo Risk | 9 | <same as above> | <same as above> | <same as above> | <same as above> | <same as above> |
| | Above Target | Mod Variability | Mod Hypo Risk | 8 | <same as above> | <same as above> | <same as above> | <same as above> | <same as above> |
| Post-Lunch | Within Target | Low Variability | Low Hypo Risk | 1 | Post-lunch glucose is in target. | | | | |
| | Within Target | Mod Variability | Low Hypo Risk | 2 | Post-lunch glucose is in target. However, glucose variability is high. Consider the following action: | Reduce variability. | Reducing glucose variability will help to ensure that glucose levels can be sustained in the target range. | | |
| | Above Target | Low Variability | Low Hypo Risk | 3 | Glucose levels are high after lunch. Consider the following action: | Increase RA lunch dose. | Increasing the RA dose at lunch should reduce glucose levels after lunch. | | |
| | Above Target | Mod Variability | Low Hypo Risk | 4 | Glucose levels are high after lunch. Also, glucose variability is high. Consider the following action: | Increase RA lunch dose while reducing variability. | Increasing the RA lunch dose should reduce glucose levels after lunch. Also, reducing glucose variability will allow further increases in RA lunch dose while keeping hypoglycemia risk low. | | |

TABLE 6-continued

Association of Control Zone ("Zone") and Medication Guidance Output

| Median | Variability | Hyporisk | Zone | Title Text | Dose Adj Text 1 | Dose Adj More Text 1 | Dose Adj Text 2 | Dose Adj More Text 2 |
|---|---|---|---|---|---|---|---|---|
| Above Target | High Variability | Low Hypo Risk | 5 | <same as above> | <same as above> | <same as above> | | |
| Within Target | Low Variability | High Hypo Risk | 10 | Glucose levels are low after lunch, contributing to hypoglycemia risk. Consider the following action: | Decrease RA lunch dose. | Decreasing the RA dose at lunch should reduce hypoglycemia risk after lunch. | | |
| Within Target | Low Variability | Mod Hypo Risk | 6 | <same as above> | <same as above> | <same as above> | | |
| Within Target | High Variability | High Hypo Risk | 13 | Glucose levels are low after lunch. High glucose variability is also contributing to hypoglycemia risk. Consider the following actions: | Reduce variability. | First priority should be to take steps to reduce glucose variability after lunch. If it is unlikely that variability can be reduced substantially, consider the next option. | Or decrease RA lunch dose, if variability cannot be reduced. | If it is not likely that variability after lunch can be reduced, consider decreasing RA lunch dose to reduce hypoglycemia risk. |
| Within Target | Mod Variability | High Hypo Risk | 11 | <same as above> | <same as above> | <same as above> | <same as above> | <same as above> |
| Within Target | Mod Variability | Mod Hypo Risk | 7 | <same as above> | <same as above> | <same as above> | <same as above> | <same as above> |
| Above Target | High Variability | High Hypo Risk | 12 | Glucose levels are high after lunch. However, high glucose variability is contributing to hypoglycemia risk. Consider the following actions: | Reduce variability, no RA lunch dose adjustment | First priority should be to take steps to reduce glucose variability after lunch. If it is unlikely that variability can be reduced substantially, consider the next option. | Or decrease RA lunch dose, if variability cannot be reduced. | If it is not likely that variability after lunch can be reduced, consider decreasing RA lunch dose to reduce hypoglycemia risk. |
| Above Target | High Variability | Mod Hypo Risk | 9 | <same as above> | <same as above> | <same as above> | <same as above> | <same as above> |
| Above Target | Mod Variability | Mod Hypo Risk | 8 | <same as above> | <same as above> | <same as above> | <same as above> | <same as above> |

What is claimed is:

1. A method of using insulin information for meal indication, comprising:
   storing glucose data representative of sensed glucose of a patient over a period of time in a nonvolatile memory;
   collecting, by a processor coupled to the nonvolatile memory, insulin timing information of the patient;
   determining, by the processor, an occurrence of a meal implicitly based on the collected insulin timing information;
   identifying, by the processor, a portion of the glucose data as being temporally related to the meal;
   performing, by the processor, pattern analysis on the portion of the glucose data temporally related to the meal;
   identifying, by the processor, a number of rise or fall patterns in the portion of the glucose data; and
   providing a first treatment recommendation when the number of the rise or fall patterns is indicative of interday variability, and providing a second treatment recommendation when the number of the rise or fall patterns is indicative of intraday variability, wherein the first treatment recommendation is different than the second treatment recommendation.

2. The method of claim 1, wherein at least one of the first or second treatment recommendations is a timing of an insulin bolus or a size of an insulin bolus.

3. The method of claim 1, wherein at least one of the first or second treatment recommendations pertains to a timing of a meal or exercise.

4. The method of claim 1, wherein collecting the insulin timing information comprises receiving manual entry of the insulin timing information.

5. The method of claim 1, wherein collecting the insulin timing information comprises automatically reading the insulin timing information from a dosing device.

6. The method of claim 1, further comprising marking a meal in the glucose data based on the collected insulin timing information.

7. The method of claim 1, further comprising displaying the portion of glucose data on a display in communication with the processor.

8. The method of claim 1, wherein performing, with the processor, pattern analysis on the portion of the glucose data comprises assessing intraday variability and interday variability.

9. The method of claim 1, further comprising providing the first treatment recommendation when the number of the rise or fall patterns is at or above a predetermined number, and providing the second treatment recommendation when the number of the rise or fall patterns is below the predetermined number.

10. A system for using insulin information for meal indication, comprising:
    a glucose sensor configured to collect glucose data representative of sensed glucose levels of a patient;
    a nonvolatile memory in which is stored the glucose data representative of sensed glucose levels of the patient over a period of time; and
    a processor coupled with the nonvolatile memory, wherein the processor is programmed to:
      collect insulin timing information of the patient;
      determine an occurrence of a meal implicitly based on the collected insulin timing information;
      identify a portion of the glucose data as being temporally related to the meal;
      identify a number of rise or fall patterns in the portion of the glucose data; and
      provide a first treatment recommendation when the number of the rise or fall patterns is indicative of interday variability, and provide a second treatment recommendation when the number of the rise or fall patterns is indicative of intraday variability, wherein the first treatment recommendation is different than the second treatment recommendation.

11. The system of claim 10, wherein at least one of the first or second treatment recommendations is a timing of an insulin bolus or a size of an insulin bolus.

12. The system of claim 10, wherein at least one of the first or second treatment recommendations pertains to a timing of a meal or exercise.

13. The system of claim 10, wherein the processor is programmed to receive manual entry of the insulin timing information to collect the insulin timing information of the patient.

14. The system of claim 10, wherein the processor is programmed to automatically read the insulin timing information from a dosing device to collect the insulin timing information of the patient.

15. The system of claim 10, wherein the processor is programmed to mark a meal in the glucose data based on the insulin timing information.

16. The system of claim 10, further comprising a display, wherein the processor is programmed to cause display of the portion of glucose data on the display.

17. The system of claim 10, wherein the processor is programmed to assess intraday variability and interday variability.

18. The system of claim 10, wherein the processor is programmed to perform pattern analysis on the portion of the glucose data temporally related to the meal.

19. The system of claim 10, wherein the processor is further programmed to provide the first treatment recommendation when the number of the rise or fall patterns is at or above a predetermined number, and provide the second treatment recommendation when the number of the rise or fall patterns is below the predetermined number.

* * * * *